US012391765B2

(12) United States Patent
Smithson et al.

(10) Patent No.: US 12,391,765 B2
(45) Date of Patent: Aug. 19, 2025

(54) METHODS AND MATERIALS FOR ASSESSING RESPONSE TO PLASMABLAST- AND PLASMA CELL-DEPLETING THERAPIES

(71) Applicant: Takeda Pharmaceutical Company Limited, Osaka (JP)

(72) Inventors: Glennda Smithson, Antioch, IL (US); Jose Estevam, Quincy, MA (US); Nicholas Jones, LaVergne, TN (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/169,767

(22) Filed: Feb. 15, 2023

(65) Prior Publication Data
US 2023/0357426 A1    Nov. 9, 2023

Related U.S. Application Data

(62) Division of application No. 16/317,606, filed as application No. PCT/US2017/042128 on Jul. 14, 2017, now Pat. No. 11,613,586.

(60) Provisional application No. 62/362,963, filed on Jul. 15, 2016.

(51) Int. Cl.
*C07K 16/28* (2006.01)
*A61K 39/00* (2006.01)
*A61P 19/02* (2006.01)
*G01N 33/569* (2006.01)

(52) U.S. Cl.
CPC .......... *C07K 16/2896* (2013.01); *A61P 19/02* (2018.01); *G01N 33/56966* (2013.01); *A61K 2039/505* (2013.01); *C07K 2317/21* (2013.01); *C07K 2317/732* (2013.01); *C07K 2317/734* (2013.01); *G01N 2333/91148* (2013.01)

(58) Field of Classification Search
None
See application file for complete search history.

(56) References Cited

U.S. PATENT DOCUMENTS

| | | |
|---|---|---|
| 6,086,875 A | 7/2000 | Blumberg et al. |
| 6,737,056 B1 | 5/2004 | Presta |
| 7,317,091 B2 | 1/2008 | Lazar et al. |
| 7,670,600 B2 | 3/2010 | Dall'Acqua et al. |
| 7,829,673 B2 | 11/2010 | De Weers et al. |
| 8,084,582 B2 | 12/2011 | Dahiyat et al. |
| 8,088,896 B2 | 1/2012 | Tesar et al. |
| 8,188,231 B2 | 5/2012 | Lazar et al. |
| 8,362,211 B2 | 1/2013 | Elias et al. |
| 8,367,805 B2 | 2/2013 | Chamberlain et al. |
| 8,877,899 B2 | 11/2014 | Rojkjaer et al. |
| 8,926,969 B2 | 1/2015 | Elias et al. |
| 8,937,158 B2 | 1/2015 | Lazar et al. |
| 9,040,041 B2 | 5/2015 | Desjarlais et al. |
| 9,040,050 B2 | 5/2015 | van de Winkel et al. |
| 9,102,744 B2 | 8/2015 | Elias et al. |
| 9,289,490 B2 | 3/2016 | Rojkjaer et al. |
| 9,676,869 B2 | 6/2017 | Elias et al. |
| 9,790,285 B2 | 10/2017 | Elias et al. |
| 9,944,711 B2 | 4/2018 | De Weers et al. |
| 10,232,041 B2 | 3/2019 | Pogue et al. |
| 10,336,833 B2 | 7/2019 | Elias et al. |
| 10,494,444 B2 | 12/2019 | Elias et al. |
| 11,613,586 B2* | 3/2023 | Smithson ............ A61P 1/00 424/139.1 |
| 2004/0013210 A1 | 1/2004 | Bollano et al. |
| 2005/0054832 A1 | 3/2005 | Lazar et al. |
| 2005/0261480 A1 | 11/2005 | Foote |
| 2006/0024298 A1 | 2/2006 | Lazar et al. |
| 2006/0121032 A1 | 6/2006 | Dahiyat et al. |
| 2006/0235208 A1 | 10/2006 | Lazar et al. |
| 2007/0003554 A1 | 1/2007 | Miller |
| 2007/0148170 A1 | 6/2007 | Desjarlais et al. |
| 2009/0076249 A1 | 3/2009 | De Weers et al. |
| 2009/0148449 A1 | 6/2009 | De Weers et al. |
| 2009/0203538 A1 | 8/2009 | Sugioka et al. |
| 2010/0028346 A1 | 2/2010 | Lutz et al. |
| 2010/0092489 A1 | 4/2010 | van de Winkel et al. |
| 2011/0099647 A1 | 4/2011 | De Weers et al. |
| 2011/0262454 A1 | 10/2011 | Park et al. |
| 2013/0209355 A1 | 8/2013 | De Weers et al. |

(Continued)

FOREIGN PATENT DOCUMENTS

CN    103282383 A    9/2013
CN    107365385 A    11/2017
(Continued)

OTHER PUBLICATIONS

Alexander, Tobias et al. "The proteasome inhibitior bortezomib depletes plasma cells and ameliorates clinical manifestations of refractory systemic lupus erythematosus." Annals of the rheumatic diseases vol. 74,7 (2015): 1474-8.

Alvarez-Rodriguez, Lorena et al. "Peripheral B-Cell Subset Distribution in Primary Antiphospholipid Syndrome." International journal of molecular sciences vol. 19,2 589. Feb. 16, 2018.

Atanackovic, Djordje et al. "Immunotherapies targeting CD38 in Multiple Myeloma." Oncoimmunology vol. 5,11 e1217374. Aug. 5, 2016, doi:10.1080/2162402X.2016.1217374.

Ausiello et al., Functional topography of discrete domains of human CD38., Tissue Antigens. Dec. 2000;56(6):539-47.

(Continued)

*Primary Examiner* — Phuong Huynh
(74) *Attorney, Agent, or Firm* — Morgan, Lewis & Bockius LLP

(57) ABSTRACT

The present disclosure relates to anti-CD38 antibodies and their use as therapeutics and diagnostics. The present disclosure further relates to methods of treating autoimmune diseases, such as systemic lupus erythematosus and rheumatoid arthritis. The present disclosure further relates to diagnostic assay methods for identifying patients having autoimmune diseases for treatment.

19 Claims, 21 Drawing Sheets

Specification includes a Sequence Listing.

(56) References Cited

U.S. PATENT DOCUMENTS

| | | |
|---|---|---|
| 2013/0302318 A1 | 11/2013 | Rojkjaer et al. |
| 2014/0154247 A1 | 6/2014 | Behrens et al. |
| 2014/0161819 A1 | 6/2014 | Hann et al. |
| 2015/0231235 A1 | 8/2015 | van de Winkel et al. |
| 2016/0067205 A1 | 3/2016 | Lokhorst et al. |
| 2016/0075766 A1 | 3/2016 | Ritter et al. |
| 2016/0130362 A1 | 5/2016 | De Weers et al. |
| 2016/0139117 A1 | 5/2016 | Yamamura et al. |
| 2016/0168266 A1 | 6/2016 | Yamazaki et al. |
| 2017/0008966 A1 | 1/2017 | Chaulagain et al. |
| 2017/0107295 A1 | 4/2017 | Lokhorst et al. |
| 2017/0121417 A1 | 5/2017 | Jansson et al. |
| 2017/0224817 A1 | 8/2017 | Venstrom |
| 2018/0022823 A1 | 1/2018 | Rojkjaer et al. |
| 2018/0117150 A1 | 5/2018 | O'Dwyer et al. |
| 2018/0235986 A1 | 8/2018 | Labotka et al. |
| 2019/0127479 A1 | 5/2019 | Ahmadi et al. |
| 2021/0171650 A1 | 6/2021 | Audat et al. |
| 2021/0388103 A1 | 12/2021 | Smithson et al. |

FOREIGN PATENT DOCUMENTS

| | | |
|---|---|---|
| EP | 1914242 | 4/2008 |
| EP | 2658871 B1 | 5/2018 |
| JP | 2001-509817 A | 7/2001 |
| JP | 2014-502491 A | 2/2014 |
| JP | 2014-509837 A | 4/2014 |
| JP | 2014-514345 A | 6/2014 |
| JP | 2015-511008 A | 4/2015 |
| JP | 2015-522822 A | 8/2015 |
| JP | 2016-536314 A | 11/2016 |
| KR | 10-2014-0032963 A | 3/2014 |
| TW | 201919699 A | 6/2019 |
| WO | WO 1994/013804 A1 | 6/1994 |
| WO | WO 1998/45331 A2 | 10/1998 |
| WO | WO 2003/011161 A1 | 2/2003 |
| WO | WO 2006/099875 | 9/2006 |
| WO | WO 2006/125640 | 11/2006 |
| WO | WO 2008/037257 | 4/2008 |
| WO | WO 2008/047242 A2 | 4/2008 |
| WO | WO 2009/077993 | 6/2009 |
| WO | WO 2010/021874 | 2/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2012/076663 A1 | 6/2012 |
| WO | WO 2012/080721 A2 | 6/2012 |
| WO | WO 2012/092612 | 7/2012 |
| WO | WO 2012/092616 | 7/2012 |
| WO | WO 2012/118750 A2 | 9/2012 |
| WO | WO 2012/151199 A1 | 11/2012 |
| WO | WO 2013/132245 A1 | 9/2013 |
| WO | WO 2014/013225 A1 | 1/2014 |
| WO | WO 2014/089416 A1 | 6/2014 |
| WO | WO 2015/066450 A1 | 5/2015 |
| WO | WO 2016/180958 A1 | 11/2016 |
| WO | WO 2017/079150 A1 | 5/2017 |
| WO | WO 2018/013917 A1 | 1/2018 |
| WO | WO 2019/089832 A1 | 5/2019 |

OTHER PUBLICATIONS

Banchereau, Romain et al. "Personalized Immunomonitoring Uncovers Molecular Networks that Stratify Lupus Patients." Cell vol. 165,3 (2016): 551-65.
Barbas, C F 3rd et al. "In vitro evolution of a neutralizing human antibody to human immunodeficiency virus type 1 to enhance affinity and broaden strain cross-reactivity." Proceedings of the National Academy of Sciences of the United States of America vol. 91,9 (1994): 3809-13.
Behzad, Masumeh Maleki et al. "Cellular expression of CD markers in immune thrombocytopenia purpura: implications for prognosis." APMIS : acta pathologica, microbiologica, et immunologica Scandinavica vol. 126,6 (2018): 523-532.
Bird, R E et al. "Single-chain antigen-binding proteins." Science (New York, N.Y.) vol. 242,4877 (1988): 423-6.
Casneuf, Tineke et al. "Effects of daratumumab on natural killer cells and impact on clinical outcomes in relapsed or refractory multiple myeloma." Blood advances vol. 1,23 2105-2114. Oct. 24, 2017.
Chiba, Asako et al. "The involvement of V(alpha) 14 natural killer T cells in the pathogenesis of arthritis in murine models." Arthritis and rheumatism vol. 52,6 (2005): 1941-8.
Chihara, Norio et al. "Interleukin 6 signaling promotes anti-aquaporin 4 autoantibody production from plasmablasts in neuromyelitis optica." Proceedings of the National Academy of Sciences of the United States of America vol. 108,9 (2011): 3701-6.
Chothia, C, and A M Lesk. "Canonical structures for the hypervariable regions of immunoglobulins." Journal of molecular biology vol. 196,4 (1987): 901-17.
Clemens, Pamela L et al. "Pharmacokinetics of Daratumumab Following Intravenous Infusion in Relapsed or Refractory Multiple Myeloma After Prior Proteasome Inhibitor and Immunomodulatory Drug Treatment." Clinical pharmacokinetics vol. 56,8 (2017): 915-924.
Cohen, Adam D, and Raymond L Comenzo. "Systemic light-chain amyloidosis: advances in diagnosis, prognosis, and therapy." Hematology. American Society of Hematology. Education Program vol. 2010 (2010): 287-94.
Cole, Suzanne et al. "Integrative analysis reveals CD38 as a therapeutic target for plasma cell-rich pre-disease and established rheumatoid arthritis and systemic lupus erythematosus." Arthritis research & therapy vol. 20,1 85. May 2, 2018.
Cooper, L J et al. "Role of heavy chain constant domains in antibody-antigen interaction. Apparent specificity differences among *Streptococcal* IgG antibodies expressing identical variable domains." Journal of immunology (Baltimore, Md. : 1950) vol. 150,6 (1993): 2231-42.
Costello, Caitlin. "An update on the role of daratumumab in the treatment of multiple myeloma." Therapeutic advances in hematology vol. 8,1 (2017): 28-37.
Daratumumab (Darzalex) I FDA, May 17, 2017, retrieved from the Internet: URL:https://www.fda.gov/drugs/resources-information-approved-drugs/ daratumumab-darzalex.
De Weers, Michel et al. "Daratumumab, a novel therapeutic human CD38 monoclonal antibody, induces killing of multiple myeloma and other hematological tumors." Journal of immunology (Baltimore, Md. : 1950) vol. 186,3 (2011): 1840-8.
Dimopoulos et al. (2018) Blood 132 (suppl. 1): ASH abstract 155/ oral presentation.
Duebel "Handbook of Therapeutic Antibodies Chapter 6" Handbook of Therapeutic Antibodies, pp. 119-144 (2007).
Dürig, J et al. "CD38 expression is an important prognostic marker in chronic lymphocytic leukaemia." Leukemia vol. 16,1 (2002): 30-5.
Ellis et al., "Engineered Anti-CD38 Monoclonal Antibodies for Immunotherapy of Multiple Myeloma", J Immunology, 1995, 155: 925-9237.
Fedyk, E et al. "A Single Administration of the Cytolytic CD38 Antibody TAK-079 to Healthy Subjects: Tolerability, Pharmacokinetics and Pharmacodynamics." Blood 2018; 132 (Supplement 1): 3249. doi: https://doi.org/10.1182/blood-2018-99-112916.
Ferrero et al., Characterization and phylogenetic epitope mapping of CD38 ADPR cyclase in the cynomolgus macaque., BMC Immunol. Sep. 21, 2004;5:21.
Foote, J., et al. "Antibody framework residues affecting the conformation of the hypervariable loops." Journal of molecular biology, vol. 224,2 (1992): 487-99.
Friberg, Lena E et al. "Model of chemotherapy-induced myelosuppression with parameter consistency across drugs." Journal of clinical oncology : official journal of the American Society of Clinical Oncology vol. 20,24 (2002): 4713-21.
Gertz, Morie A et al. "Amyloidosis and Waldenstrom's macroglobulinemia." Hematology. American Society of Hematology. Education Program (2004): 257-82.
Gibiansky, Leonid, and Ekaterina Gibiansky. "Target-mediated drug disposition model: approximations, identifiability of model param-

(56) References Cited

OTHER PUBLICATIONS eters and applications to the population pharmacokinetic-pharmacodynamic modeling of biologics." Expert opinion on drug metabolism & toxicology vol. 5,7 (2009): 803-12.
Glassman, Patrick M, and Joseph P Balthasar. "Mechanistic considerations for the use of monoclonal antibodies for cancer therapy." Cancer biology & medicine vol. 11,1 (2014): 20-33.
Goldmacher et al., "Anti-CD38-blocked-ricin; An immunotoxin for the treatment of multiple myeloma", Blood 84(9); 3017-25, Nov. 1, 1994.
Grammer, Amrie C et al. "Abnormal germinal center reactions in systemic lupus erythematosus demonstrated by blockade of CD154-CD40 interactions." The Journal of clinical investigation vol. 112,10 (2003): 1506-20.
Groen, Richard W. et al., "In Vitro and In Vivo Efficacy of CD38 Directed Therapy with Daratumumab in the Treatment of Multiple Myeloma", Blood, vol. 116, No. 21, Nov. 2010, pp. 1261-1262, XP009157537.
Hamblin, Terry J et al. "CD38 expression and immunoglobulin variable region mutations are independent prognostic variables in chronic lymphocytic leukemia, but CD38 expression may vary during the course of the disease." Blood vol. 99,3 (2002): 1023-9.
Han, Chao, and Honghui Zhou. "Monoclonal antibodies: interspecies scaling with minimal preclinical information." Therapeutic delivery vol. 2,3 (2011): 359-68.
Hawkins, R E et al. "Selection of phage antibodies by binding affinity. Mimicking affinity maturation." Journal of molecular biology vol. 226,3 (1992): 889-96.
Holliger, P et al. ""Diabodies": small bivalent and bispecific antibody fragments." Proceedings of the National Academy of Sciences of the United States of America vol. 90,14 (1993): 6444-8.
Huston, J S et al. "Protein engineering of antibody binding sites: recovery of specific activity in an anti-digoxin single-chain Fv analogue produced in *Escherichia coli*." Proceedings of the National Academy of Sciences of the United States of America vol. 85,16 (1988): 5879-83.
International Myeloma Working Group. "Criteria for the classification of monoclonal gammopathies, multiple myeloma and related disorders: a report of the International Myeloma Working Group." British journal of haematology vol. 121,5 (2003): 749-57.
Ishizawa, Kenichi et al. "Safety, efficacy and pharmacokinetics of humanized anti-CD52 monoclonal antibody alemtuzumab in Japanese patients with relapsed or refractory B-cell chronic lymphocytic leukemia." Japanese journal of clinical oncology vol. 47,1 (2017): 54-60.
Jackson, J R et al. "In vitro antibody maturation. Improvement of a high affinity, neutralizing antibody against IL-1 beta." Journal of immunology (Baltimore, Md. : 1950) vol. 154,7 (1995): 3310-9.
Jackson, N et al. "An analysis of myeloma plasma cell phenotype using antibodies defined at the IIIrd International Workshop on Human Leucocyte Differentiation Antigens." Clinical and experimental immunology vol. 72,3 (1988): 351-6.
Jelinek, D F et al. "Analysis of clonal B-cell CD38 and immunoglobulin variable region sequence status in relation to clinical outcome for B-chronic lymphocytic leukaemia." British journal of haematology vol. 115,4 (2001): 854-61.
Kabat et al. (1991) Sequences of Proteins of Immunological Interest, 5th Ed. Public Health Service, National Institutes of Health, Bethesda, MD.
Kamath, Amrita V. "Translational pharmacokinetics and pharmacodynamics of monoclonal antibodies." Drug discovery today. Technologies vol. 21-22 (2016): 75-83.
Kato, Atsuhiko et al. "Early effects of tocilizumab on bone and bone marrow lesions in a collagen-induced arthritis monkey model." Experimental and molecular pathology vol. 84,3 (2008): 262-70.
Keizer, R J et al. "Modeling and Simulation Workbench for NONMEM: Tutorial on Pirana, PsN, and Xpose." CPT: pharmacometrics & systems pharmacology vol. 2,6 e50. Jun. 26, 2013.

Keyhani, A et al. "Increased CD38 expression is associated with favorable prognosis in adult acute leukemia." Leukemia research vol. 24,2 (2000): 153-9.
Kiyoshi MA, et al.: "Affinity improvement of a therapeutic antibody by structure-based computational design: generation of electrostatic interactions in the transition states stabilized the antibody-antigen complex". PLoS One. Jan. 27, 2014;9(1).
Kong, Sun-Young et al., "Daratumumab Directly Induces Human Multiple Myeloma Cell Death and Acts Synergistically with Conventional and Novel Anti-Myeloma Drugs", Blood, vol. 116, No. 21, Nov. 2010, pp. 1241-1242, XP009157536.
Kosmas, C et al. "Anti-CD20-based therapy of B cell lymphoma: state of the art." Leukemia vol. 16,10 (2002): 2004-15.
Kraan, M C et al. "Immunohistological analysis of synovial tissue for differential diagnosis in early arthritis." Rheumatology (Oxford, England) vol. 38,11 (1999): 1074-80.
Krejcik, Jakub et al. "Daratumumab depletes CD38+ immune regulatory cells, promotes T-cell expansion, and skews T-cell repertoire in multiple myeloma." Blood vol. 128,3 (2016): 384-94.
Kuerten et al., MP4- and MOG:35-55-induced EAE in C57BL/6 mice differentially targets brain, spinal cord and cerebellum., J Neuroimmunol. Sep. 2007;189(1-2):31-40. Epub Jul. 25, 2007.
Kyle, Robert A et al. "Clinical course and prognosis of smoldering (asymptomatic) multiple myeloma." The New England journal of medicine vol. 356,25 (2007): 2582-90.
Laubach, Jacob P, and Paul G Richardson. "CD38-Targeted Immunochemotherapy in Refractory Multiple Myeloma: A New Horizon." Clinical cancer research : an official journal of the American Association for Cancer Research vol. 21,12 (2015): 2660-2. doi:10.1158/1078-0432.CCR-14-3190.
Mager, Donald E et al. "Diversity of mechanism-based pharmacodynamic models." Drug metabolism and disposition: the biological fate of chemicals vol. 31,5 (2003): 510-8.
Marinov, J et al. "Immunophenotypic significance of the "lymphoid" CD38 antigen in myeloid blood malignancies." Neoplasma vol. 40,6 (1993): 355-8.
Marks, J., Griffiths, A., Malmqvist, M et al. By-Passing Immunization: Building High Affinity Human Antibodies by Chain Shuffling. Nat Biotechnol 10, 779-783 (1992).
Merlini, Giampaolo, and Vittorio Bellotti. "Molecular mechanisms of amyloidosis." The New England journal of medicine vol. 349,6 (2003): 583-96.
Mihara, M et al. "Humanized antibody to human interleukin-6 receptor inhibits the development of collagen arthritis in cynomolgus monkeys." Clinical immunology (Orlando, Fla.) vol. 98,3 (2001): 319-26.
Morabito, F et al. "Peripheral blood CD38 expression predicts survival in B-cell chronic lymphocytic leukemia." Leukemia research vol. 25,11 (2001): 927-32.
Murray et al. (2010) Blood (ASH Annual Meeting Abstracts) 116 (21): abstr 1909.
Mustafa, Nurulhuda et al., "Daratumumab Efficiently Targets NK/T Cell Lymphoma with High CD38 Expression." Blood 2017; 130 (Supplement 1): 2814.
Nijhof, Inger S et al. "CD38 expression and complement inhibitors affect response and resistance to daratumumab therapy in myeloma." Blood vol. 128,7 (2016): 959-70.
Nilsson and Koke (2001) Drug Inform. J. 35: 1289-1299.
Palumbo, Antonio et al. "International Myeloma Working Group consensus statement for the management, treatment, and supportive care of patients with myeloma not eligible for standard autologous stem-cell transplantation." Journal of clinical oncology : official journal of the American Society of Clinical Oncology vol. 32,6 (2014): 587-600. doi:10.1200/JCO.2013.48.7934.
Park, Peter U. et al., "SAR650984: A Potent Anti-CD38 Therapeutic Antibody with Three Mechanisms of Action (Apoptosis, ADCC, CDC) for Hematological Malignancies.", Blood, vol. 112, No. 11, Nov. 2008, p. 951, XP009157535.
Raab, M. S. et al. "Phase I/IIa Study of the Human Anti-CD38 Antibody MOR202 (MOR03087) in Relapsed or Refractory Multiple Myeloma." Blood, vol. 126,23, 2015, p. 3035.
Rajkumar, S Vincent et al. "Consensus recommendations for the uniform reporting of clinical trials: report of the International

(56) References Cited

OTHER PUBLICATIONS

Myeloma Workshop Consensus Panel 1." Blood vol. 117,18 (2011): 4691-5. doi:10.1182/blood-2010-10-299487.
Reiter, Y et al. "Engineering antibody Fv fragments for cancer detection and therapy: disulfide-stabilized Fv fragments." Nature biotechnology vol. 14,10 (1996): 1239-45.
Rich RL et al: "A global benchmark study using affinity-based biosensors" Analytical Biochemistry, Mar. 15, 2009;386(2): 194-216.
Richter et al. (2016) J. Clin. Oncol. 34 (suppl): abstr 8005.
Roepcke, Stefan et al. "Pharmacokinetics and pharmacodynamics of the cytolytic anti-CD38 human monoclonal antibody TAK-079 in monkey—model assisted preparation for the first in human trial." Pharmacology research & perspectives vol. 6,3 (2018): e00402.
Schier, R et al. "Identification of functional and structural amino-acid residues by parsimonious mutagenesis." Gene vol. 169,2 (1996): 147-55.
Shaul, Merav E et al. "Tumor-associated neutrophils display a distinct N1 profile following TGFβ modulation: A transcriptomics analysis of pro- vs. antitumor TANs." Oncoimmunology vol. 5,11 e1232221. Sep. 13, 2016, doi:10.1080/2162402X.2016.1232221.
Smithson, G. et al. "TAK-079 is a high affinity monoclonal antibody that effectively mediates CD38+ cell depletion." J. Immunol. 198 (1 Supplement) (2017) 224.20.
Sonneveld, Pieter, and Annemiek Broijl. "Treatment of relapsed and refractory multiple myeloma." Haematologica vol. 101,4 (2016): 396-406.
Stebbings, Richard et al. ""Cytokine storm" in the phase I trial of monoclonal antibody TGN1412: better understanding the causes to improve preclinical testing of immunotherapeutics." Journal of immunology (Baltimore, Md. : 1950) vol. 179,5 (2007): 3325-31.
Stevenson et al., "Preliminary studies for an immunotherapeutic approach to the treatment of human myeloma using chimeric anti-CD38 antibody", Blood, 1991, 77: 1071-1079.
Stevenson, G. T., "CD38 as a Therapeutic Target", Molecular Medicine, 2006, vol. 12, pp. 345-346.
Study NCT02219256. A Phase 1 Study to Assess the Safety, Tolerability, and Pharmacokinetics of TAK-079 in Healthy Participants, clinicaltrials.gov, Mar. 22, 2017, pp. 1-13; found on the Internet Dec. 15, 2021, URL: https://clinicaltrials.gov/ct2/history/NCT02219256?V_8=View#StudyPageTop.
Sullivan, Harold C et al. "Daratumumab (anti-CD38) induces loss of CD38 on red blood cells." Blood vol. 129,22 (2017): 3033-3037.
Tomlinson, I, and P Holliger. "Methods for generating multivalent and bispecific antibody fragments." Methods in enzymology vol. 326 (2000): 461-79.
Uchiyama, Yasushi et al. "Anemia in monkey collagen-induced arthritis is correlated with serum IL-6, but not TNFalpha." Rheumatology international vol. 28,9 (2008): 879-83.
Uchiyama, Yasushi et al. "Tocilizumab, a humanized anti-interleukin-6 receptor antibody, ameliorates joint swelling in established monkey collagen-induced arthritis." Biological & pharmaceutical bulletin vol. 31,6 (2008): 1159-63.
Usmani S.Z. et al., Open-Label, Multicenter, Dose Escalation Phase 1b Study to Assess the Subcutaneous Delivery of Daratumumab in Patients(pts) with Relapsed or Refractory Multiple Myeloma (PAVO), Blood, 2016, vol. 128 (22) : 1149.
Van Bueren, J. et al. "Direct in Vitro Comparison of Daratumumab with Surrogate Analogs of CD38 Antibodies MOR03087, SAR650984 and Ab79" Blood 2014; 124 (21): 3474. doi: https://doi.org/10.1182/blood.V124.21.3474.3474.
Van de Donk, Niels Wc J et al. "CD38 antibodies in multiple myeloma: back to the future." Blood vol. 131,1 (2018): 13-29. doi:10.1182/blood-2017-06-740944.
Van de Donk, Niels W C J et al. "Monoclonal antibodies targeting CD38 in hematological malignancies and beyond." Immunological reviews vol. 270,1 (2016): 95-112.
Van Noort et al., Cell biology of autoimmune diseases., Int Rev Cytol. 1998; 178:127-206.
Vital, Edward M et al. "B cell biomarkers of rituximab responses in systemic lupus erythematosus." Arthritis and rheumatism vol. 63,10 (2011): 3038-47.
Voorhees, Peter M., et al. "Management of Infusion-Related Reactions Following Daratumumab Monotherapy in Patients with at Least 3 Lines of Prior Therapy or Double Refractory Multiple Myeloma (MM): 54767414MMY2002" (Sirius). Blood 2015; 126 (23): 1829.
Walpole, Sarah Catherine et al. "The weight of nations: an estimation of adult human biomass." BMC public health vol. 12 439. Jun. 18, 2012, doi:10.1186/1471-2458-12-439.
Wang et al. (2016) Arthritis Rheumatol. 68(suppl 10). 2016 ACR/ARHP Annual Meeting, 1085.
Ward, E S et al. "Binding activities of a repertoire of single immunoglobulin variable domains secreted from *Escherichia coli*." Nature vol. 341,6242 (1989): 544-6.
Winter, G., et al. "Humanized antibodies." Immunology today, vol. 14,6 (1993): 243-6.
Witzig, T E et al. "Quantitation of circulating peripheral blood plasma cells and their relationship to disease activity in patients with multiple myeloma." Cancer vol. 72,1 (1993): 108-13.
Xu, X S et al. "Clinical Implications of Complex Pharmacokinetics for Daratumumab Dose Regimen in Patients With Relapsed/Refractory Multiple Myeloma." Clinical pharmacology and therapeutics vol. 101,6 (2017): 721-724.
Yelton, D E et al. "Affinity maturation of the BR96 anti-carcinoma antibody by codon-based mutagenesis." Journal of immunology (Baltimore, Md. : 1950) vol. 155,4 (1995): 1994-2004.
Yilmaz, Vuslat et al. "Regulatory B cells in myasthenia gravis are differentially affected by therapies." Annals of clinical and translational neurology vol. 5,11 1408-1414. Sep. 22, 2018.
Yoshiga, Y et al. "Invariant NKT cells produce IL-17 through IL-23-dependent and—independent pathways with potential modulation of Th17 response in collagen-induced arthritis." International journal of molecular medicine vol. 22,3 (2008): 369-74.
Yu. B. Belousov, K. G. Gurevich. Clinical pharmacokinetics. The practice of dosing drugs. Moscow, Litterra Publishing House, 2005, 288 p., see p. 18, last paragraph,—p. 20 (Russian).
Zhang, Tiantian et al. "Systematic review and meta-analysis of the efficacy and safety of novel monoclonal antibodies for treatment of relapsed/refractory multiple myeloma." Oncotarget vol. 8,20 (2017): 34001-34017. doi:10.18632/oncotarget.16987.
Aggarwal, Rohit et al. "Serum free light chains as biomarkers for systemic lupus erythematosus disease activity." Arthritis care & research vol. 63,6 (2011): 891-8. doi:10.1002/acr.20446.
Antonelli et al., Clin. Exp. Immunol. 2001 126:426-431.
Antonelli et al., J. Endocrinol. Invest. 27:695-707 (2004).
Cole, S., et al. "Integrative analysis reveals CD38 as a therapeutic target for plasma cell-rich pre-disease and established rheumatoid arthritis and systemic lupus erythematosus." *Arthritis research & therapy* vol. 20,1 85. May 2, 2018.
Draborg, A.H., Lydolph MC, Westergaard M, et al., PLoS One (2015) 10(9):e0138753. doi: 10.1371/journal.pone.0138753. eCollection 2015.
Edwards, Bryan M et al. "The remarkable flexibility of the human antibody repertoire; isolation of over one thousand different antibodies to a single protein, BLyS." Journal of molecular biology vol. 334,1 (2003): 103-18. doi:10.1016/j.jmb.2003.09.054.
Fassbinder, T., Saunders U, Mickholz E, et al., Arthritis Res Ther (2015).
Hutchinson, A., "Cell membrane associated free kappa light chains are found on a subset of tonsil and in vitro-derived plasmablasts" Human Immunology, vol. 75, Issue 9 (2014) pp. 986-990.
IOTest&αχιρχ; CD38-PE // A07779CE_C Feb. 6, 2006 //[online], [found on Nov. 3, 2020]. found on: https://www.bc-cytometry.com/PDF/DataSheet/A07779_D.S.pdf.
Kormelink, T. G. et al. "Decrease in immunoglobulin free light chains in patients with rheumatoid arthritis upon rituximab (anti-CD20) treatment correlates with decrease in disease activity." Annals of the rheumatic diseases vol. 69,12 (2010): 2137-44.
Little, M. et al., "Of mice and men: hybridoma and recombinant antibodies", Immunology Today, El Sevier Publications, Cambridge, GB, vol. 21, No. 8, Aug. 2000, pp. 364-370, XP004215163.

(56) References Cited

OTHER PUBLICATIONS

Lloyd, C et al. "Modelling the human immune response: performance of a 1011 human antibody repertoire against a broad panel of therapeutically relevant antigens." Protein engineering, design & selection : PEDS vol. 22,3 (2009): 159-68. doi:10.1093/protein/gzn058.
Lugar, Patricia L et al. "Molecular characterization of circulating plasma cells in patients with active systemic lupus erythematosus." PloS one vol. 7,9 (2012): e44362. doi:10.1371/journal.pone.0044362.
Malavasi, F., Deaglio S, Funaro A, et al., Physiol Rev (2008) 88(3):841-86.
Mallone et al., Diabetes 50:752 (2001).
Martin, W. et al., "Serum-free light chain—a new biomarker for patients with B-cell non-Hodgkin lymphoma and chronic lymphocytic leukemia", Translational Research, vol. 149, Issue 4, 2007, pp. 231-235, https://doi.org/10.1016/j.trsl.2006.11.001.
Mei, H. et al. "Rationale of anti-CD19 immunotherapy: an option to target autoreactive plasma cells in autoimmunity." Arthritis research & therapy vol. 14 Suppl 5,Suppl 5 (2012): S1. doi:10.1186/ar3909.
Odendahl, M., "Disturbed peripheral B lymphocyte homeostasis in systemic lupus erythematosus.", J Immunol. Nov. 15, 2000;165(10):5970-9.
Odendahl, M., "Perturbations of peripheral B lymphocyte homoeostasis in children with systemic lupus erythematosus.", Ann Rheum Dis. Sep. 2003;62(9):851-8.
Owczarczyk, K., "A plasmablast biomarker for nonresponse to antibody therapy to CD20 in rheumatoid arthritis.", Sci Transl Med. Sep. 21, 2011;3(101):101ra92.
Pavon, E.J., "Increased association of CD38 with lipid rafts in T cells from patients with systemic lupus erythematosus and in activated normal T cells.", Mol Immunol. Mar. 2006;43(7):1029-39. Epub Jun. 16, 2005.

PCT Search Report and Written Opinion prepared for PCT/US2017/042128, completed Aug. 23, 2017.
Pinto, L. et al. "Fixation and cryopreservation of whole blood and isolated mononuclear cells: Influence of different procedures on lymphocyte subset analysis by flow cytometry." Cytometry. Part B, Clinical cytometry vol. 63,1 (2005): 47-55. doi:10.1002/cyto.b.20038.
Vital, E.M., "Management of nonresponse to rituximab in rheumatoid arthritis: predictors and outcome of re-treatment.", Arthritis Rheum. May 2010;62(5):1273-9.
Davda JP et al. A model-based meta-analysis of monoclonal antibody pharmacokinetics to guide optimal first-in-human study design (mAbs, 2015 6:4, 1094-1102) (Year: 2015).
Doyle GR et al. Chapter 7.3 Intradermal and Subcutaneous Injections. Clinical Procedures for Safer Patient Care (publication date Nov. 23, 2015) (https://opentextbc.ca/clinicalskills/chapter/6-7-intradermal-subcutaneous-and-intramuscular-injections/). (Year: 2015).
International Preliminary Report on Patentability for International Patent Application No. PCT/US17/42128 mailed Jan. 15, 2019, 9 pages.
International Search Report and Written Opinion for International Patent Application No. PCT/US17/42128 mailed Dec. 1, 2017, 16 pages.
Perez-Ramirez: "Approaches in subcutaneous delivery of monoclonal antibodies", European Pharmaceutical Review, Aug. 24, 2016 (Aug. 24, 2016), pp. 1-22, XP055573387.
Pivot, X et al. "Efficacy and safety of subcutaneous trastuzumab and intravenous trastuzumab as part of adjuvant therapy for HER2-positive early breast cancer: Final analysis of the randomised, two-cohort PrefHer study." European journal of cancer (Oxford, England : 1990) vol. 86 (2017): 82-90. doi:10.1016/j.ejca.2017.08.019.

* cited by examiner

FIG. 2A

Ab79 Heavy Chain (SEQ ID NO:21)

EVQLLESGGGLVQPGGSLRLSCAASGFTFDDYGMSWVRQAPGKGLEWVSDISWNGGK
THYVDSVKGQFTISRDNSKNTLYLQMNSLRAEDTAVYYCARGSLFHDSSGFYFGHWG
QGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTC
PPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

Ab79 Light Chain (SEQ ID NO:22)

QSVLTQPPSASGTPGQRVTISCSGSSSNIGDNYVSWYQQLPGTAPKLLIYRDSQRPSGVP
DRFSGSKSGTSASLAISGLRSEDEADYYCQSYDSSLSGSVFGGGTKLTVLGQPKANPTV
TLFPPSSEELQANKATLVCLISDFYPGAVTVAWKADGSPVKAGVETTKPSKQSNNKYA
ASSYLSLTPEQWKSHRSYSCQVTHEGSTVEKTVAPTECS

Ab19 Heavy Chain (SEQ ID NO:19)

EVQLLESGGGLVQPGGSLRLSCAASGFTFNNYDMTWVRQAPGKGLEWVAVISYDGSD
KDYADSVKGRFTISRDNSKNTLYLQMNSLRAEDTAVYYCARVYYYGFSGPSMDVWG
QGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHTC
PPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

FIG. 2B

Ab19 Light Chain (SEQ ID NO:20)

QSVLTQPPSASGTPGQRVTISCSGSNSNIGSNTVNWYQQLPGTAPKLLIYSDSNRPSGVP
DRFSGSKSGTSASLAISGLRSEDEADYYCQSYDSSLSGSRVFGGGTKLTVLGQPKANPT
VTLFPPSSEELQANKATLVCLISDFYPGAVTVAWKADGSPVKAGVETTKPSKQSNNKY
AASSYLSLTPEQWKSHRSYSCQVTHEGSTVEKTVAPTECS

FIG. 3

CD38 Homo sapiens (Accession NP_001766.2; SEQ ID NO:1)

MANCEFSPVSGDKPCCRLSRRAQLCLGVSILVLILVVVLAVVVPRWRQQWSGPGTTKR
FPETVLARCVKYTEIHPEMRHVDCQSVWDAFKGAFISKHPCNITEEDYQPLMKLGTQT
VPCNKILLWSRIKDLAHQFTQVQRDMFTLEDTLLGYLADDLTWCGEFNTSKINYQSCP
DWRKDCSNNPVSVFWKTVSRRFAEAACDVVHVMLNGSRSKIFDKNSTFGSVEVHNLQ
PEKVQTLEAWVIHGGREDSRDLCQDPTIKELESIISKRNIQFSCKNIYRPDKFLQCVKNP
EDSSCTSEI

CD38 Macaca fascicularis/Cynomolgus/Crab eating macaque (Accession AAT36330.1; SEQ ID NO:2)

MANCEFSPVSGDKPCCRLSRRAQVCLGVCLLVLLILVVVVAVVLPRWRQQWSGSGTT
SRFPETVLARCVKYTEVHPEMRHVDCQSVWDAFKGAFISKYPCNITEEDYQPLVKLGT
QTVPCNKTLLWSRIKDLAHQFTQVQRDMFTLEDMLLGYLADDLTWCGEFNTFEINYQ
SCPDWRKDCSNNPVSVFWKTVSRRFAETACGVVHVMLNGSRSKIFDKNSTFGSVEVH
NLQPEKVQALEAWVIHGGREDSRDLCQDPTIKELESIISKRNIRFFCKNIYRPDKFLQCV
KNPEDSSCLSGI

FIG. 4

| BM2 | | BM1 | | Ab19 | | Ab79 | |
|---|---|---|---|---|---|---|---|
| | | | | | | | |
| E | 76 | N | 120 | G | 91 | K | 121 |
| H | 79 | K | 121 | E | 103 | F | 135 |
| E | 104 | F | 135 | E | 104 | Q | 139 |
| Q | 107 | Q | 139 | D | 105 | D | 141 |
| M | 110 | D | 141 | Q | 107 | M | 142 |
| K | 111 | D | 202 | M | 110 | E | 239 |
| L | 112 | V | 203 | K | 111 | W | 241 |
| G | 113 | H | 205 | T | 114 | S | 274 |
| T | 114 | Q | 236 | Q | 115 | C | 275 |
| Q | 115 | T | 237 | T | 148 | K | 276 |
| T | 116 | E | 239 | V | 192 | F | 284 |
| V | 117 | W | 241 | R | 194 | V | 288 |
| C | 119 | Q | 272 | R | 195 | K | 289 |
| T | 148 | F | 273 | F | 196 | N | 290 |
| L | 150 | S | 274 | E | 198 | P | 291 |
| T | 191 | C | 275 | A | 199 | E | 292 |
| V | 192 | K | 276 | H | 228 | D | 293 |
| R | 194 | F | 284 | N | 229 | S | 294 |
| R | 195 | P | 291 | Q | 231 | | |
| F | 196 | E | 292 | E | 233 | | |
| E | 198 | T | 297 | K | 234 | | |
| A | 199 | S | 298 | | | | |
| Q | 231 | | | | | | |
| E | 233 | | | | | | |
| K | 234 | | | | | | |

FIG. 17
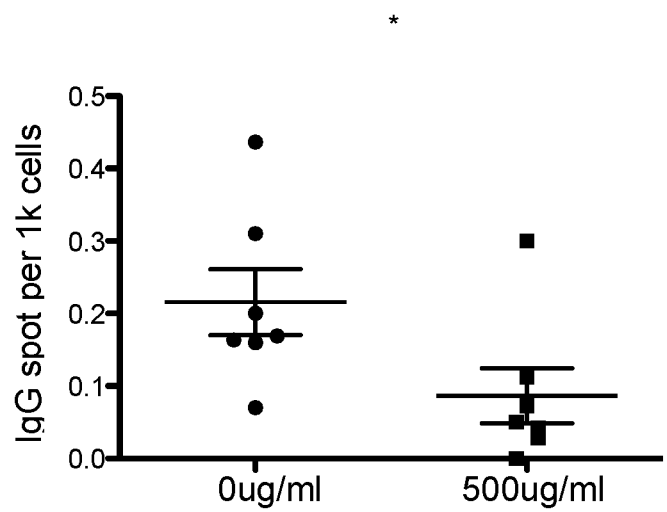
FIG. 17a (Healthy Subject)
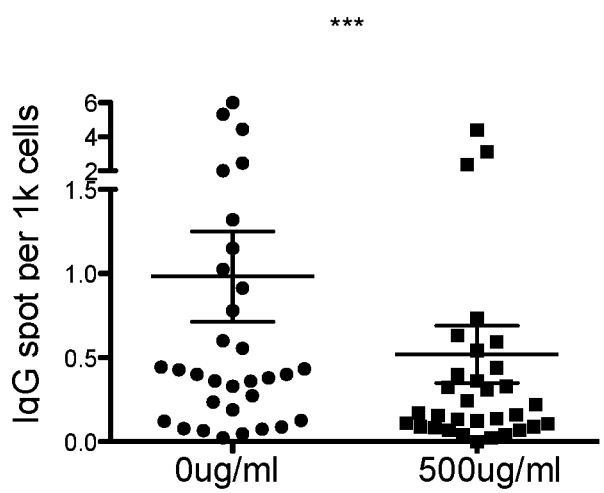
FIG. 17b (SLE Subject)

FIG. 18
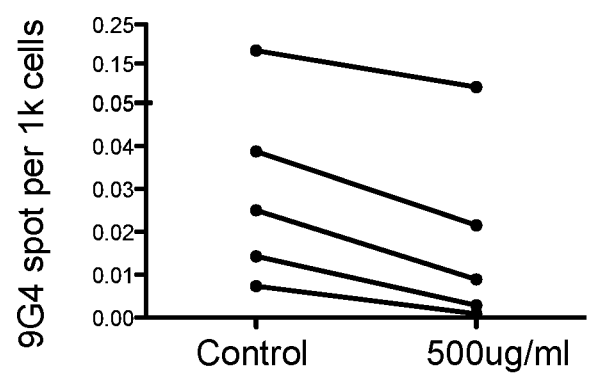
FIG. 18a
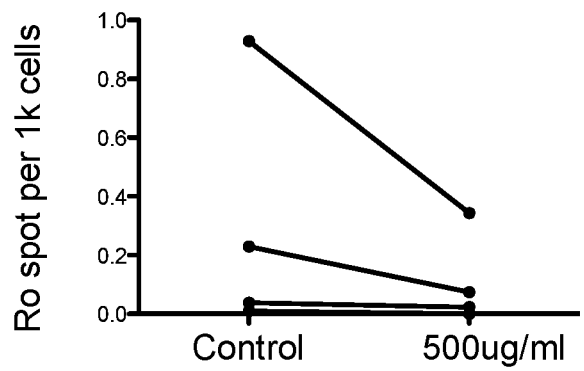
FIG. 18b

SEQUENCE LISTING

```
Sequence total quantity: 35
SEQ ID NO: 1             moltype = AA  length = 300
FEATURE                  Location/Qualifiers
source                   1..300
                         mol_type = protein
                         organism = Homo sapiens
SEQUENCE: 1
MANCEFSPVS GDKPCCRLSR RAQLCLGVSI LVLILVVVLA VVVPRWRQQW SGPGTTKRFP   60
ETVLARCVKY TEIHPEMRHV DCQSVWDAFK GAFISKHPCN ITEEDYQPLM KLGTQTVPCN  120
KILLWSRIKD LAHQFTQVQR DMFTLEDTLL GYLADDLTWC GEFNTSKINY QSCPDWRKDC  180
SNNPVSVFWK TVSRRFAEAA CDVVHVMLNG SRSKIFDKNS TFGSVEVHNL QPEKVQTLEA  240
WVIHGGREDS RDLCQDPTIK ELESIISKRN IQFSCKNIYR PDKFLQCVKN PEDSSCTSEI  300

SEQ ID NO: 2             moltype = AA  length = 301
FEATURE                  Location/Qualifiers
source                   1..301
                         mol_type = protein
                         organism = Macaca fascicularis
SEQUENCE: 2
MANCEFSPVS GDKPCCRLSR RAQVCLGVCL LVLLILVVVV AVVLPRWRQQ WSGSGTTSRF   60
PETVLARCVK YTEVHPEMRH VDCQSVWDAF KGAFISKYPC NITEEDYQPL VKLGTQTVPC  120
NKTLLWSRIK DLAHQFTQVQ RDMFTLEDML LGYLADDLTW CGEFNTFEIN YQSCPDWRKD  180
CSNNPVSVFW KTVSRRFAET ACGVVHVMLN GSRSKIFDKN STFGSVEVHN LQPEKVQALE  240
AWVIHGGRED SRDLCQDPTI KELESIISKR NIRFFCKNIY RPDKFLQCVK NPEDSSCLSG  300
I                                                                  301

SEQ ID NO: 3             moltype = AA  length = 8
FEATURE                  Location/Qualifiers
REGION                   1..8
                         note = Ab79 Heavy Chain CDR1
source                   1..8
                         mol_type = protein
                         organism = synthetic construct
SEQUENCE: 3
GFTFDDYG                                                             8

SEQ ID NO: 4             moltype = AA  length = 8
FEATURE                  Location/Qualifiers
REGION                   1..8
```

```
                        note = Ab79 Heavy Chain CDR2
source                  1..8
                        mol_type = protein
                        organism = synthetic construct
SEQUENCE: 4
ISWNGGKT                                                                8

SEQ ID NO: 5            moltype = AA  length = 16
FEATURE                 Location/Qualifiers
REGION                  1..16
                        note = Ab79 Heavy Chain CDR3
source                  1..16
                        mol_type = protein
                        organism = synthetic construct
SEQUENCE: 5
ARGSLFHDSS GFYFGH                                                       16

SEQ ID NO: 6            moltype = AA  length = 8
FEATURE                 Location/Qualifiers
REGION                  1..8
                        note = Ab79 Light Chain CDR1
source                  1..8
                        mol_type = protein
                        organism = synthetic construct
SEQUENCE: 6
SSNIGDNY                                                                8

SEQ ID NO: 7            moltype =     length =
SEQUENCE: 7
000

SEQ ID NO: 8            moltype = AA  length = 10
FEATURE                 Location/Qualifiers
REGION                  1..10
                        note = Ab79 Light Chain CDR3
source                  1..10
                        mol_type = protein
                        organism = synthetic construct
SEQUENCE: 8
QSYDSSLSGS                                                              10

SEQ ID NO: 9            moltype = AA  length = 135
FEATURE                 Location/Qualifiers
REGION                  1..135
                        note = Ab79 Heavy Chain Variable Region
source                  1..135
                        mol_type = protein
                        organism = synthetic construct
SEQUENCE: 9
EVQLLESGGG LVQPGGSLRL SCAASGFTFD DYGMSWVRQA PGKGLEWVSD ISWNGGKTHY       60
VDSVKGQFTI SRDNSKNTLY LQMNSLRAED TAVYYCARGS LFHDSSGFYF GHWGQGTLVT      120
VSSASTKGPS VFPLA                                                      135

SEQ ID NO: 10           moltype = AA  length = 129
FEATURE                 Location/Qualifiers
REGION                  1..129
                        note = Ab79 Light Chain Variable Region
source                  1..129
                        mol_type = protein
                        organism = synthetic construct
SEQUENCE: 10
QSVLTQPPSA SGTPGQRVTI SCSGSSSNIG DNYVSWYQQL PGTAPKLLIY RDSQRPSGVP       60
DRFSGSKSGT SASLAISGLR SEDEADYYCQ SYDSSLSGSV FGGGTKLTVL GQPKANPTVT      120
LFPPSSEEL                                                             129

SEQ ID NO: 11           moltype = AA  length = 134
FEATURE                 Location/Qualifiers
REGION                  1..134
                        note = Ab19 Heavy Chain
source                  1..134
                        mol_type = protein
                        organism = synthetic construct
SEQUENCE: 11
EVQLLESGGG LVQPGGSLRL SCAASGFTFN NYDMTWVRQA PGKGLEWVAV ISYDGSDKDY       60
ADSVKGRFTI SRDNSKNTLY LQMNSLRAED TAVYYCARVY YYGFSGPSMD VWGQGTLVTV      120
SSASTKGPSV FPLA                                                       134

SEQ ID NO: 12           moltype = AA  length = 130
FEATURE                 Location/Qualifiers
```

```
REGION                         1..130
                               note = Ab19 Light Chain
source                         1..130
                               mol_type = protein
                               organism = synthetic construct
SEQUENCE: 12
QSVLTQPPSA SGTPGQRVTI SCSGSNSNIG SNTVNWYQQL PGTAPKLLIY SDSNRPSGVP    60
DRFSGSKSGT SASLAISGLR SEDEADYYCQ SYDSSLSGSR VFGGGTKLTV LGQPKANPTV   120
TLFPPSSEEL                                                          130

SEQ ID NO: 13                  moltype = AA  length = 8
FEATURE                        Location/Qualifiers
REGION                         1..8
                               note = Ab19 Heavy Chain CDR1
source                         1..8
                               mol_type = protein
                               organism = synthetic construct
SEQUENCE: 13
GFTFNNYD                                                              8

SEQ ID NO: 14                  moltype = AA  length = 8
FEATURE                        Location/Qualifiers
REGION                         1..8
                               note = Ab19 Heavy Chain CDR2
source                         1..8
                               mol_type = protein
                               organism = synthetic construct
SEQUENCE: 14
ISYDGSDK                                                              8

SEQ ID NO: 15                  moltype = AA  length = 15
FEATURE                        Location/Qualifiers
REGION                         1..15
                               note = Ab19 Heavy Chain CDR3
source                         1..15
                               mol_type = protein
                               organism = synthetic construct
SEQUENCE: 15
ARVYYYGFSG PSMDV                                                     15

SEQ ID NO: 16                  moltype = AA  length = 8
FEATURE                        Location/Qualifiers
REGION                         1..8
                               note = Ab19 Light Chain CDR1
source                         1..8
                               mol_type = protein
                               organism = synthetic construct
SEQUENCE: 16
NSNIGSNT                                                              8

SEQ ID NO: 17                  moltype =    length =
SEQUENCE: 17
000

SEQ ID NO: 18                  moltype = AA  length = 11
FEATURE                        Location/Qualifiers
REGION                         1..11
                               note = Ab19 Light Chain CDR3
source                         1..11
                               mol_type = protein
                               organism = synthetic construct
SEQUENCE: 18
QSYDSSLSGS R                                                         11

SEQ ID NO: 19                  moltype = AA  length = 452
FEATURE                        Location/Qualifiers
REGION                         1..452
                               note = Ab19 Heavy Chain
source                         1..452
                               mol_type = protein
                               organism = synthetic construct
SEQUENCE: 19
EVQLLESGGG LVQPGGSLRL SCAASGFTFN NYDMTWVRQA PGKGLEWVAV ISYDGSDKDY    60
ADSVKGRFTI SRDNSKNTLY LQMNSLRAED TAVYYCARVY YYGFSGPSMD VWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
```

```
RWQQGNVFSC SVMHEALHNH YTQKSLSLSP GK                                       452

SEQ ID NO: 20           moltype = AA   length = 217
FEATURE                 Location/Qualifiers
REGION                  1..217
                        note = Ab19 Light Chain
source                  1..217
                        mol_type = protein
                        organism = synthetic construct
SEQUENCE: 20
QSVLTQPPSA SGTPGQRVTI SCSGSNSNIG SNTVNWYQQL PGTAPKLLIY SDSNRPSGVP          60
DRFSGSKSGT SASLAISGLR SEDEADYYCQ SYDSSLSGSR VFGGGTKLTV LGQPKANPTV         120
TLFPPSSEEL QANKATLVCL ISDFYPGAVT VAWKADGSPV KAGVETTKPS KQSNNKYAAS         180
SYLSLTPEQW KSHRSYSCQV THEGSTVEKT VAPTECS                                 217

SEQ ID NO: 21           moltype = AA   length = 453
FEATURE                 Location/Qualifiers
REGION                  1..453
                        note = Ab79 Heavy Chain
source                  1..453
                        mol_type = protein
                        organism = synthetic construct
SEQUENCE: 21
EVQLLESGGG LVQPGGSLRL SCAASGFTFD DYGMSWVRQA PGKGLEWVSD ISWNGGKTHY          60
VDSVKGQFTI SRDNSKNTLY LQMNSLRAED TAVYYCARGS LFHDSSGPYF GHWGQGTLVT         120
VSSASTKGPS VFPLAPSSKS TSGGTAALGC LVKDYFPEPV TVSWNSGALT SGVHTFPAVL         180
QSSGLYSLSS VVTVPSSSLG TQTYICNVNH KPSNTKVDKR VEPKSCDKTH TCPPCPAPEL         240
LGGPSVFLFP PKPKDTLMIS RTPEVTCVVV DVSHEDPEVK FNWYVDGVEV HNAKTKPREE         300
QYNSTYRVVS VLTVLHQDWL NGKEYKCKVS NKALPAPIEK TISKAKGQPR EPQVYTLPPS         360
REEMTKNQVS LTCLVKGFYP SDIAVEWESN GQPENNYKTT PPVLDSDGSF FLYSKLTVDK         420
SRWQQGNVFS CSVMHEALHN HYTQKSLSLS PGK                                     453

SEQ ID NO: 22           moltype = AA   length = 216
FEATURE                 Location/Qualifiers
REGION                  1..216
                        note = Ab79 Light Chain
source                  1..216
                        mol_type = protein
                        organism = synthetic construct
SEQUENCE: 22
QSVLTQPPSA SGTPGQRVTI SCSGSSSNIG DNYVSWYQQL PGTAPKLLIY RDSQRPSGVP          60
DRFSGSKSGT SASLAISGLR SEDEADYYCQ SYDSSLSGSV FGGGTKLTVL GQPKANPTVT         120
LFPPSSEELQ ANKATLVCLI SDFYPGAVTV AWKADGSPVK AGVETTKPSK QSNNKYAASS         180
YLSLTPEQWK SHRSYSCQVT HEGSTVEKTV APTECS                                  216

SEQ ID NO: 23           moltype = AA   length = 318
FEATURE                 Location/Qualifiers
source                  1..318
                        mol_type = protein
                        organism = Homo sapiens
SEQUENCE: 23
MAAQGCAASR LLQLLLQLLL LLLLLAAGGA RARWRGEGTS AHLRDIFLGR CAEYRALLSP          60
EQRNKNCTAI WEAFKVALDK DPCSVLPSDY DLFINLSRHS IPRDKSLFWE NSHLLVNSFA         120
DNTRRFMPLS DVLYGRVADF LSWCRQKNDS GLDYQSCPTS EDCENNPVDS FWKRASIQYS         180
KDSSGVIHVM LNGSEPTGAY PIKGFFADYE IPNLQKEKIT RIEIWVMHEI GGPNVESCGE         240
GSMKVLEKRL KDMGFQYSCI NDYRPVKLLQ CVDHSTHPDC ALKSAAATQ RKAPSLYTEQ         300
RAGLIIPLFL VLASRTQL                                                      318

SEQ ID NO: 24           moltype = AA   length = 122
FEATURE                 Location/Qualifiers
REGION                  1..122
                        note = Benchmark 1 Heavy Chain
source                  1..122
                        mol_type = protein
                        organism = synthetic construct
SEQUENCE: 24
EVQLLESGGG LVQPGGSLRL SCAVSGFTFN SFAMSWVRQA PGKGLEWVSA ISGSGGGTYY          60
ADSVKGRFTI SRDNSKNTLY LQMNSLRAED TAVYFCAKDK ILWFGEPVFD YWGQGTLVTV         120
SS                                                                       122

SEQ ID NO: 25           moltype = AA   length = 108
FEATURE                 Location/Qualifiers
REGION                  1..108
                        note = Benchmark 1 Light Chain
source                  1..108
                        mol_type = protein
                        organism = synthetic construct
SEQUENCE: 25
EIVLTQSPAT LSLSPGERAT LSCRASQSVS SYLAWYQQKP GQAPRLLIYD ASNRATGIPA          60
```

```
RFSGSGSGTD FTLTISSLEP EDFAVYYCQQ RSNWPPTFGQ GTKVEIKR        108

SEQ ID NO: 26           moltype = AA   length = 120
FEATURE                 Location/Qualifiers
REGION                  1..120
                        note = Benchmark 2 Heavy Chain
source                  1..120
                        mol_type = protein
                        organism = synthetic construct
SEQUENCE: 26
QVQLVQSGAE VAKPGTSVKL SCKASGYTFT DYWMQWVKQR PGQGLEWIGT IYPGDGDTGY  60
AQKFQGKATL TADKSSKTVY MHLSSLASED SAVYYCARGD YYGSNSLDYW GQGTSVTVSS 120

SEQ ID NO: 27           moltype = AA   length = 108
FEATURE                 Location/Qualifiers
REGION                  1..108
                        note = Benchmark 2 Light Chain
source                  1..108
                        mol_type = protein
                        organism = synthetic construct
SEQUENCE: 27
DIVMTQSHLS MSTSLGDPVS ITCKASQDVS TVVAWYQQKP GQSPRRLIYS ASYRYIGVPD  60
RFTGSGAGTD FTFTISSVQA EDLAVYYCQQ HYSPPYTFGG GTKLEIKR            108

SEQ ID NO: 28           moltype = AA   length = 449
FEATURE                 Location/Qualifiers
REGION                  1..449
                        note = Ab43 Heavy Chain
source                  1..449
                        mol_type = protein
                        organism = synthetic construct
SEQUENCE: 28
EVQLLESGGG LVQPGGSLRL SCAASGFTFS SYGMHWVRQA PGKGLEWVSR INSDGSSTSY  60
ADSMKGQFTI SRDNSKNTLY LQMNSLRAED TAVYYCARGG YYYYAMDVWG QGTLVTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKRVEPK SCDKTHTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSREEM 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGK                                 449

SEQ ID NO: 29           moltype = AA   length = 216
FEATURE                 Location/Qualifiers
REGION                  1..216
                        note = Ab43 Light Chain
source                  1..216
                        mol_type = protein
                        organism = synthetic construct
SEQUENCE: 29
QSVLTQPPSA SGTPGQRVTI SCSGGSSNIG YKTVNWYQQL PGTAPKLLIY DNNKRPSGVP  60
DRFSGSKSGT SASLAISGLR SEDEADYYCA AWDDSLNGLV FGGGTKLTVL GQPKANPTVT 120
LFPPSSEELQ ANKATLVCLI SDFYPGAVTV AWKADGSPVK AGVETTKPSK QSNNKYAASS 180
YLSLTPEQWK SHRSYSCQVT HEGSTVEKTV APTECS                         216

SEQ ID NO: 30           moltype = AA   length = 455
FEATURE                 Location/Qualifiers
REGION                  1..455
                        note = Ab72 Heavy Chain
source                  1..455
                        mol_type = protein
                        organism = synthetic construct
SEQUENCE: 30
EVQLLESGGG LVQPGGSLRL SCAASGFTFS SYGMNWVRQA PGKGLEWVSG ISGSGGSTYY  60
ADSVKGRFTI SRDNSKNTLY LQMNSLRAED TAVYYCAKDS NYDFWSGYYY GMDVWGQGTL 120
VTVSSASTKG PSVFPLAPSS KSTSGGTAAL GCLVKDYFPE PVTVSWNSGA LTSGVHTFPA 180
VLQSSGLYSL SSVVTVPSSS LGTQTYICNV NHKPSNTKVD KRVEPKSCDK THTCPPCPAP 240
ELLGGPSVFL FPPKPKDTLM ISRTPEVTCV VVDVSHEDPE VKFNWYVDGV EVHNAKTKPR 300
EEQYNSTYRV VSVLTVLHQD WLNGKEYKCK VSNKALPAPI EKTISKAKGQ PREPQVYTLP 360
PSREEMTKNQ VSLTCLVKGF YPSDIAVEWE SNGQPENNYK TTPPVLDSDG SFFLYSKLTV 420
DKSRWQQGNV FSCSVMHEAL HNHYTQKSLS LSPGK                          455

SEQ ID NO: 31           moltype = AA   length = 216
FEATURE                 Location/Qualifiers
REGION                  1..216
                        note = Ab72 Light Chain
source                  1..216
                        mol_type = protein
                        organism = synthetic construct
SEQUENCE: 31
```

```
QSVLTQPPSA SGTPGQRVTI SCSGSSSNIG SKTVSWYQQL PGTAPKLLIY DNNKRPSGVP    60
DRFSGSKSGT SASLAISGLR SEDEADYYCS SYAARSTNII FGGGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                            216

SEQ ID NO: 32           moltype = AA  length = 449
FEATURE                 Location/Qualifiers
REGION                  1..449
                        note = Ab110 Heavy Chain
source                  1..449
                        mol_type = protein
                        organism = synthetic construct
SEQUENCE: 32
EVQLLESGGG LVQPGGSLRL SCAASGFTFS SYGMHWVRQA PGKGLEWVSI IYSGGSTYYA    60
DSVKGRFTIS RDNSKNTLYL QMNSLRAEDT AVYYCARRAT WGGATHDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 33           moltype = AA  length = 216
FEATURE                 Location/Qualifiers
REGION                  1..216
                        note = Ab110 Light Chain
source                  1..216
                        mol_type = protein
                        organism = synthetic construct
SEQUENCE: 33
QSVLTQPPSA SGTPGQRVTI SCSGSSSNIG SNTVNWYQQL PGTAPKLLIY RNNQRPSGVP    60
DRFSGSKSGT SASLAISGLR SEDEADYYCA TWDDSLNGVL FGGGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                            216

SEQ ID NO: 34           moltype = AA  length = 452
FEATURE                 Location/Qualifiers
REGION                  1..452
                        note = Ab119 Heavy Chain
source                  1..452
                        mol_type = protein
                        organism = synthetic construct
SEQUENCE: 34
EVQLLESGGG LVQPGGSLRL SCAASGFTFN NYDMTWVRQA PGKGLEWVAV ISYDGSDKDY    60
ADSVKGRFTI SRDNSKNTLY LQMNSLRAED TAVYYCARVY YYGFSGPSMD VWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 35           moltype = AA  length = 217
FEATURE                 Location/Qualifiers
REGION                  1..217
                        note = Ab19 Light Chain
source                  1..217
                        mol_type = protein
                        organism = synthetic construct
SEQUENCE: 35
QSVLTQPPSA SGTPGQRVTI SCSGSNSNIG SNTVNWYQQL PGTAPKLLIY SDSNRPSGVP    60
DRFSGSKSGT SASLAISGLR SEDEADYYCQ SYDSSLSGSR VFGGGTKLTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECS                            217
```

METHODS AND MATERIALS FOR ASSESSING RESPONSE TO PLASMABLAST- AND PLASMA CELL-DEPLETING THERAPIES

CROSS REFERENCE TO RELATED APPLICATIONS

This application is a divisional of U.S. patent application Ser. No. 16/317,606, filed Jan. 14, 2019, now U.S. Pat. No. 11,613,586, which is a national stage entry under 35 USC 371 of PCT International Application Number PCT/US2017/042128, filed Jul. 14, 2017, which claims priority under 35 U.S.C. § 119 (e) to U.S. Provisional Application Ser. No. 62/362,963 filed on Jul. 15, 2016, the entire disclosures of which are incorporated herein by reference.

INCORPORATION BY REFERENCE OF MATERIAL SUBMITTED ELECTRONICALLY

The instant application contains a Sequence Listing which has been submitted electronically in XML file format and is hereby incorporated by reference in its entirety. Said XML file, created on Feb. 15, 2023, is named 101588-5014-US01_Sequence_Listing.xml and is 47,146 bytes in size.

FIELD

The present disclosure relates to anti-CD38 antibodies and their use as therapeutics and diagnostics. The present disclosure further relates to methods of treating autoimmune diseases, such as systemic lupus erythematosus and rheumatoid arthritis. The present disclosure further relates to diagnostic assay methods for identifying patients having autoimmune diseases for treatment.

BACKGROUND

Plasma cells and plasmablasts are antibody-secreting cells (ASCs) that are important for pathogenic processes associated with systemic lupus erythematosus (SLE) and rheumatoid arthritis (RA). They have been implicated in numerous antibody-driven autoimmune diseases including myasthenia gravis, Sjogrens syndrome, multiple sclerosis (MS) and autoimmune thyroditis. See Jacobi A M, Mei H, Hoyer B F, et al., Ann Rheum Dis (2010) 69(1):305-8; Dorner T, Isenberg D, Jayne D, et al., International Roundtable on B cells as Therapeutic Target for Intervention, Autoimmun Rev (2009) 9(2):82-9; Tipton C M, Fucile C F, Darce J, et al., Nat Immunol (2015) 16(7):755-65; and Cepok S, Rosche B, Grummel V, et al., Brain (2005) 128(Pt 7):1667-76. Plasmablasts are terminally differentiating B cells that are rapidly produced with the majority becoming short-lived effector cells and the minority becoming long-lived plasma cells.

Most B cells express CD20 and are effectively and durably depleted by antibody therapeutics directed against this cell surface protein. See Silverman G J, Arthritis Rheum (2006) 54(8):2356-67. However, some B lineage cells, such as plasmablasts and plasma cells, do not express appreciable amounts of CD20 and are not effectively reduced by direct CD20 depletion. See Silverman 2006. Therefore the ability of CD20-directed drugs to impact this cell population is limited to depleting the CD20+ B cell population that may eventually differentiate into plasmablasts with little effect on already formed plasmablasts and plasma cells. See Silverman G J and Boyle D L, Immunol Rev (2008) 223:175-85.

Clinical studies involving SLE patients have shown that high levels of plasmablasts prior to anti-CD20 treatment correlate with inefficient B cell depletion in the blood. In addition, incomplete depletion of plasmablasts in the blood may have clinical consequences, including faster relapse and reduced survival. See Vital E M, Rawstron A C, Dass S, et al., Arthritis Rheum (2011) 63(3):603-8. Similar findings have been demonstrated for RA patients treated with anti-CD20 monclonal antibodies. See Dass S, Rawstron A C, Vital E M, et al., Arthritis Rheum (2008) 58(10):2993-9; and Owczarczyk K, Lal P, Abbas A R, et al., Sci Transl Med (2011) 3(101):101ra92.

To address these issues, methods have been developed to indirectly monitor plasmblast and plasma cell levels in the blood by evaluating mRNA transcripts expressed primarily in these cell types. See Vital E M, Dass S, Buch M H, et al., Arthritis Rheum (2011) 63(10):3038-47; Streicher K, Morehouse C A, Groves C J, et al., Arthritis Rheumatol (2014) 66(1):173-84; and Owczarczyk, 2011. Using this method, CD20 non-responders were retrospectively identified as those patients with high levels of IgJ (immunoglobulin J chain) enriched in plasmablasts and plasma cells and low levels of FCRL5 (Fc receptor-like 5 protein) which is expressed in CD20+ non-plasmablasts.

This indirect approach is simple and can be utilized in most clinical situations. Blood samples are collected using commonly available sample tubes (e.g. Paxgene tubes) and when stored appropriately have long stability. However, transcript analyses in whole blood does not easily permit direct quantification of the number of plasmablast and plasma cells, and depending on the exclusivity of transcripts evaluated in this cell population, changes in other cell types could influence the results.

Direct measurement of plasmablast and plasma cell levels before or in response to therapies that affect B cells should help avoid this issue. However, plasmablast viability quickly declines after venipuncture. Using current methodologies, monitoring plasmablast levels requires same-day processing, which is challenging to standardize among different clinical sites.

Although plasmablasts and plasma cells do not express appreciable amounts of CD20, these cells, along with NK cells, constitutively express high levels of CD38, as do B cells and T cells, which up regulate CD38 expression upon activation. See Malavasi F, Deaglio S, Funaro A, et al., Physiol Rev (2008) 88(3):841-86. CD38, also known as cyclic ADP ribose hydrolase, is a type II transmembrane glycoprotein with a long C-terminal extracellular domain and a short N-terminal cytoplasmic domain. CD38 is a member of a group of related membrane bound or soluble enzymes, comprising CD157 and Aplysia ADPR cyclase. This family of enzymes has the unique capacity to convert NAD to cyclic ADP ribose or nictotinic acid-adenine dinucleotide phosphate.

Recent studies in humans indicate anti-CD38 mAbs can deplete multiple blood cell types, including plasmablasts and plasma cells.

BRIEF SUMMARY OF THE INVENTION

Anti-CD38 antibodies, when combined with measurement of plasmablasts and/or plasma cells before or during treatment, may be used to treat patients suffering from rheumatoid arthritis, systemic lupus erythematosus or other autoimmune disease, who are unable to reach disease remission with CD20-based therapies or other therapies that do not durably deplete plasmablasts and/or plasma cells.

One aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO: 1), the disease is an autoimmune disease, and the patient was shown to have, prior to treatment with the anti-CD38 antibody, an elevated level of CD38-expressing cells relative to a control subject.

Another aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and the patient was shown to have, following treatment with an anti-CD20 antibody, an elevated level of CD38-expressing cells relative to a control subject.

An additional aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of CD38-expressing cells relative to a control subject.

A further aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of CD38-expressing cells relative to a control subject.

Another aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of plasma cells and plasmablasts relative to a control subject by assaying for free Ig light chains.

An additional aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of plasma cells and plasmablasts relative to a control subject by assaying for free Ig light chains.

Still another aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of in a CD38-expressing cell of a specific mRNA or group of mRNAs relative to a control subject.

A further aspect of the invention provides a method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of total CD38-expressing cell mRNA relative to a control subject.

An additional aspect of the invention provides a method of treating a disease in a patient, the method comprising administering a therapeutically effective amount of a first anti-CD38 antibody to the patient, wherein the first anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of CD38-expressing cells relative to a control subject by flow cytometry.

Another aspect of the invention provides a method of treating a disease in a patient, the method comprising administering a therapeutically effective amount of a first anti-CD38 antibody to the patient, wherein the first anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of CD38-expressing cells relative to a control subject by flow cytometry.

A further aspect of the invention provides a method for assaying CD38-expressing cells in whole blood, the method comprising:
a) obtaining a sample of whole blood from a subject, wherein the sample includes red blood cells, white blood cells, and an anticoagulant;
b) lysing the red blood cells to form a treated sample;
c) freezing the treated sample to a temperature of about −20° C. or less within about 24 hours of obtaining the sample to form a frozen sample;
d) measuring the amount of CD38-expressing cells in the sample within about 72 hours of obtaining the sample, wherein the frozen sample is warmed to room temperature before measuring the amount of CD38-expressing cells.

Provided herein are reagents and methods for binding to CD38 and methods, for treating CD38 associated diseases and detecting CD38 using CD38-specific binding agents including anti-CD38 antibodies.

Accordingly, in some embodiments, an isolated antibody specific for human CD38 (SEQ ID NO:1) and cynomolgus CD38 (SEQ ID NO:2) is described for use in connection with the various aspects of the invention. In some embodiments, the isolated antibodies described herein can be composed of a heavy chain variable region and a light chain variable region, wherein the heavy chain variable region comprises three complementary determining regions (CDRs), described herein as HCDR1, HCDR2, and HCDR3, and wherein the light chain variable region comprises three CDRs, described herein as LCDR1, LCDR2, and LCDR3. The sequences of the CDRs are represented by: HCDR1 (SEQ ID NO:3), HCDR2 (SEQ ID NO:4), HCDR3 (SEQ ID NO:5), LCDR1 (SEQ ID NO:6), LCDR2 (SEQ ID NO:7) and LCDR3 (SEQ ID NO:8).

In other embodiments, the isolated antibody can comprise a heavy chain variable region, wherein the sequence of heavy chain variable region comprises SEQ ID NO:9. In other embodiments, the isolated antibody can comprise a light chain variable region, wherein the sequence of the light chain variable region comprises SEQ ID NO:10. In other embodiments, the heavy chain variable region comprises SEQ ID NO:9 and the light chain variable region comprises SEQ ID NO: 10.

In some embodiments, the isolated antibody can comprise a heavy chain variable region, wherein the sequence of heavy chain variable region comprises SEQ ID NO:9. In other embodiments, the isolated antibody can comprise a light chain variable region, wherein the sequence of the light chain variable region comprises SEQ ID NO:10. In other embodiments, the heavy chain variable region comprises SEQ ID NO:9 and the light chain variable region comprises SEQ ID NO:10. This combination of heavy chain variable region and light chain variable region is referred to as Ab79. In some embodiments, the isolated antibody includes an Fc domain. In other embodiments, the Fc domain is a human Fc domain. In still other embodiments, the Fc domain is a variant Fc domain.

In some embodiments, an isolated antibody specific for human CD38 (SEQ ID NO:1) and cynomolgus CD38 (SEQ ID NO:2) is described for use in connection with the various aspects of the invention. In some embodiments, the isolated antibodies described herein can be composed of six CDRs, wherein each CDR of this antibody can differ from SEQ ID NO:3, SEQ ID NO:4, SEQ ID NO:5, SEQ ID NO:6, SEQ ID NO:7, and SEQ ID NO:8 by 0, 1, or 2 amino acid substitutions.

In other embodiments, an isolated antibody specific for human CD38 (SEQ ID NO:1) and cynomolgus CD38 (SEQ ID NO:2) is described for use in connection with the various aspects of the invention. The isolated antibodies described herein can be composed of a heavy chain variable region and a light chain variable region, wherein the heavy chain variable region comprises three complementary determining regions (CDRs), described herein as HCDR1, HCDR2, and HCDR3, and wherein the light chain variable region comprises three CDRs, described herein as LCDR1, LCDR2, and LCDR3. The sequences of the CDRs are represented by: HCDR1 (SEQ ID NO:13), HCDR2 (SEQ ID NO:14), HCDR3 (SEQ ID NO:15), LCDR1 (SEQ ID NO:16), LCDR2 (SEQ ID NO:17) and LCDR3 (SEQ ID NO:18).

In some embodiments, the isolated antibody can comprise a heavy chain variable region, wherein the sequence of heavy chain variable region comprises SEQ ID NO: 19. In other embodiments, the isolated antibody can comprise a light chain variable region, wherein the sequence of the light chain variable region comprises SEQ ID NO:20. In some embodiments, the isolated antibody can comprise a heavy chain and a light chain, wherein the heavy chain sequence comprises SEQ ID NO:19 and the light chain comprises SEQ ID NO:20.

In other embodiments, the isolated antibody can comprise a heavy chain variable region, wherein the sequence of heavy chain variable region comprises SEQ ID NO: 11. In other embodiments, the isolated antibody can comprise a light chain variable region, wherein the sequence of the light chain variable region comprises SEQ ID NO: 12. In other embodiments, the heavy chain variable region comprises SEQ ID NO: 11 and the light chain variable region comprises SEQ ID NO: 12. This combination of heavy chain variable region and light chain variable region is referred to as Ab19.

In other embodiments, an isolated antibody specific for human CD38 (SEQ ID NO:1) and cynomolgus CD38 (SEQ ID NO:2) is described for use in connection with the various aspects of the invention. The isolated antibodies described herein can be composed of six CDRs, wherein each CDR of this antibody can differ from SEQ ID NO:13, SEQ ID NO:14, SEQ ID NO:15, SEQ ID NO:16, SEQ ID NO:17, and SEQ ID NO:18 by 0, 1, or 2 amino acid substitutions.

In some embodiments, an isolated anti-CD38 antibody is provided that binds specifically to human CD38 (SEQ ID NO:1) and cynomolgus CD38 (SEQ ID NO:2), wherein the antibody binds to human CD38 with a KD of about $10^{-6}$, $10^{-7}$, $10^{-8}$, $10^{-9}$ or more and binds cynomolgus CD38 with a KD of about $10^{-6}$, $10^{-7}$, $10^{-8}$, $10^{-9}$ or more.

In some embodiments, antibodies that compete with Ab79 and/or Ab19 for binding to human CD38 and/or cynomolgus CD38 are provided.

The methods of the present disclosure can be described as embodiments in any of the following enumerated clauses. It will be understood that any of the embodiments described herein can be used in connection with any other embodiment(s) described herein to the extent that the combined embodiments do not contradict one another.

1. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and the patient was shown to have, prior to treatment with the anti-CD38 antibody, an elevated level of CD38-expressing cells relative to a control subject.

2. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and the patient was shown to have, following treatment with an anti-CD20 antibody, an elevated level of CD38-expressing cells relative to a control subject.

3. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of CD38-expressing cells relative to a control subject.

4. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of CD38-expressing cells relative to a control subject.

5. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of CD38-expressing plasmabalst and plasma cells relative to a control subject by assaying for free Ig light chains.

6. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of CD38-expressing cells relative to a control subject by assaying for free Ig light chains.

7. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of at least one gene enriched in a CD38-expressing cell relative to a control subject.

8. A method of treating a disease in a patient, the method comprising administering a therapeutically effective amount of an anti-CD38 antibody to the patient, wherein the anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of at least one gene enriched in a CD38-expressing cell relative to a control subject.

9. The method according to any one of the preceding clauses, wherein the anti-CD38 antibody comprises:
   a) a heavy chain variable region comprising:
      i) a first CDR comprising SEQ ID NO: 3;
      ii) a second CDR comprising SEQ ID NO:4;
      iii) a third CDR comprising SEQ ID NO: 5; and
   b) a light chain variable region comprising:
      i) a first CDR comprising SEQ ID NO: 6;
      ii) a second CDR comprising SEQ ID NO:7;
      iii) a third CDR comprising SEQ ID NO:8.

10. The method according to clause 9, wherein the heavy chain variable region comprises SEQ ID NO:9.

11. The method according to clause 9, wherein the light chain variable region comprises SEQ ID NO:10.

12. The method according to any one of clauses 9 to 11, wherein the heavy chain variable region comprises SEQ ID NO:9 and the light chain variable region comprises SEQ ID NO:10.

13. The method according to any one of clauses 9 to 11, wherein the heavy chain comprises SEQ ID NO:21 and the light chain comprises SEQ ID NO:22.

14. The method according to any one of clauses 1 to 8, wherein the anti-CD38 antibody comprises:
   a) a heavy chain variable region comprising:
      i) a first CDR comprising SEQ ID NO: 13;
      ii) a second CDR comprising SEQ ID NO:14;
      iii) a third CDR comprising SEQ ID NO: 15; and
   b) a light chain variable region comprising:
      i) a first CDR comprising SEQ ID NO: 16;
      ii) a second CDR comprising SEQ ID NO:17;
      iii) a third CDR comprising SEQ ID NO:18.

15. The method according to clause 14, wherein the heavy chain variable region comprises SEQ ID NO: 11.

16. The method according to clause 14, wherein the light chain variable region comprises SEQ ID NO: 12.

17. The method according to any one of clauses 14 to 16, wherein the heavy chain variable region comprises SEQ ID NO:11 and the light chain variable region comprises SEQ ID NO:12.

18. The method according to any one of clauses 14 to 16, wherein the heavy chain comprises SEQ ID NO:34 and the light chain comprises SEQ ID NO:35.

19. The method according to any one of clauses 9 and 14, wherein the anti-CD38 antibody further comprises an Fc domain.

20. The method according to clause 19, wherein the Fc domain is human.

21. The method according to clause 19, wherein the Fc domain is a variant Fc domain.

22. The method according to any one of clauses 1 to 8, wherein the anti-CD38 antibody interacts with at least K121, F135, Q139, D141, E239, W241, C275, K276, F284, P291 and E292 of SEQ ID NO:1.

23. A method of treating a disease in a patient, the method comprising administering a therapeutically effective amount of a first anti-CD38 antibody to the patient, wherein the first anti-CD38 antibody is an isolated antibody which specifically binds human CD38 (SEQ ID NO:1), the disease is an autoimmune disease, and a biological sample obtained from the patient prior to treatment with the anti-CD38 antibody was shown to have an elevated level of CD38-expressing cells relative to a control subject by flow cytometry.

24. A method of treating a disease in a patient, the method comprising administering a therapeutically effective amount of a first anti-CD38 antibody to the patient, wherein the first anti-CD38 antibody is an isolated antibody which specifically binds human CD38 (SEQ ID NO:1), the disease is an autoimmune disease, and a biological sample obtained from the patient following treatment with an anti-CD20 antibody was shown to have an elevated level of CD38-expressing cells relative to a control subject by flow cytometry.

25. The method according to any one of clauses 23 and 24, wherein the CD38-expressing cells were stained with a second anti-CD38 antibody conjugated to a fluorochrome.

26. The method according to clause 25, wherein the second anti-CD38 antibody is the antibody as defined in any one of clauses 14 to 18.

27. The method according to any one of clauses 21 to 24, wherein the first anti-CD38 antibody is the antibody as defined in any one of clauses 9 to 13.

28. The method according to any one of clauses 1 to 27, wherein the autoimmune disease is selected from the group consisting of rheumatoid arthritis, systemic lupus erythematosus, inflammatory bowel disease, ulcerative colitis, graft-versus-host disease, myasthenia gravis, Sjogrens syndrome, multiple sclerosis, and autoimmune thyroditis.

29. The method according to any one of clauses 1 to 27, wherein the autoimmune disease is rheumatoid arthritis.

30. The method according to any one of clauses 1 to 27, wherein the autoimmune disease is systemic lupus erythematosus.

31. A method for assaying CD38-expressing cells in whole blood, the method comprising:
   a) obtaining a sample of whole blood from a subject, wherein the sample includes red blood cells, white blood cells and an anticoagulant;
   b) lysing the red blood cells to form a treated sample;
   c) freezing the treated sample to form a frozen sample, wherein freezing occurs within about 24 hours of obtaining the sample of whole blood from the subject;
   d) measuring the amount of CD38-expressing cells in the sample within about 72 hours of obtaining the sample, wherein the frozen sample is warmed to room temperature before measuring the amount of CD38-expressing cells.

32. The method of clause 31, wherein the frozen sample is maintained at a temperature of about −20° C. or less prior to measuring the amount of CD38-expressing cells.

33. The method according to any one of clauses 1 to 32, wherein the CD38-expressing cells are plasma cells and/or plasmablasts.

34. The method according to any one of clauses 1 to 32, wherein the CD38-expressing cells are plasma cells.

35. The method according to any one of clauses 1 to 32, wherein the CD38-expressing blood cells are plasmablasts.

These and other embodiments, features and potential advantages will become apparent with reference to the following description and drawings.

BRIEF DESCRIPTION OF THE DRAWINGS

FIG. 2 shows the heavy and light chain sequences of Ab79 and Ab19.

FIG. 3 depicts the sequences of human and cynomolgus CD38.

FIG. 4 shows the epitopes of human CD38 that bind to each of the antibodies, Benchmark 1 and 2, Ab19 and Ab79.

FIG. 17 shows sensitivity of ASC to Ab79 in blood of healthy volunteers (FIG. 17a) and SLE subjects (FIG. 17b) as measured by ELISpot.

FIG. 18 shows Ab79 reduces ASC that produce 9G4 (FIG. 18a) and Ro (FIG. 18b) autoantibodies.

DETAILED DESCRIPTION OF THE INVENTION

Overview

Figure 1:
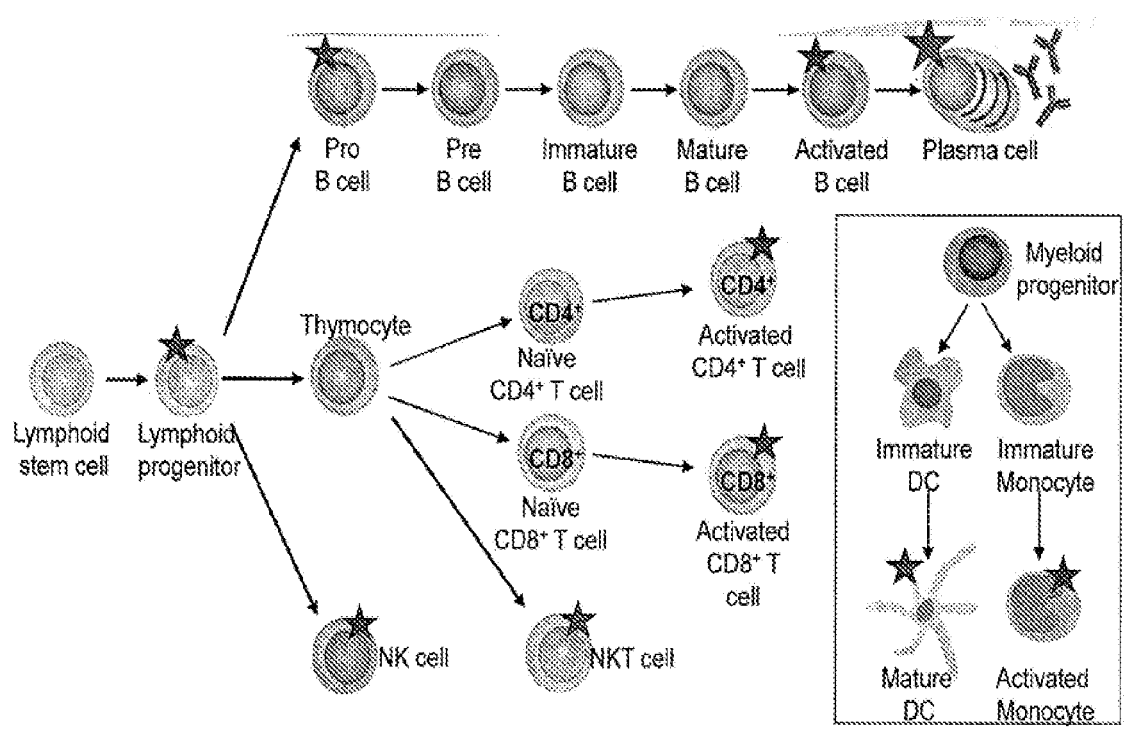
FIG. 1 depicts the CD38 Expression Profile on Lymphoid Lineage Cells, with a star indicating high CD38 expression. CD38 expression has been identified on pro-B cells ($CD34^+$ $CD19^+CD20^-$), activated B cells ($CD19^+CD20^+$), plasma cells ($CD138^+CD19^-CD20^-$), activated $CD4^+$ and $CD8^+$ T cells, NKT cells ($CD3^+CD56^+$) and NK cells ($CD56^+$ $CD16^+$). In addition, CD38 expression is found on lymphoid progenitor cells ($CD34^+CD45RA^+CD10^+CD19^-$) but not the lymphoid stem cell. In addition, increased CD38 expression is seen on mature DCs and activated monocytes.

The extracellular domain of CD38 has been shown to possess bifunctional enzyme activity, having both ADP-ribosyl cyclase as well as ADP-ribosyl hydrolase activities. Thus, CD38 can catalyze the conversion of $NAD^+$ to cADPR (cyclase) and can further hydrolyze it to ADP-ribose (hydrolase). cADPR is involved in the mobilization of calcium from intracellular stores which is a second messenger activity important for cellular proliferation, differentiation, and apoptosis.

Increased expression of CD38 has been documented in a variety of diseases of hematopoietic origin and has been described as a negative prognostic marker in chronic lymphoblastic leukemia. Such diseases include but are not restricted to, multiple myeloma (Jackson et al. (1988)), chronic lymphoblastic leukemia (Moribito et al. (2001), Jelinek et al. (2001), Chevalier et al. (2002), Durig et al. (2002)), B-cell chronic lymphocytic leukemia, acute lymphoblastic leukemia (Keyhani et al (2000)) including B-cell acute lymphocytic leukemia, Waldenstrom macroglobulinemia, primary systemic amyloidosis, mantle-cell lymphoma, pro-lymphocytic/myelocytic leukemia, acute myeloid leukemia (Keyhani et al. (1993)), chronic myeloid leukemia (Marinov et al. (1993)), follicular lymphoma, NK-cell leukemia and plasma-cell leukemia. As such, CD38 provides a useful target in the treatment of diseases of the hematopoietic system.

Several anti-CD38 antibodies are in clinical trials for the treatment of CD38-associated cancers. Accordingly, antibodies to CD38 with therapeutic effect and/or diagnostic applications are useful. The invention provides two different anti-CD38 sets of CDRs that bind to different epitopes of CD38, and which bind both human and cynomolgus forms of CD38, and antibodies that contain these CDRs.

In addition, the present invention shows that anti-CD38 antibodies find use in the diagnosis and/or treatment of inflammation and/or immunological disorders associated with activated lymphocytes, including specifically autoimmune diseases. As shown herein, CD38 is expressed in immature hematopoeitic cells, down regulated in mature cells, and re-expressed at high levels in activated lymphocytes and plasma cells. For example, high CD38 expression is seen in activated B cells, plasma cells, activated CD4+ T cells, activated CD8+ T cells, NK cells, NKT cells, mature dendritic cells (DCs) and activated monocytes.

The findings herein are surprising in that the presence of autoantibodies to CD38 has been associated with diabetes, chronic autoimmune thyroiditis and Graves' disease (see Antonelli et al, Clin. Exp. Immunol. 2001 126:426-431; Mallone et al., Diabetes 50:752 (2001) and Antonelli et al., J. Endocrinol. Invest. 27:695-707 (2004), all of which are incorporated by reference.

Accordingly, the antibodies of the invention find use in the diagnosis and/or treatment of a number of diseases, including, but not limited to autoimmune diseases as discussed below, including but not limited to systemic lupus erthematosus (SLE), rheumatoid arthritis (RA), inflammatory bowel disease (IBD) and ulcerative colitis.

Thus, for example, patients with high plasma cell content can be selected, such as SLE patients who exhibit high plasma cells, as well as RA patients shown to be unresponsive to CD20 based therapies.

The therapeutic anti-CD38 antibodies of the present invention bind to CD38 positive cells, resulting in depletion of these cells, such as activated lymphocytes, through multiple mechanisms of action, including, but not limited to, CDC, ADCC and apoptosis pathways, as outlined herein, leading to the treatment and/or ameoloration of autoimmune diseases.

One advantage, not seen in some of the anti-CD38 antibodies in oncology clinical testing, is the ability to bind to cynomolgus CD38, as these primates find use in preclinical testing, and thus can lead to early evaluation of dosing, toxicity, efficacy, etc.

CD38 Proteins

Accordingly, the present invention provides isolated anti-CD38 antibodies that specifically bind human CD38 protein (and, as described below, additionally and preferably specifically bind primate CD38 protein). As is known in the art, CD38 proteins are found in a number of species. Of particular use in the present invention are antibodies that bind to both the human and primate CD38 proteins, particularly primates used in clinical testing, such as cynomolgus (*Macaca fascicularis*, Crab eating macaque, sometimes referred to herein as "cyno") monkeys. By "human CD38" or "human CD38 antigen" refers to the protein of SEQ ID NO:1 or a functional fraction, such as an epitope, as defined herein. In general, CD38 possesses a short intracytoplasmic tail, a transmembrane domain, and an extracellular domain, in specific embodiments, the antibodies of the invention bind to the extracellular part of the CD38 protein. By "cynomolgus CD38" herein is meant SEQ ID NO:2 which is 92% identical to human CD38.

Synonyms of CD38, include ADP ribosyl cyclase 1, cADPr hydrolase 1, Cd38-rs1, Cyclic ADP-ribose hydrolase 1, 1-19, and NIM-R5 antigen.

In some embodiments, the anti-CD38 Ab79 antibodies of the invention interact with CD38 at a number of amino acid residues including K121, F135, Q139, D141, M142, D202, V203, H205, Q236, E239, W241, S274, C275, K276, F284, C287, V288, K289, N290, P291, E292, D293. As outlined herein, other antibodies that interact with these residues also find use in therapeutic and diagnostic applications.

In some embodiments, the anti-CD38 antibodies of the present invention optionally (and in some cases preferably) do not bind to other members of the CD38 family such as CD157. For example, preferred embodiments herein do not bind to human CD157 of SEQ ID NO:23 (Genbank accession NP_004325).

Antibodies

The present invention provides anti-CD38 antibodies, generally therapeutic and/or diagnostic antibodies as described herein. Antibodies that find use in the present invention can take on a number of formats as described herein, including traditional antibodies as well as antibody derivatives, fragments and mimetics, described below. Essentially, the invention provides antibody structures that contain a set of 6 CDRs as defined herein (including small numbers of amino acid changes as described below).

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of isotypes and/or subclasses.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5$^{th}$ Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)), with the EU number system used for the Fc region.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. For example, as shown herein, the two different antibodies referred to herein as "Ab19" and Ab79" bind to different epitopes on the CD38 molecule.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning", as outlined in the Examples. X-Ray crystallography studies as shown in the Examples has identified the amino acid residues that bind to the antibodies both of the invention (including Ab19 and Ab79) and the prior art (Benchmark 1 and Benchmark 2), as shown in FIG. 4.

In the present invention, Ab79 as outlined in the Examples, interacts with a number of amino acid residues of CD38 including K121, F135, Q139, D141, M142, E239, W241, S274, C275, K276, F284, V288, K289, N290, P291, E292 and D293. It should be noted that these residues are identical in both human and cyno monkeys, with the exception that S274 is actually F274 in cyno. These residues may represent the immunodominant epitope and/or residues within the footprint of the specifically antigen binding peptide.

In the present invention, Ab19 binds to a different epitope, including G91, E103, E1034, D105, Q107, M110, Kill, T114, Q115, T148, V192, R194, R195, F196, A199, H228, N229, Q231, E233 and K234. It should be noted that these residues are identical in both human and cyno monkeys, with the exception that M110 is V110 in cyno and A199 is T199 in cyno.

Thus, in some embodiments, antibodies that compete with Ab79 and Ab19 by binding at either of these epitopes can be used to treat autoimmune diseases. It should be noted that Ab79 and bench mark 1 (BM1) have some overlap; thus antibodies that compete with Ab79 and are not BM1 find use in the present invention.

Thus, the present invention provides antibodies that bind to both human and cyno CD38 and interact with at least 80%, 90%, 95% or 98% of these residues. Stated differently, the surface area of the interaction zone is no more than the area of these residues.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5$^{th}$ edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that still rely In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

Chimeric and Humanized Antibodies

In some embodiments, the antibody can be a mixture from different species, e.g. a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. For instance, an isolated antibody that specifically binds to CD38 is substantially free of antibodies that specifically bind antigens other than CD38.

An isolated antibody that specifically binds to an epitope, isoform or variant of human CD38 or cynomolgus CD38 may, however, have cross-reactivity to other related antigens, for instance from other species, such as CD38 species homologs. Moreover, an isolated antibody may be substantially free of other cellular material and/or chemicals.

Isolated monoclonal antibodies, having different specificities, can be combined in a well defined composition.

Thus for example the Ab79 and Ab19 can be combined in a single formulation, if desired.

The anti-CD38 antibodies of the present invention specifically bind CD38 ligands (e.g. the human and cynomolgus CD38 proteins of SEQ ID NOs:1 and 2. "Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

Antibody Modifications

The present invention further provides variant antibodies. That is, there are a number of modifications that can be made to the antibodies of the invention, including, but not limited to, amino acid modifications in the CDRs (affinity maturation), amino acid modifications in the Fc region, glycosylation variants, covalent modifications of other types, etc.

By "variant" herein is meant a polypeptide sequence that differs from that of a parent polypeptide by virtue of at least one amino acid modification. Amino acid modifications can include substitutions, insertions and deletions, with the former being preferred in many cases.

In general, variants can include any number of modifications, as long as the function of the protein is still present, as described herein. That is, in the case of amino acid variants generated with the CDRs of either Ab79 or Ab19, for example, the antibody should still specifically bind to both human and cynomolgus CD38. Similarly, if amino acid variants are generated with the Fc region, for example, the variant antibodies should maintain the required receptor binding functions for the particular application or indication of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications, with from 1-2, 1-3 and 1-4 also finding use in many embodiments.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 95% or up to 98 or 99% identity to the parent sequences (e.g. the variable regions, the constant regions, and/or the heavy and light chain sequences for Ab79 and/or Ab19). It should be noted that depending on the size of the sequence, the percent identity will depend on the number of amino acids.

By "amino acid substitution" or "substitution" herein is meant the replacement of an amino acid at a particular position in a parent polypeptide sequence with another amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, the parent polypeptides herein are Ab79 and Ab19. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, one or more amino acid modifications are made in one or more of the CDRs of the antibody (either Ab79 or Ab19). In general, only 1 or 2 or 3 amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR can be independently and optionally combined with any other substitution.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155: 1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of Ab79 and Ab19. In addition, as outlined below, amino acid modifications can also independently and optionally be made in any region outside the CDRs, including framework and constant regions.

In some embodiments, variant antibodies of Ab79 and Ab19 that are specific for human CD38 (SEQ ID NO:1) and cynomolgus CD38 (SEQ ID NO:2) is described. This antibody is composed of six CDRs, wherein each CDR of this antibody can differ from SEQ ID NO:3, SEQ ID NO:4, SEQ ID NO:5, SEQ ID NO:6, SEQ ID NO:7, and SEQ ID NO:8 by 0, 1, or 2 amino acid substitutions. In other embodiments, the variant anti-CD38 antibody is composed of six CDRs, wherein each CDR of this antibody can differ from SEQ ID NO:13, SEQ ID NO:14, SEQ ID NO:15, SEQ ID NO:16, SEQ ID NO:17, and SEQ ID NO:18 by 0, 1, or 2 amino acid substitutions.

In some embodiments, the anti-CD38 antibodies of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341, 769, U.S. Pat. Nos. 6,737,056, 7,670,600, 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Glycosylation

Another type of covalent modification is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function. A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent® technology [Biowa, Inc., Princeton, NJ]; GlycoMAb® glycosylation engineering technology [Glycart Biotechnology AG, Zurich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

Specific CDR and Variable Region Embodiments

The present invention provides a number of antibodies each with a specific set of CDRs (including, as outlined above, some amino acid substitutions). As outlined above, the antibodies can be defined by sets of 6 CDRs, by variable regions, or by full-length heavy and light chains, including the constant regions. In addition, as outlined above, amino acid substitutions may also be made. In general, in the context of changes within CDRs, due to the relatively short length of the CDRs, the amino acid modifications are generally described in terms of the number of amino acid modifications that may be made. While this is also applicable to the discussion of the number of amino acid modifications that can be introduced in variable, constant or full length sequences, in addition to number of changes, it is also appropriate to define these changes in terms of the "% identity". Thus, as described herein, antibodies included within the invention are 80, 85, 90, 95, 98 or 99% identical to the SEQ ID NOs listed herein.

In the context of the Ab79 antibody, the set of CDRs is as follows: the three CDRs of the heavy chain encompass HCDR1 SEQ ID NO:3 (HCDR1), SEQ ID NO:4 (HCDR2), and SEQ ID NO:5 (HCDR3), and the three CDRs of the light chain encompass SEQ ID NO:6 (LCDR1), SEQ ID NO:7 (LCDR2), and SEQ ID NO:8 (LCDR3).

In the context of Ab19, the set of CDRs is as follows: HCDR1 (SEQ ID NO:13), HCDR2 (SEQ ID NO:14), and HCDR3 (SEQ ID NO:15), and LCDR1 (SEQ ID NO:16), LCDR2 (SEQ ID NO:17), and LCDR3 (SEQ ID NO:18).

Specifically excluded from the present invention are the antibodies of SEQ ID NOs.: 24 and 25 (the heavy and light chains of Benchmark 1) and SEQ ID NOs.: 26 and 27 (the heavy and light chains of Benchmark 2). It should be noted that these antibodies are not cross reactive with cynomolgus CD38, discussed below.

The antibodies of the invention are cross reactive with human and cynomolgus CD38 and are thus species cross-reactive antibodies. A "species cross-reactive antibody" is an antibody that has a binding affinity for an antigen from a first mammalian species that is nearly the same as the binding affinity for a homologue of that antigen from a second mammalian species. Species cross-reactivity can be expressed, for example, as a ratio of the KD of an antibody for an antigen of the first mammalian species over the KD of the same antibody for the homologue of that antigen from a second mammalian species wherein the ratio is 1.1, 1.2, 1.3, 1.4, 1.5, 2, 5, 10, 15, up to 20. Alternatively or additionally, an antibody is "species cross reactive" when it shows therapeutic or diagnostic efficacy when administered to the second species. Thus, in the present case, the antibodies of the invention are cross reactive with cynomolgus CD38, show preclinical efficacy when administered to cynomolgus primates and thus are considered cross reactive.

In some embodiments, antibodies that compete with the antibodies of the invention (for example, with Ab79 and/or Ab19) for binding to human CD38 and/or cynomolgus CD38 are provided, but are not either BM1 or BM2 are included. Competition for binding to CD38 or a portion of CD38 by two or more anti-CD38 antibodies may be determined by any suitable technique, as is known in the art.

Competition in the context of the present invention refers to any detectably significant reduction in the propensity of an antibody of the invention (e.g. Ab79 or Ab19) to bind its particular binding partner, e.g. CD38, in the presence of the test compound. Typically, competition means an at least about 10-100% reduction in the binding of an antibody of the invention to CD38 in the presence of the competitor, as measured by standard techniques such as ELISA or Biacore® assays. Thus, for example, it is possible to set criteria for competitiveness wherein at least about 10% relative inhibition is detected; at least about 15% relative inhibition is detected; or at least about 20% relative inhibition is detected before an antibody is considered sufficiently competitive. In cases where epitopes belonging to competing antibodies are closely located in an antigen, competition may be marked by greater than about 40% relative inhibition of CD38 binding (e.g., at least about 45% inhibition, such as at least about 50% inhibition, for instance at least about 55% inhibition, such as at least about 60% inhibition, for instance at least about 65% inhibition, such as at least about 70% inhibition, for instance at least about 75% inhibition, such as at least about 80% inhibition, for instance at least about 85% inhibition, such as at least about 90% inhibition, for instance at least about 95% inhibition, or higher level of relative inhibition).

In some cases, one or more of the components of the competitive binding assays are labeled, as discussed below in the context of diagnostic applications.

It may also be the case that competition may exist between anti-CD38 antibodies with respect to more than one of CD38 epitope, and/or a portion of CD38, e.g. in a context where the antibody-binding properties of a particular region of CD38 are retained in fragments thereof, such as in the case of a well-presented linear epitope located in various tested fragments or a conformational epitope that is presented in sufficiently large CD38 fragments as well as in CD38.

Assessing competition typically involves an evaluation of relative inhibitory binding using an antibody of the invention, CD38 (either human or cynomolgus or both), and the test molecule. Test molecules can include any molecule, including other antibodies, small molecules, peptides, etc. The compounds are mixed in amounts that are sufficient to make a comparison that imparts information about the selectivity and/or specificity of the molecules at issue with respect to the other present molecules.

The amounts of test compound, CD38 and antibodies of the invention may be varied. For instance, for ELISA assessments about 5-50 μg (e.g., about 10-50 μg, about 20-50 μg, about 5-20 μg, about 10-20 μg, etc.) of the anti-CD38 antibody and/or CD38 targets are required to assess whether competition exists. Conditions also should be suitable for binding. Typically, physiological or near-physiological conditions (e.g., temperatures of about 20-40° C., pH of about 7-8, etc.) are suitable for anti-CD38:CD38 binding.

Often competition is marked by a significantly greater relative inhibition than about 5% as determined by ELISA and/or FACS analysis. It may be desirable to set a higher threshold of relative inhibition as a criteria/determinant of what is a suitable level of competition in a particular context (e.g., where the competition analysis is used to select or screen for new antibodies designed with the intended function of blocking the binding of another peptide or molecule binding to CD38 (e.g., the natural binding partners of CD38 such as CD31, also called CD31 antigen, EndoCAM, GPIIA, PECAM-1, platelet/endothelial cell adhesion molecule or naturally occurring anti-CD38 antibody).

In some embodiments, the anti-CD38 antibody of the present invention specifically binds to one or more residues or regions in CD38 but also does not cross-react with other proteins with homology to CD38, such as BST-1 (bone marrow stromal cell antigen-1) and Mo5, also called CD157.

Typically, a lack of cross-reactivity means less than about 5% relative competitive inhibition between the molecules when assessed by ELISA and/or FACS analysis using sufficient amounts of the molecules under suitable assay conditions.

Inhibition of CD38 Activity

The disclosed antibodies may find use in blocking a ligand-receptor interaction or inhibiting receptor component interaction. The anti-CD38 antibodies of the invention may be "blocking" or "neutralizing." A "neutralizing antibody" is intended to refer to an antibody whose binding to CD38 results in inhibition of the biological activity of CD38, for example its capacity to interact with ligands, enzymatic activity, signaling capacity and, in particular, it's ability to cause activated lymphocytes. Inhibition of the biological activity of CD38 can be assessed by one or more of several standard in vitro or in vivo assays known in the art (see examples below).

"Inhibits binding" or "blocks binding" (for instance when referring to inhibition/blocking of binding of a CD38 binding partner to CD38) encompass both partial and complete inhibition/blocking. The inhibition/blocking of binding of a CD38 binding partner to CD38 may reduce or alter the normal level or type of cell signaling that occurs when a CD38 binding partner binds to CD38 without inhibition or blocking. Inhibition and blocking are also intended to include any measurable decrease in the binding affinity of a CD38 binding partner to CD38 when in contact with an anti-CD38 antibody, as compared to the ligand not in contact with an anti-CD38 antibody, for instance a blocking of binding of a CD38 binding partner to CD38 by at least about 10%, 20%, 30%, 40%, 50%, 60%, 70%, 80%, 90%, 99%, or 100%.

The disclosed anti-CD38 antibodies may also inhibit cell growth. "Inhibits growth" includes any measurable decrease in the cell growth when contacted with a an anti-CD38 antibody, as compared to the growth of the same cells not in contact with an anti-CD38 antibody, for instance an inhibition of growth of a cell culture by at least about 10%, 20%, 30%, 40%, 50%, 60%, 70%, 80%, 90%, 99%, or 100%.

In some embodiments, the disclosed anti-CD38 antibodies are able to deplete activated lymphocytes, plasmablasts and plasma cells. "Depletion" in this context means a measurable decrease in blood levels (for example as tested in cyno monkeys) of activated lymphocytes and/or plasma cells as compared to untreated animals. In general, depletions of at least about 10%, 20%, 30%, 40%, 50%, 60%, 70%, 80%, 90%, 99%, or 100% are seen. As shown below in the Examples, in addition, one particular advantage that the antibodies of the present invention exhibit is the recoverability of these cells after dosing; that is, as is known for some treatments (for example with anti-CD20 antibodies for example), cell depletion can last for long periods of time, causing unwanted side effects. As shown herein, the effects on the activated lymphocytes and/or plasma cells are recoverable.

Methods for Producing the Antibodies of the Invention

The present invention further provides methods for producing the disclosed anti-CD38 antibodies. These methods encompass culturing a host cell containing isolated nucleic acid(s) encoding the antibodies of the invention. As will be appreciated by those in the art, this can be done in a variety of ways, depending on the nature of the antibody. In some embodiments, in the case where the antibodies of the invention are full length traditional antibodies, for example, a heavy chain variable region and a light chain variable region under conditions such that an antibody is produced and can be isolated.

In general, nucleic acids are provided that encode the antibodies of the invention. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, VA including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are described, for example, in Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Applications and Indications

Once made, the antibodies of the invention find use in a variety of applications, including diagnosis of CD38-related diseases and treatment thereof.

CD38 Related Conditions

In one aspect, the invention provides methods of diagnosing and treating a condition associated with inflammation and immune diseases, particularly diseases associated with activated lymphocytes. As shown herein, CD38 is expressed in immature hematopoeitic cells, down regulated in mature cells, and re-expressed at high levels in activated lymphocytes and plasma cells. For example, high CD38 expression is seen in activated B cells, plasma cells, activated CD4+ T cells, activated CD8+ T cells, NK cells, NKT cells, mature dendritic cells (DCs) and activated monocytes.

The therapeutic anti-CD38 antibodies of the present invention bind to CD38 positive cells, resulting in depletion of these cells, such as activated lymphocytes, through multiple mechanisms of action, including both CDC and ADCC pathways.

Thus, any autoimmune disease that exhibits either increased expression of CD38 or increased numbers of CD38 expressing cells as a component of the disease may be treated using the antibodies of the invention. These include, but are not limited to, allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosus, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

Of particular use in some embodiments are the use of the present antibodies for the use in the diagnosis and/or treatment of a number of diseases, including, but not limited to autoimmune diseases, including but not limited to systemic lupus erthematosus (SLE), rheumatoid arthritis (RA), inflammatory bowel disease (IBD), ulcerative colitis, and graft-v-host disease.

Thus, for example, patients with high plasma cell content can be selected, such as SLE patients who exhibit high plasma cells, as well as RA patients shown to be unresponsive to CD20 based therapies.

It is known in the art that certain conditions are associated with cells that express CD38, and that certain conditions are associated with the overexpression, high-density expression, or upregulated expression of CD38 on the surfaces of cells. Whether a cell population expresses CD38 or not can be determined by methods known in the art, for example flow cytometric determination of the percentage of cells in a given population that are labelled by an antibody that specifically binds CD38 or immunohistochemical assays, as are generally described below for diagnostic applications. For example, a population of cells in which CD38 expression is detected in about 10-30% of the cells can be regarded as having weak positivity for CD38; and a population of cells in which CD38 expression is detected in greater than about 30% of the cells can be regarded as definite positivity for CD38 (as in Jackson et al. (1988), Clin. Exp. Immunol. 72: 351-356), though other criteria can be used to determine whether a population of cells expresses CD38. Density of expression on the surfaces of cells can be determined using methods known in the art, such as, for example, flow cytometric measurement of the mean fluorescence intensity of cells that have been fluorescently labelled using antibodies that specifically bind CD38.

Antibody Compositions for In Vivo Administration

Formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to provide antibodies with other specificities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Administrative Modalities

The antibodies of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Thus for B cell tumors, the subject may experience a decrease in the so-called B symptoms, i.e., night sweats, fever, weight loss, and/or urticaria. For pre-malignant conditions, therapy with an anti-CD38 therapeutic agent may block and/or prolong the time before development of a related malignant condition, for example, development of multiple myeloma in subjects suffering from monoclonal gammopathy of undetermined significance (MGUS).

An improvement in the disease may be characterized as a complete response. By "complete response" is intended an absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or sometimes 6 to 8 weeks, following treatment according to the methods of the invention. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to deplete B-cells may be evaluated in an animal model system predictive of efficacy in human autoimmune diseases.

Alternatively, this property of a composition may be evaluated by examining the ability of the compound to deplete B-cell populations by in vitro assays known to the skilled practitioner. A therapeutically effective amount of a therapeutic compound may deplete B-cell populations, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-CD38 antibodies used in the present invention depend on the disease or condition to be treated and may be determined by the persons skilled in the art.

An exemplary, non-limiting range for a therapeutically effective amount of an anti-CD38 antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, the antibody is administered in a dose of 1 mg/kg or more, such as a dose of from 1 to 20 mg/kg, e.g. a dose of from 5 to 20 mg/kg, e.g. a dose of 8 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the anti-CD38 antibody is administered by infusion in a weekly dosage of from 10 to 500 mg/kg such as of from 200 to 400 mg/kg Such administration may be repeated, e.g., 1 to 8 times, such as 3 to 5 times. The administration may be performed by continuous infusion over a period of from 2 to 24 hours, such as of from 2 to 12 hours.

In one embodiment, the anti-CD38 antibody is administered by slow continuous infusion over a long period, such as more than 24 hours, if required to reduce side effects including toxicity.

In one embodiment the anti-CD38 antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-CD38 antibody.

In a further embodiment, the anti-CD38 antibody is administered once weekly for 2 to 12 weeks, such as for 3 to 10 weeks, such as for 4 to 8 weeks.

In one embodiment, the anti-CD38 antibody is administered by maintenance therapy, such as, e.g., once a week for a period of 6 months or more.

In one embodiment, the anti-CD38 antibody is administered by a regimen including one infusion of an anti-CD38 antibody followed by an infusion of an anti-CD38 antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2,3,4,5,6,7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Diagnostic Uses

The anti-CD38 antibodies provided also find use in the in vitro or in vivo imaging of tumors or autoimmune disease states associated with CD38. In some embodiments, the antibodies described herein are used for both diagnosis and treatment, or for diagnosis alone. When anti-CD38 antibodies are used for both diagnosis and treatment, some embodiments rely on two different anti-CD38 antibodies to two different epitopes, such that the diagnostic antibody does not compete for binding with the therapeutic antibody, although in some cases the same antibody can be used for both. For example, in some instances, the Ab19 antibody is used diagnostically (generally labeled as discussed below) while Ab79 is used therapeutically, or vice versa. Thus included in the invention are compositions comprising a diagnostic antibody and a therapeutic antibody, and in some embodiments, the diagnostic antibody is labeled as described herein. In addition, the composition of therapeutic and diagnostic antibodies can also be co-administered with other drugs as outlined herein.

In many embodiments, a diagnostic antibody is labeled. By "labeled" herein is meant that the antibodies disclosed herein have one or more elements, isotopes, or chemical compounds attached to enable the detection in a screen or diagnostic procedure. In general, labels fall into several classes: a) immune labels, which may be an epitope incorporated as a fusion partner that is recognized by an antibody, b) isotopic labels, which may be radioactive or heavy isotopes, c) small molecule labels, which may include fluorescent and colorimetric dyes (such as fluorescein isothionate, also known as FITC), or molecules such as biotin that enable other labeling methods, and d) labels such as particles (including bubbles for ultrasound labeling) or paramagnetic labels that allow body imagining. Labels may be incorporated into the antibodies at any position and may be incorporated in vitro or in vivo during protein expression, as is known in the art.

Diagnosis can be done either in vivo, by administration of a diagnostic antibody that allows whole body imaging as described below, or in vitro, on a sample or biological sample obtained from a patient. "Sample" or "biological sample" in this context includes any number of things, including, but not limited to, bodily fluids (including, but not limited to, whole blood, blood plasma, urine, serum, lymph, saliva, anal and vaginal secretions, perspiration and semen), as well as tissue samples such as result from biopsies of relevant tissues. In some embodiments, the biological sample is a whole blood sample.

In some embodiments, in vivo imaging is done, including but not limited to ultrasound, CT scans, X-rays, MRI and PET scans, as well as optical techniques, such as those using optical labels for tumors near the surface of the body.

In vivo imaging of diseases associated with CD38 may be performed by any suitable technique. For example, $^{99}$Tc-labeling or labeling with another β-ray emitting isotope may be used to label anti-CD38 antibodies. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993).

In one embodiment, the present invention provides an in vivo imaging method wherein an anti-CD38 antibody is conjugated to a detection-promoting agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient.

For diagnostic imaging, radioisotopes may be bound to an anti-CD38 antibody either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313). In such diagnostic assays involving radioisotope-conjugated anti-CD38 antibodies, the dosage of conjugated anti-CD38 antibody delivered to the patient typically is maintained at as low a level as possible through the choice of isotope for the best combination of minimum half-life, minimum retention in the body, and minimum quantity of isotope, which will permit detection and accurate measurement.

In addition to radioisotopes and radio-opaque agents, diagnostic methods may be performed using anti-CD38 antibodies that are conjugated to dyes (such as with the biotin-streptavidin complex), contrast agents, fluorescent compounds (such as fluorescein isothionate, also known as FITC) or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds.

In order to load an anti-CD38 antibody with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which can be bound chelating groups such as, e.g., porphyrins, polyamines, crown ethers, bisthiosemicarbazones, polyoximes, and like groups known to be useful for this purpose.

Chelates may be coupled to anti-CD38 antibodies using standard chemistries. A chelate is normally linked to an anti-CD38 antibody by a group that enables formation of a bond to the molecule with minimal loss of immunoreactivity and minimal aggregation and/or internal cross-linking.

Examples of potentially useful metal-chelate combinations include 2-benzyl-DTPA and its monomethyl and cyclohexyl analogs, used with diagnostic isotopes in the general energy range of 60 to 4,000 keV, such as $^{125}$I, $^{123}$I, $^{124}$I, $^{62}$Cu, $^{64}$Cu, $^{18}$F, $^{111}$In, $^{67}$Ga, $^{99}$Tc, $^{94}$Tc, $^{11}$C, $^{13}$N, $^{5}$O, and $^{76}$Br, for radio-imaging.

Labels include a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, or other γ-, β-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds.

These and similar chelates, when complexed with non-radioactive metals, such as manganese, iron, and gadolinium may be useful for MRI diagnostic methods in connection with anti-CD38 antibodies. Macrocyclic chelates such as NOTA, DOTA, and TETA are of use with a variety of metals and radiometals, most particularly with radionuclides of gallium, yttrium, and copper, respectively. Such metal-chelate complexes may be made very stable by tailoring the ring size to the metal of interest. Other ring-type chelates such as macrocyclic polyethers, which are of interest for stably binding nuclides, such as $^{223}$Ra may also be suitable in diagnostic methods.

Anti-CD38 antibodies may also be useful in, for example, detecting expression of an antigen of interest in specific CD38-expressing cells, such as plasmablasts and plains cells, tissues, or serum. In some embodiments, the anti-CD38 antibodies described herein can be useful in detecting expression of an antigen of interest in CD38-expressing plasmablasts and plasma cells. For diagnostic applications, the antibody typically will be labeled with a detectable moiety for in vitro assays. As will be appreciated by those in the art, there are a wide variety of suitable labels for use in in vitro testing. Suitable dyes for use in this aspect of the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals"; see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes (including Alexa, phycoerythin, bodipy, and others described in the 6th Edition of the Molecular Probes Handbook by Richard P. Haugland, hereby expressly incorporated by reference Thus, the present invention provides diagnostic anti-CD38 antibody conjugates, wherein the anti-CD38 antibody conjugate is conjugated to a contrast agent (such as for magnetic resonance imaging, computed tomography, or ultrasound contrast-enhancing agent) or a radionuclide that may be, for example, a γ-, β-, α-, Auger electron-, or positron-emitting isotope, or a detectable moiety (such as fluorescein, rhodamine, tetramethylrhodamine, eosin, erythrosin, coumarin, and the like). In some embodiments, the diagnostic anti-CD38 antibody conjugate in connection with the present invention can be an anti-CD38 antibody conjugated to fluorescein isothionate, also known as FITC. In some embodiments, the conjugated anti-CD38 antibody can be referred to as an anti-CD38 antibody-fluorescein conjugate. It will be appreciated by one of skill in the art that other reagents known in the art can be used to conjugate fluorescein to an anti-CD38 antibody, and that in each such instance, the resulting conjugate can be referred to as an anti-CD38 antibody-fluorescein conjugate. Such anti-CD38 antibody-fluorescein conjugates as described herein can be used in in vitro assays such as flow cytometry.

Assay Methods

Applicable assay methods for use in connection with the present invention include, but are not limited to, flow cytometry, assays for free "Ig" light chains, mRNA transcript analysis, and the like. It will be appreciated that any conventional means known in the art for conducting such assay methods may be used in connection with the present invention.

In some embodiments, the methods described herein can be carried out using flow cytometry as a means for quantifying CD38-expressing cells in a biological sample obtained from a patient. It will be appreciated that as used herein, a biological sample obtained from a patient can be a sample of whole blood, a serum sample, or a sample of processed blood. In some embodiments, the biological sample obtained from a patient is a whole blood sample. It will be appreciated that a biological sample obtained from a patient can include one or more types of cells, including but not limited to red blood cells, and any of the cell types shown in FIG. 1. As used herein, "CD38-expressing cells" means any shown to express CD38, including, but not limited to, pro-B cells ($CD34^+CD19^+CD20^-$), activated B cells ($CD19^+CD20^+$), plasmablasts ($CD19^+CD27^+$) long-lived plasma cells ($CD138^+CD19-CD20^-$), short-lived plasma cells ($CD138^+CD19^+CD20^-$), activated $CD4^+$ and $CD8^+$ T cells, NKT cells ($CD3^+CD56^+$) and NK cells ($CD56^+CD16^+$). In addition, CD38 expression is found on lymphoid progenitor cells ($CD34^+CD45RA^+CD10^+CD19^-$) but not the lymphoid stem cell. In addition, increased CD38 expression is seen on mature DCs and activated monocytes.

It will be appreciated that flow cytometry can be carried out by any means known in the art using any applicable flow cytometry instrument. Such methods include conventional means for sample preparation as are commonly known in the art in connection with flow cytometry. In some embodiments, the flow cytometry methods are carried out by staining methods to assist in differentiating cells in a biological sample. It will be appreciated that any staining method commonly known in the art for use in connection with flow cytometry may be used. In some embodiments, one or more labelled antibodies or antibody conjugates are contacted with a whole blood sample as described herein. It is well established in the art that multiple cellular targets can be counted using multicolor flow cytometry. See, for example, Baumgarth, N and Roeder, M, J Immun Methods (2000) 243:77-97. In some embodiments, at least one labelled antibody or antibody conjugate can be used in connection with the flow cytometry methods described herein to identify cells contained in the biological sample obtained from a patient. In some embodiments, at least one labelled antibody or antibody conjugate for use in connection with the flow cytometry methods described herein is an anti-CD38 antibody-fluorescein conjugate. In some embodiments, the anti-CD38 antibody-fluorescein conjugate is Ab19-fluorescein or Ab79-fluorescein.

In some embodiments, the invention provides for a method of conducting a flow cytometry assay comprising contacting a biological sample obtained from a patient with a lysing/fixing solution (also referred to as resuspending), such as FACS™ Lyse solution, comprising at least one component capable of lysing certain cells, such as red blood cells, and at least one component capable of fixing the sample, such as an aldehyde or alcohol. Suitable components in a lysing/fixing solution capable of fixing cells that are useful in connection with the present invention include alcohols, such as methanol or ethanol, which are known to those of skill in the art as precipitating or denaturing fixatives capable of coagulating proteins, or aldehydes, such as formaldehyde or glutaraldehyde. It will be appreciated that formaldehyde can polymerize to paraformaldehyde (PFA), and in the presence of methanol, formaldehyde may not polymerize to paraformaldehyde. It will be further appreciated that, for applications using alcohol-free formaldehyde as a component in the lysing/fixing solution, the lysing/fixing may optionally contain a buffer, such as PBS buffer. In some embodiments, the biological sample is whole blood. In some embodiments, a whole blood sample from a patient can be contacted with a lysing/fixing solution, such as FACS™ Lyse solution, to lyse red blood cells contained in the whole blood sample. (See, Einwallner, E, Subbasic, A, Strasser, A, et al., J Immun Methods (2013) 390:127-132 and Tiirikainen, M. Cytometry (1995) 20:341-348, both of which are incorporated herein by reference). In some embodiments, the biological sample obtained from a patient is contacted with FACS™ Lyse solution to form a treated sample prior to freezing the sample for storage. In some embodiments, the biological sample obtained from a patient is contacted with FACS™ Lyse solution to form a treated sample immediately prior to flow cytometry analysis without freezing the treated sample for storage. In some embodiments, the biological sample obtained from a patient can be contacted with FACS™ Lyse solution for from about 2 minutes to about 30 minutes. In some embodiments, the biological sample can be contacted with FACS™ Lyse solution for from about 4 minutes to about 20 minutes, or from about 5 minutes to about 10 minutes.

In some embodiments, the treated sample obtained after contacting the biological sample obtained from a patient with a lysing/fixing solution, such as FACS™ Lyse solution, is cooled to a temperature of about −20° C. or less to form a frozen sample. In some embodiments, the treated sample is cooled to about −80° C. In some embodiments, the treated sample is cooled to about −78° C. In some embodiments, the treated sample is cooled to about −70° C. In some embodiments, the treated sample is cooled to about −60° C. In some embodiments, the treated sample is cooled to about −50° C. In some embodiments, the treated sample is cooled to about −40° C. In some embodiments, the treated sample is cooled to about −30° C. In some embodiments, the treated sample is cooled to about −20° C. In some embodiments, the treated sample is cooled to between about −80° C. and −20° C. In some embodiments, the treated sample obtained after contacting the biological sample obtained from a patient with a lysing/fixing solution, such as FACS™ Lyse solution, is cooled within about 24 hours or less after the contacting. In some embodiments, the treated sample is cooled within about 12 hours or less after lysing. In some embodiments, the treated sample is cooled within about 6 hours or less.

After the treated sample is frozen, in some embodiments, the frozen sample can be warmed to about room temperature prior to enumerating cells in the biological sample by flow cytometry. In some embodiments, the frozen sample can be warmed to about room temperature within about 78 hours or less after cooling. In some embodiments, the frozen sample can be warned to about room temperature within about 72 hours or less after cooling. In some embodiments, the frozen sample can be warned to about room temperature within about 54 hours or less after cooling. In some embodiments, the frozen sample can be warmed to about room temperature within about 48 hours or less after cooling. In some embodiments, the frozen sample can be warned to about room temperature within about 30 hours or less after cooling. In some embodiments, the frozen sample can be warned to about room temperature within about 24 hours or less after cooling. In some embodiments, the frozen sample can be warned to about room temperature within about 72 hours to about 78 hours after cooling. In some embodiments, the frozen sample can be warned to about room temperature within about 48 hours to about 54 hours after cooling. In some embodiments, the frozen sample can be warned to about room temperature within about 24 hours to about 30 hours after cooling.

In some embodiments, the invention provides a method for assaying CD38-expressing cells in whole blood, the method comprising; obtaining a sample of whole blood from a subject, wherein the sample includes red blood cells and an anticoagulant; lysing the red blood cells to form a treated sample; cooling the treated sample to a temperature of about −20° C. or less within about 24 hours of obtaining the sample to form a frozen sample; and measuring the amount of CD38-expressing cells in the sample within about 72 hours of obtaining the sample, wherein the frozen sample is warmed to room temperature before measuring the amount of CD38-expressing cells.

It will be appreciated that changes in the number of plasmablasts or plasma cells present in a biological sample obtained from a patient can be monitored by assays for free Ig light chains (FLCs). Any assay for free Ig light chains known to one in the art can be used to measure free Ig light chains, such as the FREELIGHT® assay (BindingSite, UK). See, for example, Fassbinder T, Saunders U, Mickholz E, et al., Arthritis Res Ther (2015); Draborg A H, Lydolph M C, Westergaard M, et al., PLoS One (2015) 10(9):e0138753. doi: 10.1371/journal.pone.0138753. eCollection 2015. SLE results in a polyclonal activation of plasma cells, patients have an increase in the kappa and lambda light chains as compared to healthy subjects and this increase in antibodies and plasma cells is considered part of disease pathogenesis (Draborg, 2015). Serum FLC has been reported as marker for SLE and urinary FLC as a marker for Class III/IV lupus nephritis. Serum FLC changes with rituximab or mycophenolate mofetil (MMF) treatment and correlates with other blood plasmablast and plasma cell markers (Fassbinder, 2015; Draborg, 2015).

In some embodiments, the invention provides a method of measuring a biomarker for an elevated expression level of at least one CD38 expressing cell-enriched gene in a biological sample obtained from the patient compared to the expression level of the CD38 expressing cell-enriched gene in a biological sample obtained from a control subject. In some embodiments, the invention provides a method of measuring a biomarker for an elevated expression level of a CD38 expressing cell-enriched gene in a biological sample obtained from the patient compared to a threshold value for the CD38 expressing cell-enriched gene. In certain embodiments, the CD38 expressing cell-enriched gene is IgJ. In certain embodiments, the CD38 expressing cell-enriched gene is CD38, In certain embodiments, the biomarker comprises mRNA In certain embodiments, the biological sample is whole blood. In some embodiments, the patient has received at least one prior treatment. In some embodiments, the at least one prior treatment includes treatment with an anti-CD20 antibody.

In some embodiments, the invention provides a method of predicting the response of a patient to a therapy comprising measuring in a biological sample obtained from the patient the expression of a biomarker for an elevated expression level of at last one CD38 expressing cell-enriched gene and comparing the expression of the at least one CD38 expressing cell-enriched gene in the patient's biological sample to the expression of the same at least one CD38 expressing cell-enriched gene in a. biological sample obtained from a control subject or to a threshold value for the at least one CD38 expressing cell-enriched gene, wherein elevated expression of the at least one CD38 expressing cell-enriched gene in the patient's biological sample compared to the expression in the control subject's biological sample or to the threshold value is predictive of response of the patient to the therapy. In certain embodiments, the plasma cell/plasmablast c-enriched gene is IgJ. In certain embodiments, measuring the expression of at least one gene comprises measuring mRNA. In a further embodiment, measuring mRNA comprises a PCR method, RNA sequencing (RNAseq) or a microarray chip. In certain embodiments, the biological sample comprises whole blood. In some embodiments, the patient has received at least one prior treatment. In some embodiments, the at least one prior treatment includes treatment with an anti-CD20 antibody.

It will be appreciated that the measuring of the expression level of a CD38 expressing cell-enriched gene can be carried out by any conventional means known in the art. For example, the mRNA level can be measured by microarray. In another aspect gene expression is measured by polymerase chain reaction (PCR), RNAseq or real-time quantitative polymerase chain reaction (qPCR). In another aspect, gene expression is measured by multiplex-PCR. According to another embodiment, expression of a gene of interest in a patient's biological sample is considered elevated when compared to that of a control subject's biological sample if the relative mRNA level of the gene of interest in the patient's sample is greater than 2 fold of the level of the control subject's mRNA. According to another embodiment, the relative mRNA level of the gene of interest in the patient's sample is greater than 3 fold, 5 fold, 10 fold, 15 fold, 20 fold, 25 fold, or 30 fold compared to the level in the control subject's sample. In another embodiment, expression of a gene of interest in a patient's biological sample is considered low when compared to that of a control subject's biological sample if the relative mRNA level of the gene of interest in the patient's sample is less than 2 fold of the level of the control subject's mRNA. According to another embodiment, expression of a gene of interest in a patient's biological sample is considered low when compared to that of a control subject's biological sample if the relative mRNA level of the gene of interest in the patient's sample is less than 3 fold, 5 fold, 10 fold, 15 fold, 20 fold, 25 fold, or 30 fold compared to the level in the control subject's sample.

Levels of mRNA may be measured and quantified by various methods well-known to those skilled in the art, including use of commercially available kits and reagents. One such method is polymerase chain reaction (PCR). Another method, for quantitative use, is real-time quantitative PCR, or qPCR. See, e.g., Innis M A et al., eds., Academic Press, Inc. (1990); "Current Protocols in Molecular Biology" (F. M. Ausubel et al., eds., 1987, and periodic updates); and "PCR: The Polymerase Chain Reaction," (Mullis et al., eds., 1994). Another method for quantitative use is RNAseq. See Wang, Zhong; Gerstein, Mark; Snyder, Michael. "RNA-Seq: a revolutionary tool for transcriptomics". Nature Reviews Genetics 10 (1): 57-63.

In another aspect, the gene expression level is measured by a PCR method or a microarray method. In one embodiment, the microarray method comprises the use of a microarray chip having one or more nucleic acid molecules that can hybridize under stringent conditions to a nucleic acid molecule encoding a gene mentioned above. In one embodiment, the PCR method is qPCR. In one embodiment, the PCR method is multiplex-PCR. A microarray is a multiplex technology that typically uses an arrayed series of thousands of nucleic acid probes to hybridize with, e.g, a cDNA or cRNA sample under high-stringency conditions. Probe-target hybridization is typically detected and quantified by detection of fluorophore-, silver-, or chemiluminescence-labeled targets to determine relative abundance of nucleic acid sequences in the target. In typical microarrays, the probes are attached to a solid surface by a covalent bond to a chemical matrix (via epoxy-silane, amino-silane, lysine, polyacrylamide or others). The solid surface is for example, glass, a silicon chip, or microscopic beads. Various microarrays are commercially available, including those manufactured, for example, by Affymetrix, Inc. and Illumina, Inc.

Articles of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLES

The following examples are offered to illustrate, but not to limit the invention.

Example 1: Construction of Expression Vectors Comprising Polynucleotides Encoding Human, Cynomolgus Monkey, and Mouse CD38

To construct a vector expressing human CD38 (huCD38), a polynucleotide encoding huCD38 was isolated from cDNA obtained from Origene Technologies Trueclone® human. The isolated huCD38 was cloned into a stable expression vector (XOMA, Inc.) containing the neomycin resistance (neo$^R$) gene, which allowed for the selection of G418 (Geneticin)-resistant transfectants. The huCD38 gene present in the selected transfectants was sequenced to identify any sequence errors. Errors in the sequence that deviated from Genbank accession NM_001775 were corrected by PCR site-directed mutagenesis. The final vector DNA was confirmed by 5' sequencing.

To construct a vector expressing cynomolgus monkey CD38 (cyCD38), a polynucleotide encoding cyCD38 was isolated from DNA obtained from Biochain Institute's cDNA-monkey (cynomolgus)-normal spleen tissue. The isolated cyCD38 was cloned into a stable expression vector (XOMA, Inc.) containing the neo$^R$ gene, which allowed for the selection of G418 (Geneticin)-resistant transfectants. The cyCD38 gene present in the selected transfectants was sequenced to identify any sequence errors. Errors in the sequence that deviated from Genbank accession AY555148 were corrected by PCR site directed mutagenesis. The final vector DNA was confirmed by sequencing.

To construct a vector expressing mouse CD38 (moCD38), a polynucleotide encoding moCD38 was isolated from DNA obtained from Origene's TrueORF collection. The isolated moCD38 was cloned into a stable expression vector (XOMA, Inc.) containing the neo$^R$ gene, which allowed for the selection of G418 (Geneticin)-resistant transfectants. The moCD38 gene present in the selected transfectants was sequenced to identify any sequence errors. Errors in the sequence that deviated from Genbank accession NM_007646 were corrected by PCR site-directed mutagenesis. The final vector DNA was confirmed by sequencing.

Example 2: Development of CD38 Expressing Chinese Hamster Ovary (CHO) Cells

For development of CHO cells expressing huCD38, muCD38 and cyCD38, CHO cells were transfected with linearized DNA. After one week under selection, the cells were sorted by flow cytometry and the highest huCD38, muCD38 or cyCD38 expressing cells (top 15%) were plated in 96-well plates to generate single colonies. The remaining cells were also plated under selection to generate backup colonies. Approximately 12-14 days after plating, single colonies were identified and transferred to 96-deep-well plates. Clones were screened by FACS analysis after the second passage. Top producing clones were passaged and expanded to shake flasks. The top 2 clones were frozen and/or cultured for mycoplasmal AVA testing and scale-up.

To construct a luciferase reporter for disseminated xenograft models, a commercial vector containing the CMV promoter/luciferase gene/neomycin selectable marker (Promega, Madison, WI) was used to generate stable transfectant line in Daudi Burkitt's lymphoma cells.

Example 3: Phage Display Libraries and Screening of Agents that Bind CD38

Selection of target specific antibody from a phage display library was carried out according to methods described by Marks et al. (2004, Methods Mol. Biol. 248:161-76). Briefly, the phage display library was incubated with 100 pmols of biotinylated CD38 at room temperature for 1 hr and the complex formed was then captured using 100 μL of Streptavidin bead suspension (DYNABEADS® M-280 Streptavidin, Invitrogen). Non-specific phages were removed by washing the beads with wash buffer (5% milk in PBS). Bound phages were eluted with 0.5 ml of 100 nM triethyleamine (TEA) and immediately neutralized by addition of an equal volume of 1M TRIS-CI, pH 7.4. The eluted phage pool was used to infect TG1 $E\ coli$ cells growing in logarithmic phase and phagemid was rescued as described in Marks et al., Id. Selection was repeated for a total of three rounds.

Alternatively, phage display libraries were panned against immobilized CD38 (R&D systems) to identify a panel of antibody fragments with the ability to bind CD38. Panning was carried out using standard protocols (see, e.g., Methods in Molecular Biology, vol. 178: Antibody Phage Display: Methods and Protocols Edited by: P. M. O'Brien and R. Aitken, Humana Press; "Panning of Antibody Phage-Display Libraries," Coomber, D. W. J., pp. 133-145, and "Selection of Antibodies Against Biotinylated Antigens," Chames et al., pp. 147-157). Briefly, three wells of a NUNC® MAXISORP plate were coated with 50 μL of recombinant CD38 (R&D Systems) at a concentration of 10 μg/ml in PBS. After overnight incubation at 4° C., free binding sites were blocked with 5% milk in PBS for one hour at room temperature. Approximately 200 μL of phage library in 5% milk/PBS was then added to the blocked wells and incubated at room temperature for approximately one to two hours. Wells were washed and bound phage was eluted using standard methods (see, e.g., Sam brook and Russell, Molecule Cloning: A Laboratory Manual, $3^{rd}$ Edition, Cold Spring Harbor Laboratory Press, 2001). Eluted phage was amplified via infecting $E.\ coli$ TG 1 host cells in logarithmic growth phase. Infected TG 1 cells were recovered by centrifugation at 2,500 RPM for five minutes, plated onto 15 cm 2YT-ampicillin-2% glucose agar plates, and incubated at 30° C. overnight. The panning process was then repeated using the amplified phage. The cycle of panning, elution, and amplification was repeated for three rounds.

After panning completion, single colonies from the plated TG1 cells were used to inoculate media in 96-well plates. Microcultures were grown to an OD600 of 0.6, at which point expression of soluble scFv was induced by addition of 1 mM IPTG and overnight incubation in a shaker at 30° C. Bacteria were pelleted by centrifugation and periplasmic extract was used to test scFv binding to immobilized CD38 using a standard ELISA assay and a FACS-binding assay.

For FACS binding screen, CHO cells stably expressing CD38 were used to screen scFvs in periplasmic extract (PPE) for their ability to bind native, membrane bound CD38. Parental and CHO transfectants (Human CD38 or Cyno CD38 or Mouse CD38-expressing cell lines) were resuspended separately at $2 \times 10^6$ cells/ml in PBS (Life Technologies), 0.5% BSA (SigmaAldrich), and 0, 1% NaN3 (Sigma-Aldrich) (FACS buffer). Parental CHO cells not expressing CD38 were used as a negative control. Twenty five μL aliquots of the cells were plated in Vbottomed 96-well plates (Costar Cat #3897) and 25 μL of periplasmic extract containing myctagged scFv antibody fragment was added to the cells, then the mixture was incubated at 4° C. for 30 minutes. The cells were then washed twice after which the pellet was resuspended in 25 μL of mouse anti c-myc (1/1000 in FACS buffer)(Roche) and again incubated at 4° C. for 30 minutes. The cells were then washed twice and resuspended in 25 μL of 1/200 dilution anti-mouse IgG-PE in FACS buffer (Jackson labs) and again incubated at 4° C. for 30 minutes. The cells were then washed twice to remove excess unbound antibody and resuspended in 70 μL FACS buffer and analysed on a BD FACScan®. The acquired data was evaluated using FlowJo software (TreeStar, Inc.). Positive samples were identified by comparing the median fluorescence intensity of the CD38 transfected CHO cell relative to the median fluorescence intensity of the parental CHO cell-line (CD38$^-$).

Antibody clones that bound human CD38 were sequenced to identify unique clones. The unique scFV clones were then ranked based on off-rates determined by Biacore® analysis. 200RU to 500RU of human recombinant CD38 (R&D Systems' cat #2404-AC or equivalent) were immobilized by standard amine coupling chemistry (Biacore®) to a CM5 or equivalent chip. A reference spot was also prepared which was activated and then blocked without the immobilization of the protein. This was done by diluting the antigen to 1-3 μg/ml in acetate buffer, pH 5.0, and injecting over the activated surface until required level was immobilized (3-5) minutes. The surface was then blocked with ethanolamine. Periplasmic extracts were diluted one-to-one with the assay running buffer 10 mM HEPES, 150 mM NaCl, 3 mM EDTA (ethylenediaminetetraacetic acid), and 0.05% polysorbate 20 at pH 7.4 with 2 mg/mL BSA (bovine serum albumin)). The diluted periplasmic extract was injected over the surface plasmon resonance (SPR) surfaces at 30 minute for 300 seconds with an additional 900 seconds of dissociation time monitored. Regeneration was with a single 8-second injection of 100 mM HCl. Data from the refer~nce sp,pts were subtracted from the data from the active surface, then dissociation curves were fit using the 1:1 dissociation model in the Biacore® T100 software.

Top-ranking scFV clones were converted to IgG1 antibodies. The FACS binding screen was repeated on the IgG1 reformatted clones using parental CHO cells and CHO cells expressing human, murine and cynomolgus CD38 to ensure binding properties were retained and to assess species cross-reactivity. FACS characterization of IgG-reformatted clones was conducted as described above, but the steps consisting of the addition of anti-c-myc antibody and anti-mouse IgG-PE were replaced by a single step in which binding of full-length human IgG was detected by the addition of phycoerythrin conjugated anti-human IgG (Jackson Labs).

Example 4: In Vitro Cell-Based Assays of IgG-Reformatted Clones

About 150 clones were reformatted as human IgG1 antibodies and five (Ab19, Ab43, Ab72, Ab79, and Ab110) were fully evaluated using a panel of assays, as described below. Performance of IgG-reformatted clones in both in vitro and in vivo assays was compared to two antibodies, BMTK4-1 (also called benchmark-1, BM-1, or BMTK-1) (SEQ ID NOs:24 and 25; heavy and light chain variable regions) and BMTK4-2 (also called benchmark-2, BM-2, or BMTK-2) (SEQ ID NOs: 26 and 27; heavy and light chain variable regions), the amino acid sequences of which were derived from the sequences of known anti-CD38 antibodies daratumumab (also called HuMax-CD38, disclosed in International Publication No. WO 06/099875) and SAR650984 (disclosed in International Publication No. WO 08/047242), respectively. Palivizumab (SYNAGIS®) (MedImmune), a clinically approved antibody that recognizes respiratory syncytial virus served as a negative control for CD38 binding.

Example 5: Detection of Ab79 Binding by Immunofluorescence

Alexa Fluor®-488 dye labeled Ab79 was applied to frozen sections of normal human colorectal tissue, prostate, and lymph. Alexa Fluor®-488 dye labeled Palivizumab (Synagis®) served as a negative staining control. The resulting immunofluorescent images are shown in FIG. 4. The staining pattern observed for Ab79 was identical to that seen with a commercially available polyclonal anti-CD38 antibody on normal human colorectal tissue, prostate and lymph node (data not shown).

Alexa Fluor®-488 dye labeled Ab79 was also applied to normal and multiple myeloma bone marrow specimens (data not shown). Whereas Ab79 bound to ~ 10% of the cells from normal bone marrow, >90% of the multiple myeloma bone marrow cells, in 4 out of 4 tested samples, showed Ab79 binding.

The ability of Ab79 to bind to a number of cell lines (MOLP-8, DAUDI, RPMI, and MCF7) was also examined. MOLP-8 (human multiple myeloma), DAUDI (lymphoblast derived from a patient with Burkitt's lymphoma), and RPMI (cell line established from patient with chronic myelogenesis leukemia) cells all showed binding by Ab79. The breast cancer line, MCF7, appeared largely negative for Ab79 binding (data not shown).

The Alexa Fluor® 488-conjugated antibodies were stained on 8 μm cryostat frozen sections, which were fixed in an ethanol/acetone mixture for 5 min followed by incubation with the antibodies for 1 hour at room temperature in a humidity-controlled chamber. The sections were then washed, a DAPI containing mountant (Vector Laboratories, cat #H1500) was added, and a coverslip was applied.

Example 6: Evaluation of Ab79 Expression on Multiple Myeloma (MM) and Chronic Lymphocytic Leukemia (CLL)

Ab79 binding to bone marrow samples from multiple myeloma patients was analyzed by flow cytometry either after enrichment for CD138' cells or by gating on CD138$^+$ CD45$^{-/lo}$ cells (FIG. 7A). Ab79 was found to be expressed on >95% of cells from four out of six multiple myeloma samples. The binding pattern of Ab79 appeared largely similar to that of an anti-CD38 antibody used in clinical laboratories. Further, Ab79 bound cells from patients with chronic lymphocytic leukemia (FIG. 7B).

In order to measure Ab79 binding to MM and CLL by FACS patient samples were processed within 24 hours. Peripheral blood mononuclear cells were isolated by Ficoll-Paque™ (GE Healthcare) according to the manufacturer's instructions. Expression analysis was performed using the following panels of antibodies with clones in parentheses. MM panel: Ab79-Alexa Fluor®-488, CD45-PerCP(2D1), CD138-APC (MI15). CLL panel: Ab79-Alexa Fluor®-488; CD5-PE (UCHT2), CD45-PerCP(2D1), CD19-APC (SJ25C1). 5 μL of the PE, PerCP, or APC labeled antibody or 10 μL of Alexa Fluor®-488 labeled antibody or isotype control was added to each well or tube containing either 100 μL of 0.2×106 PBMCs or CD138 enriched cells from bone marrow aspirate. samples were incubated for 30 mins at room temperature following which red blood cells were lysed using BD Pharmlyse, according to the manufacturer's instructions. All samples were washed three times in FACS buffer. Samples were fixed in 1% paraformaldehyde and analyzed on a BD FACSCanto™ II or BD FACSCaliber™.

Example 7: Anti-CD38 Induced CDC Assays

Cynomolgus cross-reactive clones were tested for the ability to induce complement-dependent cytotoxicity (CDC). MOLP-8 cells were plated at a density of 10,000 cells per well in a black 96-well flat-bottom tissue culture plate in 50 μL of complete media (RPMI supplemented with 10% fetal bovine serum). 50 μL of 2× anti-CD38 antibody, control IgG antibody, or media alone was added to each well and left to incubate at room temperature for 10 min. Varying amounts (2-15 μL) of purified rabbit complement (cat #CL 3441 Cedarlane Laboratories, Canada), depending upon the cell line was added to each well except control wells. After one hour incubation at 37° C., plates were brought to room temperature, 100 μL of cell titer CytoTox Glo™ reagent (Promega G7571/G7573) was added per well, the plate shaken for 5 to 7 min and luminescence read on an EnVision® (Perkin Elmer) luminescence plate reader. Conditions tested: cells alone; cells+complement; cells+IgG control+complement; cells+antibody+complement. % CDC was calculated using the following equation:

$$100 - (RLU_T/RLU_C) \times 100),$$

where $RLU_T$ is the relative luminescence units of the test sample and $RLU_C$ is the relative luminescence units of the sample with complement alone. Statistical analysis was performed using PRISM software. $EC_{50}$ values, as determined from plots of % CDC versus antibody concentration, are shown in Table 1.

Example 8: Anti-CD38 Induced ADCC Assays

Antibody-dependent cell-mediated cytotoxicity (ADCC) was assessed using Daudi, MOLP-8, and RPMI-8226 cell lines as target cells. PBMCs were isolated as effector cells by Ficoll-Plaque™ separation from buffy coat or LRS which were obtained from the Stanford Blood Center (Palo Alto, CA). Specimens were diluted 1:3 with 2% FBS in PBS. 15 mL of Ficoll-Plaque™ (GE Healthcare) was gently layered under 35 mL of diluted specimen and centrifuged at 1800 rpm (brake off) for 25 min. The cloudy interphase containing PBMCs was collected, washed 3 times in 2% FBS in PBS and frozen aliquots of 50×106 cells/mL per aliquot in 10% DMSO/FBS. Frozen aliquots of PBMCs were thawed and cultured overnight in 10% FBS/RPMI+5 ng/mL recombinant human IL2 (R & D systems #202-IL) at 2×106 per mL, when needed.

For the ADCC assay, all steps were performed in complete media. 5000 target cells were plated per well in a 96-well plate in 50 μL of 3× anti-CD38, control IgG, or media alone was added followed by 50 μL of human effector PBMCs at a ration of between 1:25 to 1:50 target:effector (T:E) cells. Plates were briefly centrifuged for ~ 30 seconds at 800 rpm to bring all cells into close proximity. After 4 hrs at 37° C., plates were centrifuged at 1100 rpm for 5 min and 100 μL supernatant transferred to a white plate. 100 μL CytoTox Glo™ reagent (Promega cat #G9292) was added to the supernatant and plates were left to shake for 20-30 mins at RT. Luminescence was read on an EnVision® (Perkin Elmer) luminescence plate reader and percent specific lysis was calculated using the following equation:

$(RLU_T/RLU_{E/T})/(RLU_L/RLU_{E/T}) \times 100$ where $RLU_T$ is the relative luminescence units of the test sample and $RLU_{E/T}$ is the relative luminescence units of the sample containing target cells and effector cells alone, and $RLU_L$ is the relative luminescence units for cells lysed with Triton X-100. Statistical analysis was performed using PRISM software. $EC_{50}$ values, as determined from plots of % specific lysis versus antibody concentration, are shown in Table 1.

TABLE 1

| | CDC, ADCC, and Agonist Activity for IgG-Reformatted Antibodies | | | | |
|---|---|---|---|---|---|
| Antibody | CDC EC50 nM (MOLP-8) | ADCC EC50 nM (DAUDI) | ADCC EC50 nM (MOLP-8) | ADCC EC50 nM (RPMI-8226) | Apoptosis EC50 nM (DAUDI) |
| BM-1 | 0.48 ± 0.16 | 0.03 ± 0.02 | 0.036 ± 0.013 | 0.13 ± 0.03 | 0.057 |
| BM-2 | 0.65 ± 0.18 | 0.04 ± 0.02 | 0.024 ± 0.005 | 0.15 ± 0.04 | 0.062 |
| Ab19 | 0.98 ± 0.26 | 0.08 ± 0.03 | 0.038 ± 0.008 | 0.46 ± 0.15 | 0.032 |
| Ab43 | 2.2 | 0.12 ± 0.09 | 0.027 ± 0.018 | 3.84 ± 1.34 | 1.56 |
| Ab72 | 0.66 ± 0.49 | 0.14 ± 0.12 | 0.193 ± 0.037 | 2.35 ± 0.99 | 0.35 |
| Ab79 | 1.1 ± 0.39 | 0.03 ± 0.02 | 0.047 ± 0.012 | 0.46 ± 0.19 | 0.048 |
| Ab110 | 1.99 ± 0.71 | 0.24 ± 0.17 | 0.874 ± 0.804 | 2.98 ± 0.91 | 0.40 |
| Ab164 | 2.00 ± 0.83 | ND | 0.165 ± 0.154 | 1.2 ± 0.24 | 0.31 |

Example 9: Affinity Determination by FACS

MOLP-8 cells expressing CD38 were suspended in 1% FBS buffer at a viable cell concentration of approximately 2 million cells/mL. mAbs to be tested were serially diluted (2-fold) across wells over two 96-well plates in 1×PBS. The last well of each titration contained buffer only. Additional PBS and cell suspensions were added to each well so that the final volume was 300~L/well and each well contained approximately 100,000 cells. The mAbs are listed below with the corresponding final mAb binding site concentration (2× molecular concentration) range used for the titrations:
 Benchmark 1, [mAb]bindingsite=50.8 nM-49.7 pM;
 Benchmark 2, [mAb]bindingsite=49.5 nM-48.3 pM;
 Ab 43, [mAb]binding site=49.3 nM-48.2 pM;
 Ab 110, [mAb]bindingsite=204 nM-49.9 pM;
 Ab 79, [mAb]binding Site=103 nM-25.3 pM;
 Ab 72, [mAb]binding Site=103 nM-25.2 pM;
 Ab 19, [mAb]bindingsite=100 nM-12.2 pM;

The plates were placed into a plate shaker for 5 hours at 4° C., after which the plates were washed 3 times at 4° C. with 1×PBS. 200 μl of 99 nM Cy5 goat anti-human IgG Fc specific polyclonal antibody (Jackson ImmunoResearch Laboratories, #109-175-008) was then added to each well, and the plates were shaken for 30 minutes at 4° C. The plates were again washed 2× at 4° C. with 1×PBS, then a FACSCanto™ II HTS flow cytometer was used to record the mean fluorescence intensity (MFI) of 5000 events for each well containing a unique mAb binding site concentration. A plot of the Mean Fluorescence Intensity as a function of the antibody binding site concentration was fit nonlinearly with Scientist 3.0 software using the equation below to estimate KD:

$F = p[(KD+LT+n(M))-\{(KD+LT+n(M))2-4n(M)(LT)\}1/2]/2+B$ where F (mean fluorescence intensity), LT (total mAb binding site concentration), p (proportionality constant that relates arbitrary fluorescence units to bound mAb), M (cellular concentration in molarity; 0.553 fM based on 100,000 cells in 300 μl), n (number of receptors per cell), B (background signal), and KD=equilibrium dissociation constant.

For each antibody titration curve, an estimate for KD was obtained as P, n, B, and KD were floated freely in the nonlinear analysis. For a detailed derivation of the above equation, see Drake and Klakamp (2007), "A rigorous multiple independent binding site model for determining cell-based equilibrium dissociation constants," J. Immunol. Methods 318: 157-62, which is incorporated by reference herein. Table 3 lists the resulting KD's for all antibodies in order of decreasing affinity along with the 95% confidence interval of each fit in parentheses. The antibody binding site concentration (2× the molecular concentration) was used for the nonlinear curve-fitting.

Example 10: Affinity Determination by Biacore®

The affinity of IgG antibodies to soluble CD38 ectodomain (ECD) was determined by surface plasmon resonance (SPR) analysis on a Biacore™ A100 at 22° C. Goat anti-human IgG polyclonal antibody (Caltag H10500) was immobilized to a CM5 biosensor chip using standard amine coupling to spots 1, 2, 4, and 5 within all four flow cells of the chip. Immobilization levels on each spot ranged from 5865 RU to 6899 RU. Human CD38 was obtained from R&D Systems (Cat #2404-AC, Lot #PEH020812A). The stock concentration for CD38 was determined using methods detailed in Pace et al. (1995) "How to measure and predict molar absorption coefficient of a protein" Protein Science 4(11):2411-23 and Pace and Grimsley (2004) "Spectrophotometric determination of protein concentration," in Current Protocols in Protein Science, Chapter 3: Unit 3.1, the teaching of each reference being incorporated by reference herein.

Running buffer was prepared by degassing HEPES-buffered saline, 0.005% polysorbate 20, and adding filtered BSA to a final concentration of 100 μg/mL. All eight purified mAbs were diluted to approximately 2 μg/mL with running buffer. Preliminary experiments estimated the amount of each mAb to be captured in order to maintain a surface capacity ($R_{max}$) no greater than ~100 RU. For each mAb capture/antigen injection cycle, a mAb was captured over spots 1 and 5 within each flow cell with juxtaposed spots 2 and 4 serving as the respective reference surfaces. Each diluted mAb was captured for 1 minute at a flow rate of 10 µL/min followed by three minutes of flowing running buffer for surface stabilization. HuCD38 was injected over all four flow cells for 120 seconds at 30 µL/min over a concentration range of 193.7 nM-3.0 nM (2× serial dilution) followed by a 15 minute dissociation phase. The samples were all prepared in the running buffer and were randomly injected in triplicate with seven buffer injections interspersed for double referencing. The surfaces were regenerated with two 20 second pulses of 10 mM glycine, pH 1.7.

All sensorgram data were processed with Scrubber 2.0c software and globally fit to a 1:1 interaction model in Scrubber 2.0c. The resulting binding constants are shown in Table 2.

TABLE 2

| Antibody | FACS KD (nM) MOLP-8 | FACS KD (pM) RPMI-8226 | Biacore Ka (M−1s−1) | Biacore Kd (s−1) | Biacore KD (nM) |
|---|---|---|---|---|---|
| BM-1 | 1.1 (0.9) | 802 | $4.49 \times 10^4$ | $2.46 \times 10^{-3}$ | 54.8 |
| BM-2 | 1.6 (0.6) | 428 | $4.24 \times 10^5$ | $2.27 \times 10^{-3}$ | 5.4 |
| Ab19 | 0.4 (0.3) | — | $1.54 \times 10^5$ | $8.10 \times 10^{-4}$ | 5.3 |
| Ab79 | 1.2 (1.1) | 508 | $1.22 \times 10^5$ | $6.75 \times 10^{-4}$ | 5.5 |
| Ab72 | 0.6 (0.4) | — | $1.44 \times 10^4$ | $1.82 \times 10^{-3}$ | 126 |
| Ab110 | 1.0 (0.1) | — | $1.22 \times 10^5$ | $1.71 \times 10^{-1}$ | 1400 |
| Ab43 | 1.1 (0.3) | — | $2.72 \times 10^5$ | $1.46 \times 10^{-1}$ | 537 |
| Ab164 | 1.4 (0.7) | — | $1.99 \times 10^5$ | $7.15 \times 10^{-2}$ | 359 |

Example 11: Immunofluorescence Internalization Assays

Immunofluorescence techniques were used to evaluate the internalization of anti-CD38 antibodies into MOLP-8 cells. MOLP-8 cells were collected and $5 \times 10^6$ cells were stained for 10 min at 4° C. in RPMI-1640 with 1 µg of each anti-CD38 antibody directly conjugated to Alexa Fluor® 488. The cells were washed in PBS containing 1% BSA, and $1 \times 10^6$ cells were incubated for 3 or 6 hours at 4° C. or 37° C. Surface staining was quenched for 30 min at 4° C. using 2 µg of rabbit anti-Alexa Fluor®-488 antibody (Invitrogen). The cells were washed and fixed in PBS with 1% PFA, transferred to a Microtest 96-well plate (BD Biosciences), and either evaluated by flow cytometry using a FACSCanto™ II (BD Biosciences) flow cytometer or imaged using an ImageXpress® Micro (Molecular Devices) at 20× magnification.

Example 12: Epitope Binning by Biacore®

Biacore® A100 instrumentation was used to bi~ the two benchmark antibodies as well as Ab 19 and Ab 79. The antibodies were first immobilized at high and low densities on a CM5 chip using NHS/EDC coupling chemistry. For each cycle of the epitope binning experiment, CD38 was first injected over these surfaces. Analogous to a sandwich assay in an ELISA format, a unique antibody (taken from the set of immobilized antibodies) was then injected over surfaces containing CD38/antibody complexes. Surfaces were regenerated using pulses of phosphoric acid at the end of each cycle. Data was collected at 22° C. using HBS-P (10 mM HEPES pH 7.4, 150 mM NaCI, 0.005%) P-20) supplemented with BSA. The resulting sensorgrams were processed using the "Epitope Mapping" module in the Biacore® A100 Evaluation software package as well as a trial version of Scrubber for A100 data sets. Replicate data was used to generate a binary 4×4 matrix for the above 4 mAbs from two separate experiments, as shown in Table 3.

TABLE 3

|  | Ab79 | BM1 | Ab19 | BM2 |
|---|---|---|---|---|
| Ab79 | 0 | 0 | 1 | 1 |
| BM1 | 0 | 0 | 1 | 0 |
| Ab19 | 1 | 1 | 0 | 0 |
| BM2 | 1 | 0 | 0 | 0 |

Example 13: In Vivo Analysis in Oncology

Figure 8:
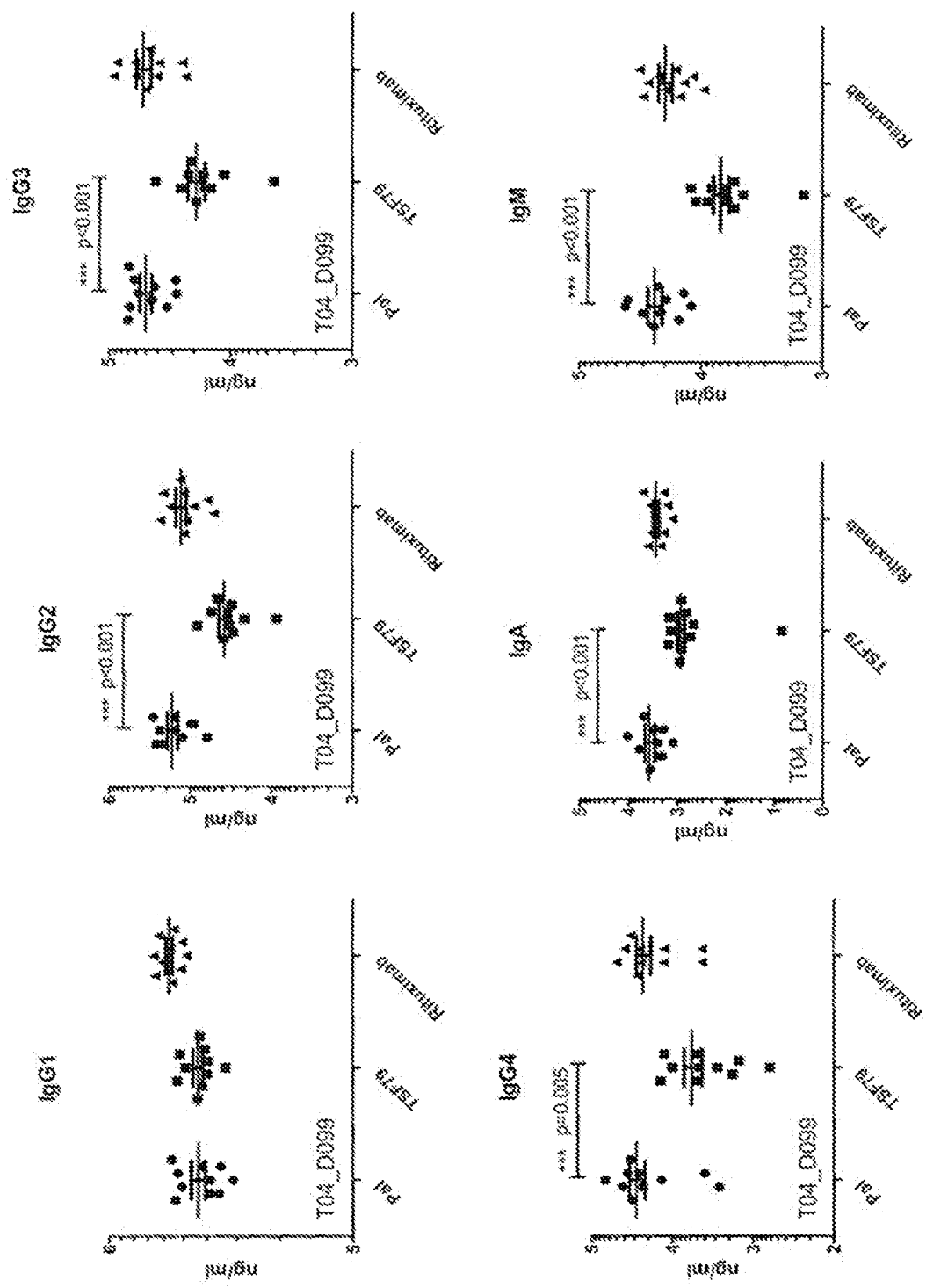
FIG. 8 shows the results from a single HuSCID mouse in terms of significant reductions of all Ig isotypes after a single dose of Ab79.
Figure 9:
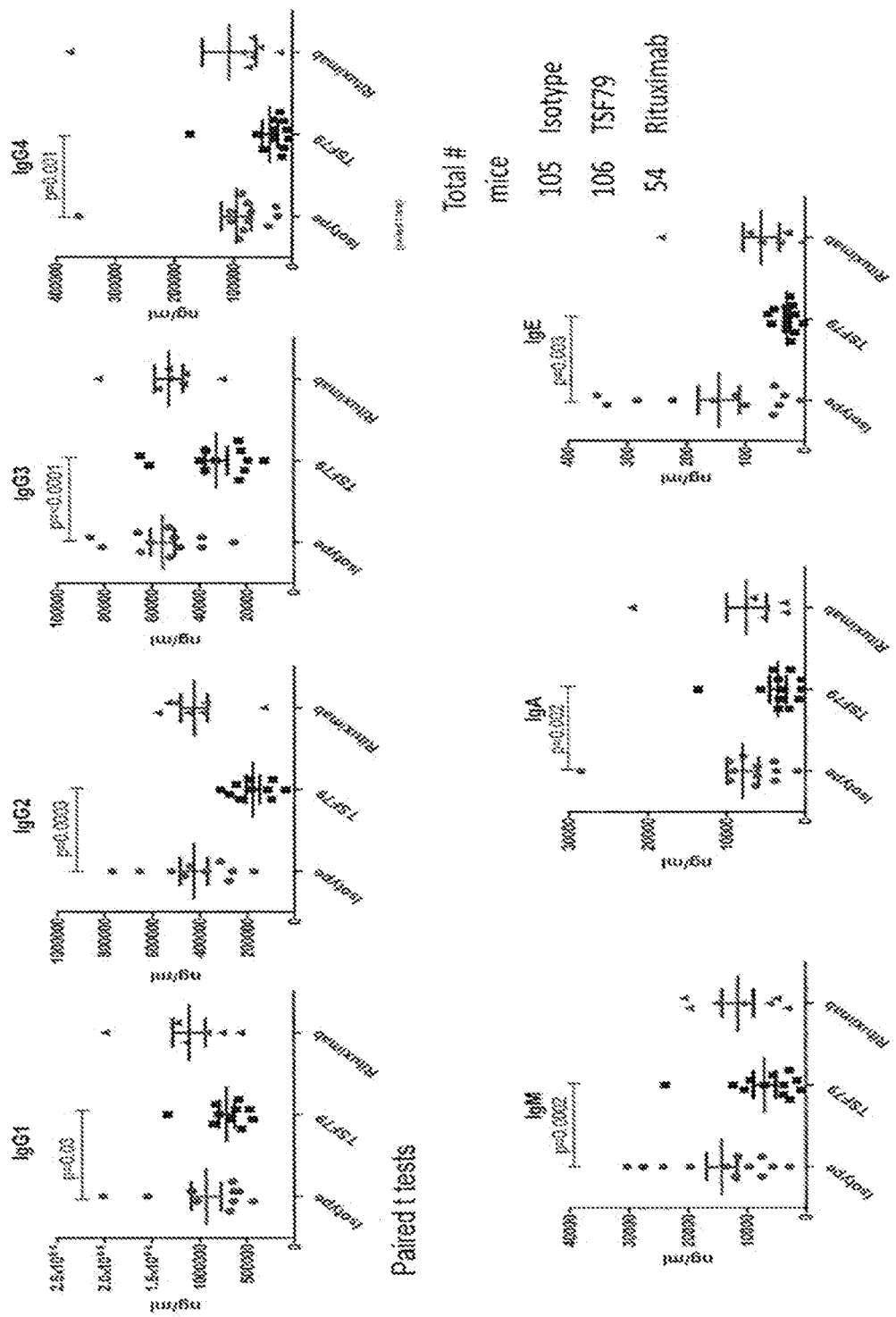
FIG. 9 is similar to FIG. 8 for Ab79 depleting activity in HuSCID mice as described in the Examples.

The in vivo efficacy of Ab19 and Ab79 was tested in a disseminated Daudi-luciferase model of human lymphoma. 6-8 week old female CB.17 SCID mice from Taconic Laboratories were injected intravenously with $1 \times 10^6$ Daudi-Luc tumor cells. At study day 7, mice were treated intraperitoneally with: palivizumab, Ab 79, Ab19, Benchmark 1, and Benchmark 2. Bioluminescent imaging was performed weekly starting from day 21 using an IVIS Xenogen system (Caliper Life Sciences) to monitor tumor burden. For imaging, animals were injected IP with luciferase substrate (150 mg/kg) 10 min before the imaging, then the animals were anaesthetized under isoflurane and imaged. Results are shown in FIG. 8 and FIG. 9.

Example 14: Inflammatory/Immunological Disease Correlation

CD38 was shown to be dramatically upregulated in PBMC cells following activation. In resting PMBCs from normal donors, less than 20% of the resting cells express CD38, with receptor numbers being calculated at roughly 10,000-20,000 per cell. Activated PMBCs, again from normal donors, showed 60-75% of the cells expressing CD38, with the receptor numbers showing 110,000 to 160,000 per cell.

Figure 5:
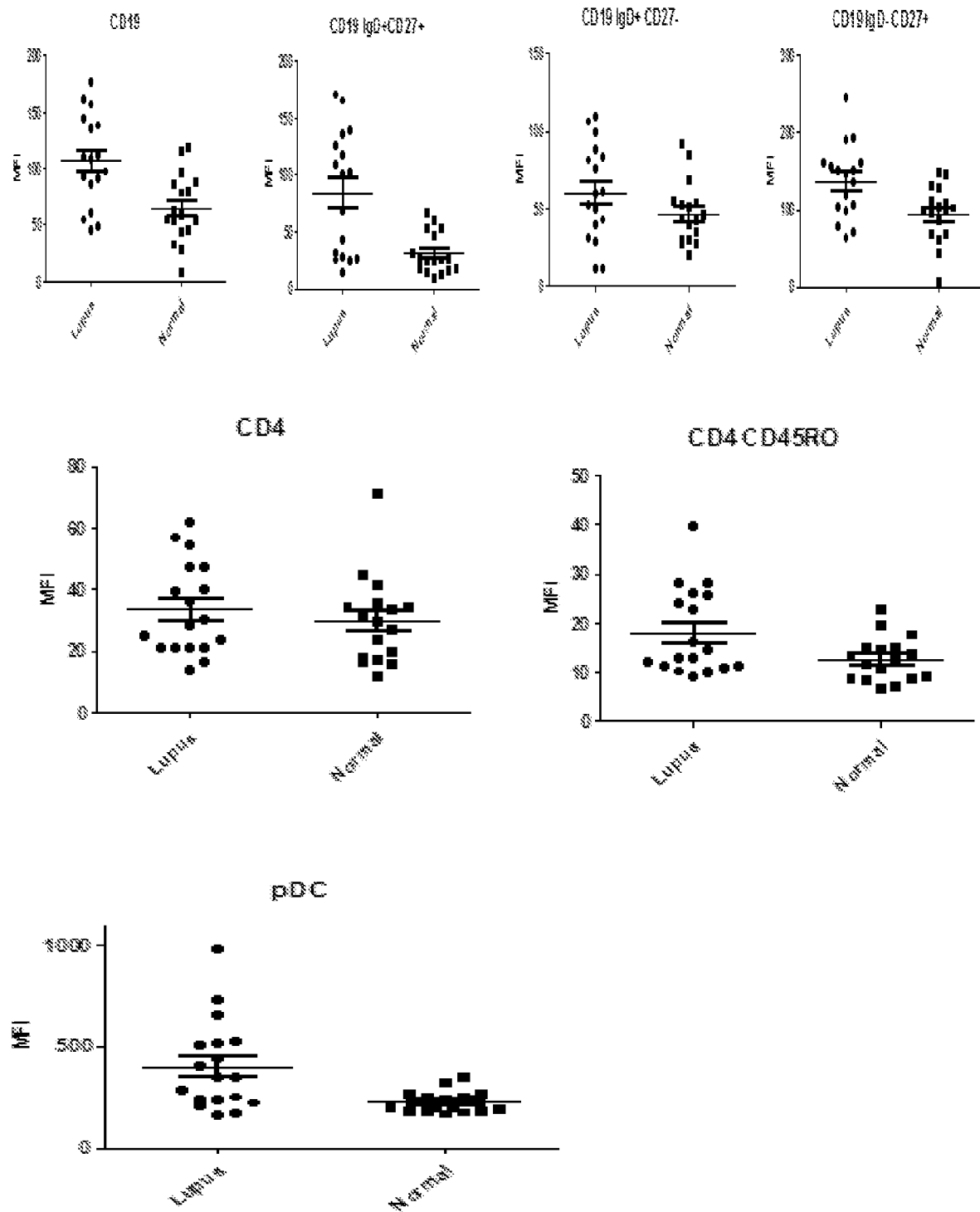
FIG. 5 depicts the increased expression of CD38 in PMBCs from SLE patients using a commercially available human CD38 antibody.

In addition, as shown in FIG. 5, CD38 showed increased expression in PMBCs from SLE patients.

Samples were immunohistologically tested for overexpression of CD38. 19 samples from SLE patients were analyzed, resulting in the observation of increased CD38 expression on B and T memory cells and pDCs. 3 RA patients were analyzed, showing the infiltration of CD38 plasma cells in synovium tissue in all three patients, as well as increased staining of synovium tissues with Ab79. 7

Chrohn's Disease patients and 6 ulcerative colitis patients were analyzed, and showed the infiltration of CD38 expressing plasma cells in smooth muscle of the colon (tested on two primary cell samples from patients. It should be noted that the same number of normal patients were tested without showing these results.

Example 15: Depletion Using Anti-CD38 Antibodies

Figure 6:
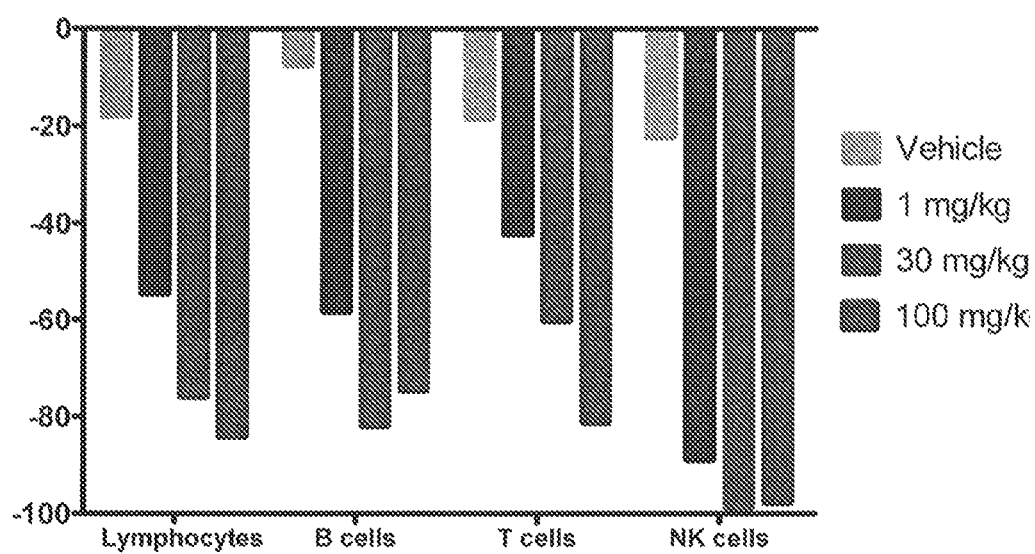
FIG. 6 depicts the percentage change in cell numbers in cyno monkeys at 24 hours after dosing.

Dosing cynomolgus monkeys with Ab79 shows a significant decrease in lymphocytes, B and T cells, and NK cells. The antibody was dosed via a 30 minute IV infusion at the dosages shown in FIG. 6, with the data being collected at 24 hours. Similar data was shown at day 4, 7, 11 and 18.

Figure 7:
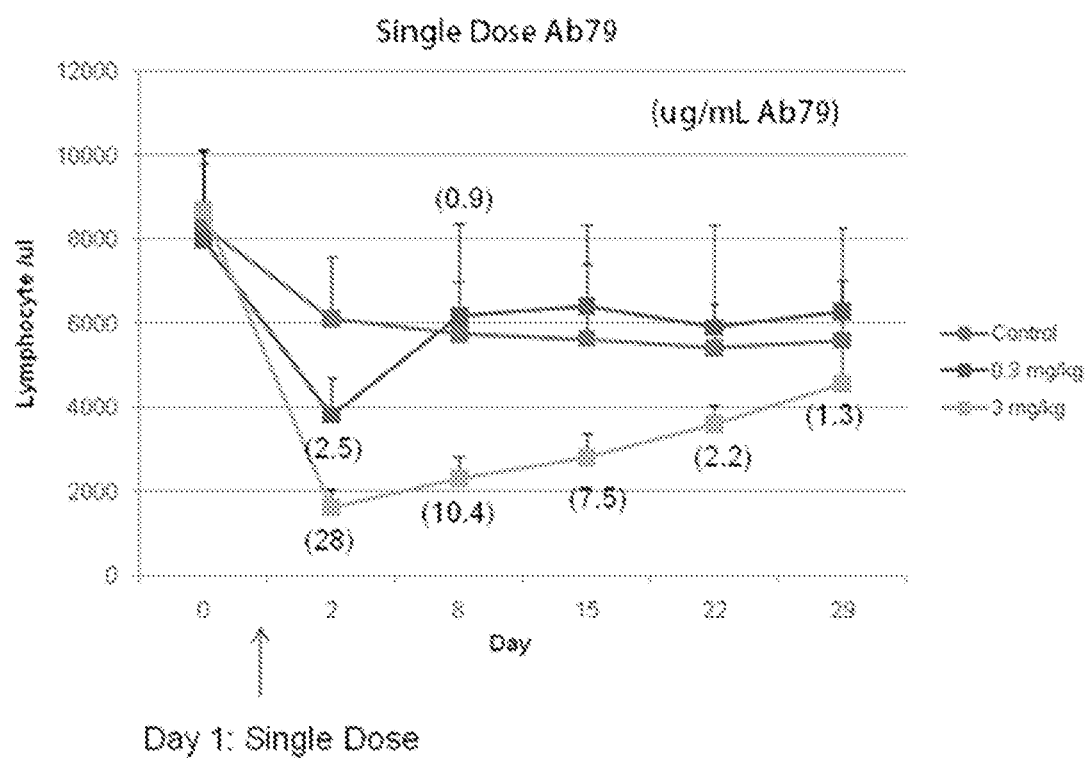
FIG. 7 shows the recovery of depletion after a single dose of Ab79.

However, the pK/pD data shows the recovery of the animals after dosing. As shown in FIG. 7, lymphocyte count returned similar to control counts after a period of days after a single IV 30 minute infusion dose, even after the highest dose, indicating that there are no issues with the lymphoid progenitor cells.

Example 16: Autoimmune Disease Models

Three Different Models are Used

Figure 10:
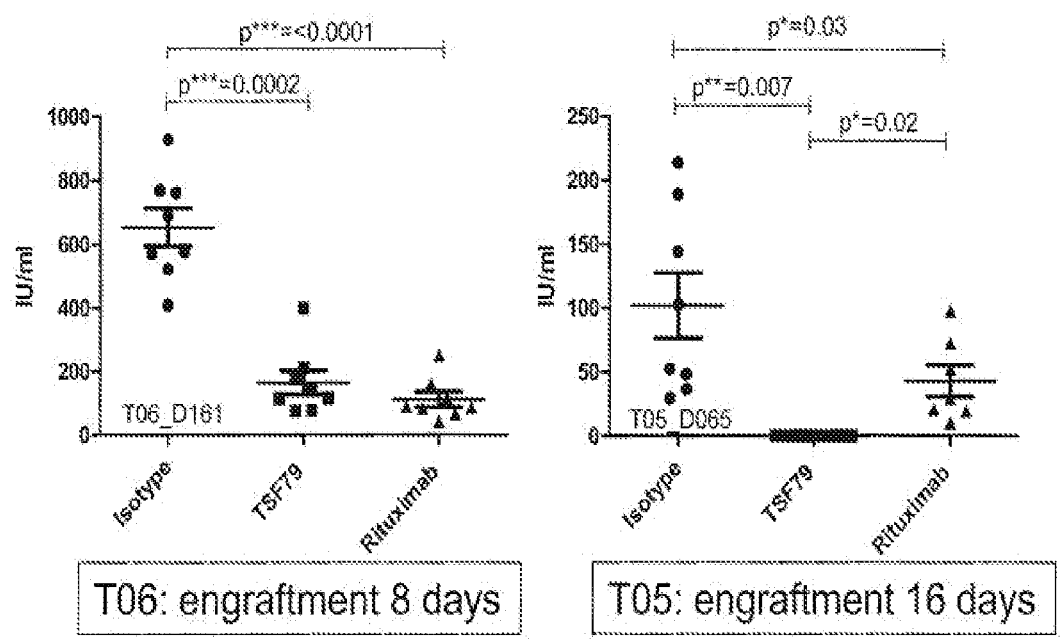
FIG. 10 depicts the significant reduction of the anti-tetanus response in the HuSCID model upon Ab79 treatment.
Figure 11:
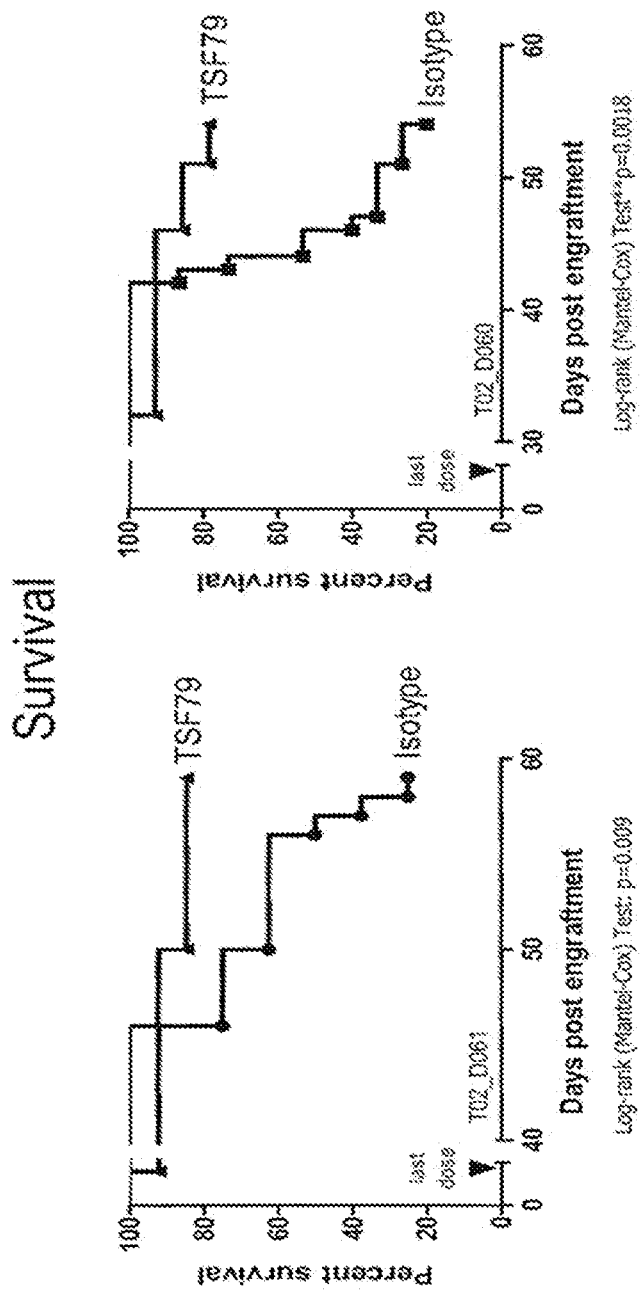
FIG. 11 shows, again in the HuSCID model, the significant increase in survival upon Ab79 treatment, essentially a type of graft versus host model.

A HuScid mouse model served as a pseudo-graft-versus-host model as well as a model for anti-tetanus response, IgG depletion, and overall survival. CB17/HuSCID mice were injected with ASGM1 to deplete NK cells, and then injected with human PBMCs a day later. The engraftment was allowed to proceed for 7-10 days, with serum collected for human Ig randomization. A day later, the mice were injected with Ab79 at 10 mg/kg followed by TTd, with a second dose 4 days later, a third dose 3 days after that, with serum collected for human Ig counting and anti-tetanus detection 3 days after that (total 10 days from first dose). FIG. 8 shows the results from a single mouse donor, which indicate significant reductions of all Ig isotypes upon treatment. FIG. 9 shows the results of the average Ig levels for each group of recipients, with each data point representing the average value per group (n=5 to n=10). FIG. 10 shows the significant reduction of the anti-tetanus response upon AB79 treatment. Finally, FIG. 11 shows overall significant survival using the Ab79 treatment.

Surrogate Mouse Experiments

Figure 12:
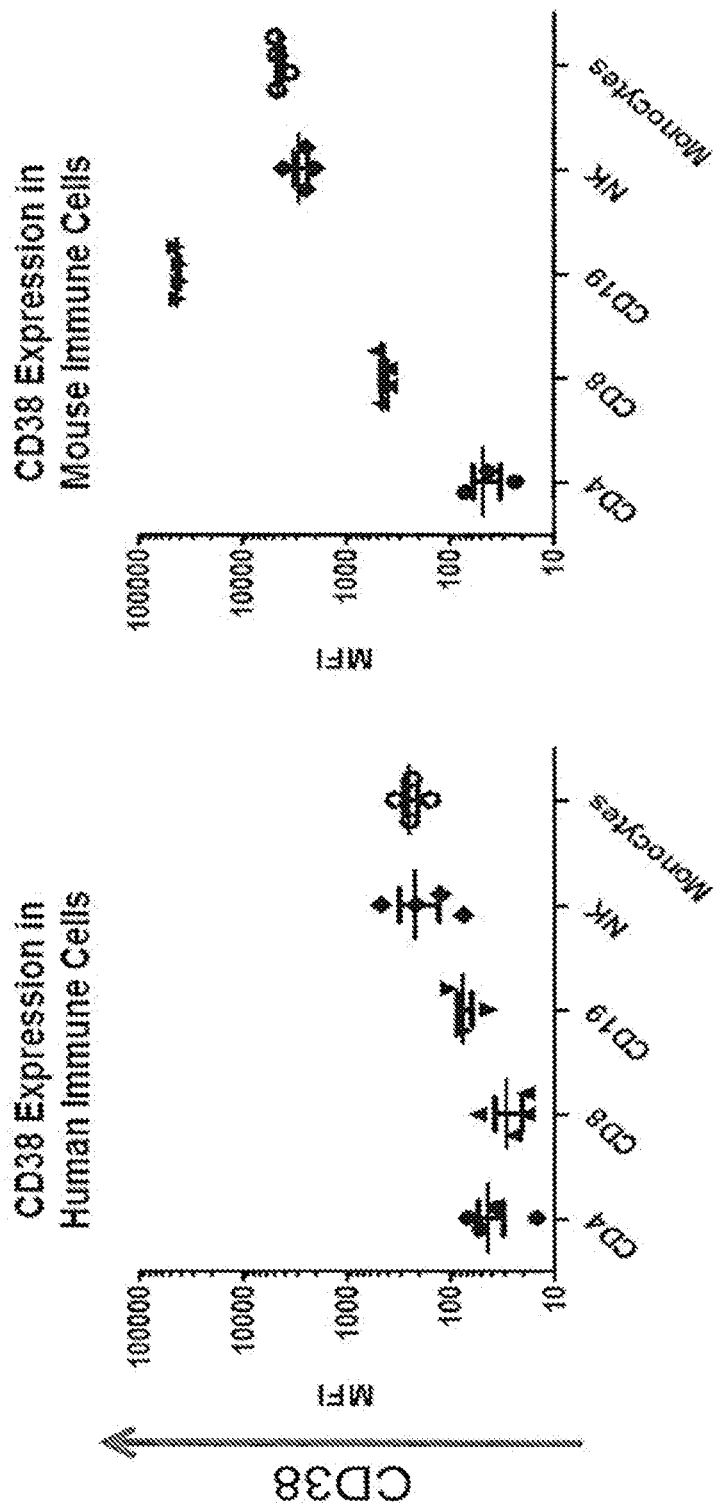
FIG. 12 depicts the differences in expression of the CD38 antigen in human and mouse PBMCs, using commercial antibodies to each.

As Ab79 does not cross react with rodent CD38, a surrogate antibody was developed. As a preliminary matter, using a commercial antibody to human CD38 and a commercial antibody to mouse CD38, significant differences are shown in the CD38 expression levels among cells types between the human and mouse (see FIG. 12), showing that the biology of disease is different. Thus, using antibodies that cross react with monkey CD38 in monkey models may give significantly better results.

Figure 13:
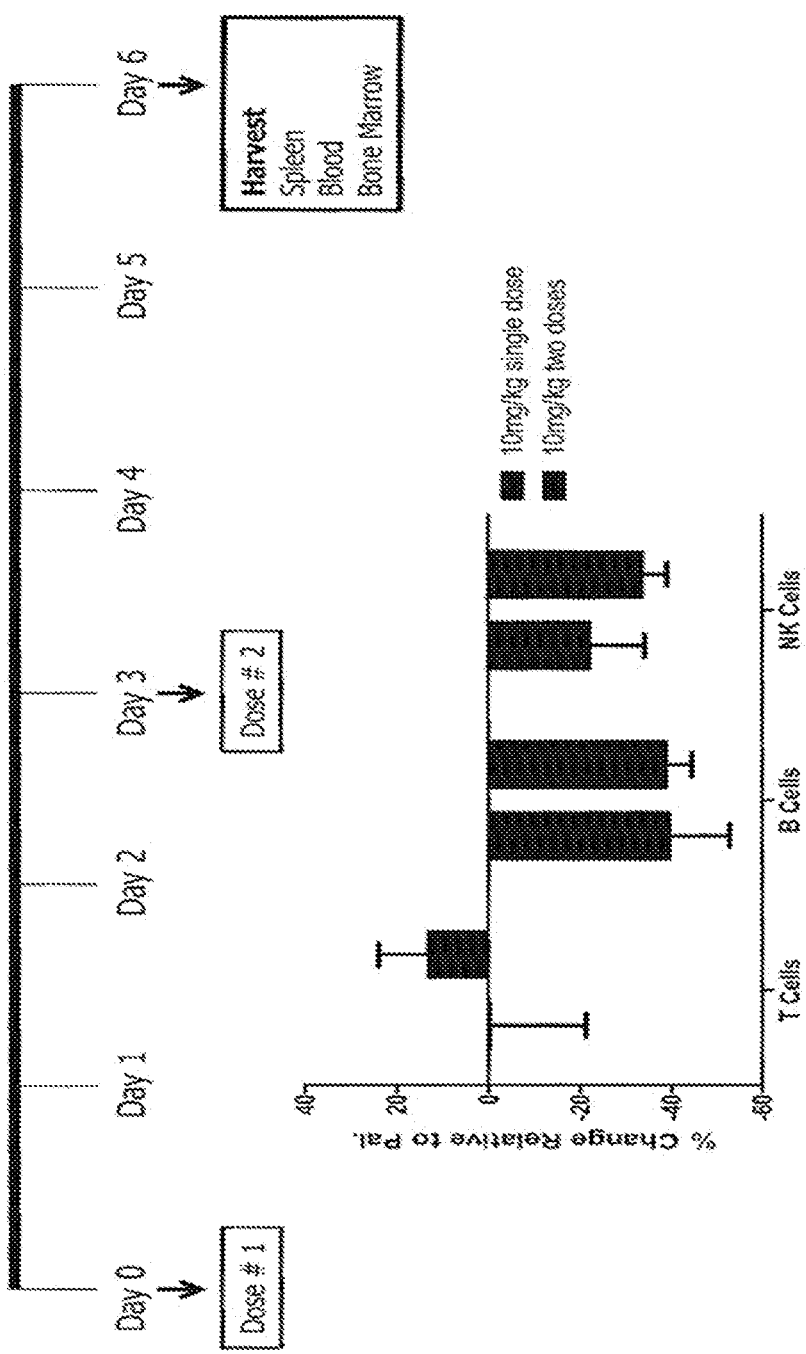
FIG. 13 shows the therapeutic effect in an inflammatory setting, in showing the surrogate mouse anti-CD38 antibody depletes immune cells from peripheral blood.
Figure 14:
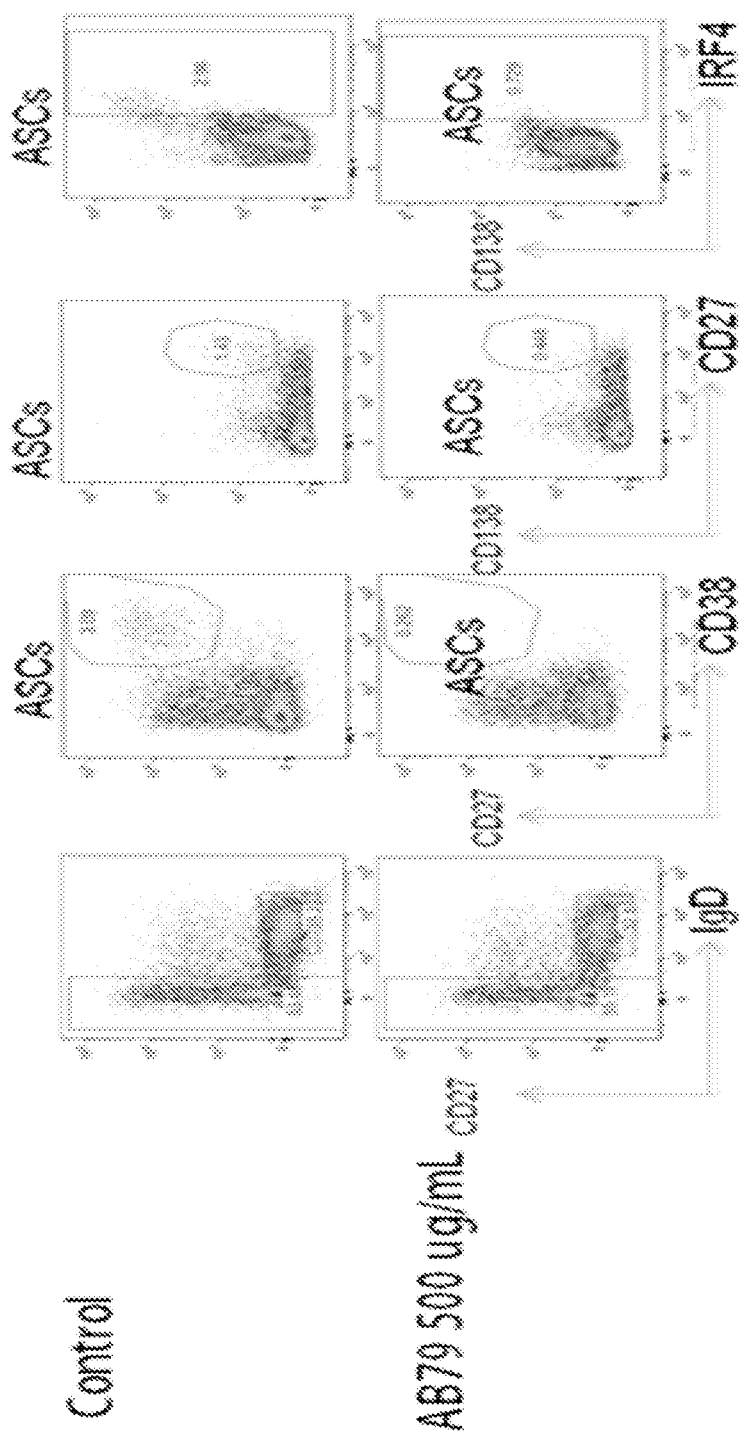
FIG. 14 shows Ab79 depletes blood plasmablasts (CD38+, CD27+), plasma cells (CD138+, CD27+) and (CD138+, IRF4+).

A surrogate antibody was developed, showing similar depletion of CD38+ cells harvested from spleen, blood and bone marrow (data not shown) as well as from peripheral blood (see FIG. 13). In addition, the kinetics of depletion are shown in FIG. 14, with spleen, blood and bone marrow collected at 1, 2 or 3 days after a single dose of mouse surrogate at 10 mg/kg. A rapid depletion of B cells in blood was shown within 24 hours, with a slower depletion sown in spleen and bone marrow.

Mouse SLE Model

The surrogate mouse anti-CD38 is tested in the MRL/lpr model, using the following interim readouts (for example, every two weeks), from blood: anti-dsDNA autoantibodies, CBC, FACS for T/B cell depletion, protein albumin in urine and skin inflammation). Terminal readouts include, but are not limited to, from blood: anti-dsDNA autoantibodies, CBC, FACS for T/B cell depletion, from spleen, lymph nodes and bone marrow: organ weight, immune cell numbers, FACS for T/B cell depletion, for kidney: organ weight, histopath (H&E and PAS), IC disposition, inflammatory cells, and skin inflammation (histopath).

Collagen Induced Arthritis (Cia) Model

A mouse CIA model was used using the mouse surrogate antibody, with 7 groups of mice to evaluate both pro-prophylatic, prophylatic and therapeutic efficacy. All mice were immunized with CII/CFA at day 0, with a CII/CFA boost at day 21, generally resulting in disease progression from day 21 to day 42 (study termination). Group 1 (10 mice) was IP injected with 10 mg/kg surrogate antibody twice a week, starting at day 0 (pro-prophylatic). Group 2 (n=10) was similarly dosed but starting at day 21. Group 3 (n=10) was similarly injected at disease onset (day 25-28). Group 4 (n=10) was dosed at the same level but with a hIgG1 (e.g. isotype) at Day 0. Group 5 (n=10) was dosed at the same level with hIgG1 but starting at day 21. Group 6)(n=10) was dosed at day 21 with 0.5 mg/l water of dexamethasone, and Group 7 (n=5) was not treated.

A cynomolgus monkey CIA study is done, using n=3 for each group, group 1 is naïve animals, vehicle only. Group 2 is a single dose of Ab79 at 3 mg/kg or 10 mg/kg, q1w (prophylatic treatment starts at day 7 after collagen immunization). Group 3 is Ab79 at 3 mg/kg or 10 mg/kg q1w, for therapeutic treatment, starting at disease onset, day 21 or day 28. Group 4 is treated with 0.1 mg/kg q1d with dexamethasone at disease onset as well.

Example 17: Ab79 Depletes Human Plasma Cells/Plasmablasts In Vitro

Figure 15:
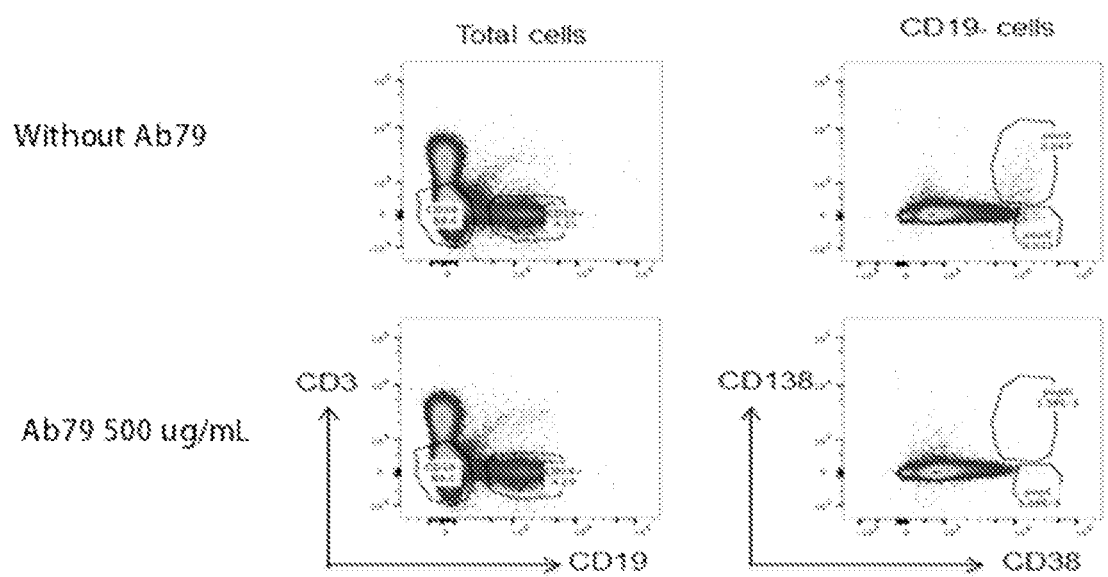
FIG. 15 shows Ab79 depletes bone marrow derived long-lived plasma cells (CD19−, CD38+, CD138+).
Figure 16:
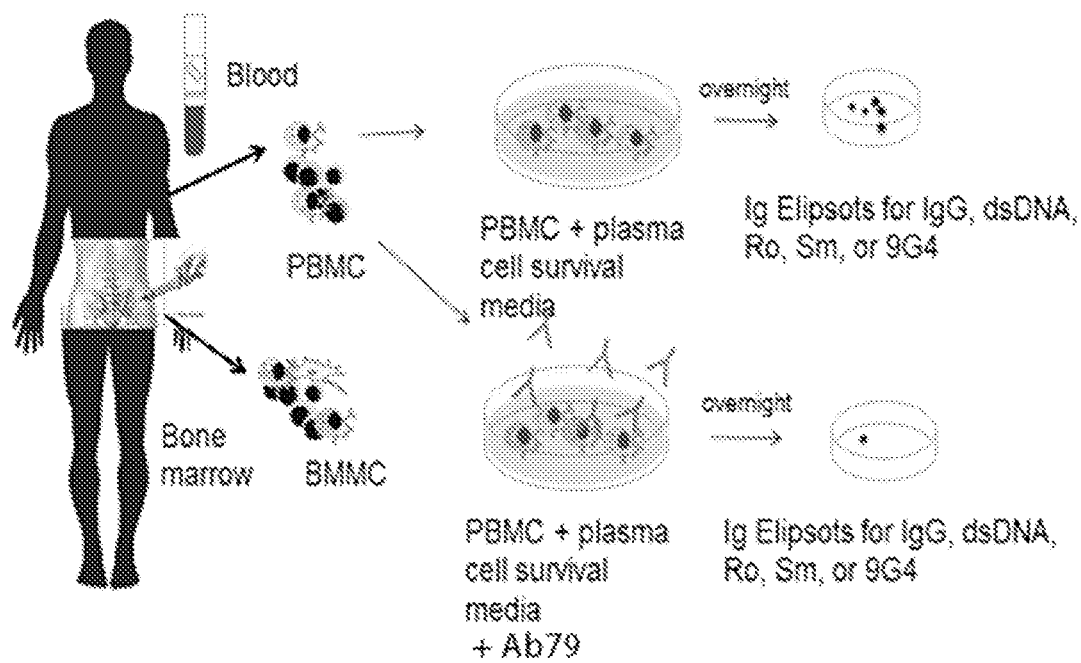
FIG. 16 shows sample collection, culture and experimental endpoints.
Figure 19:
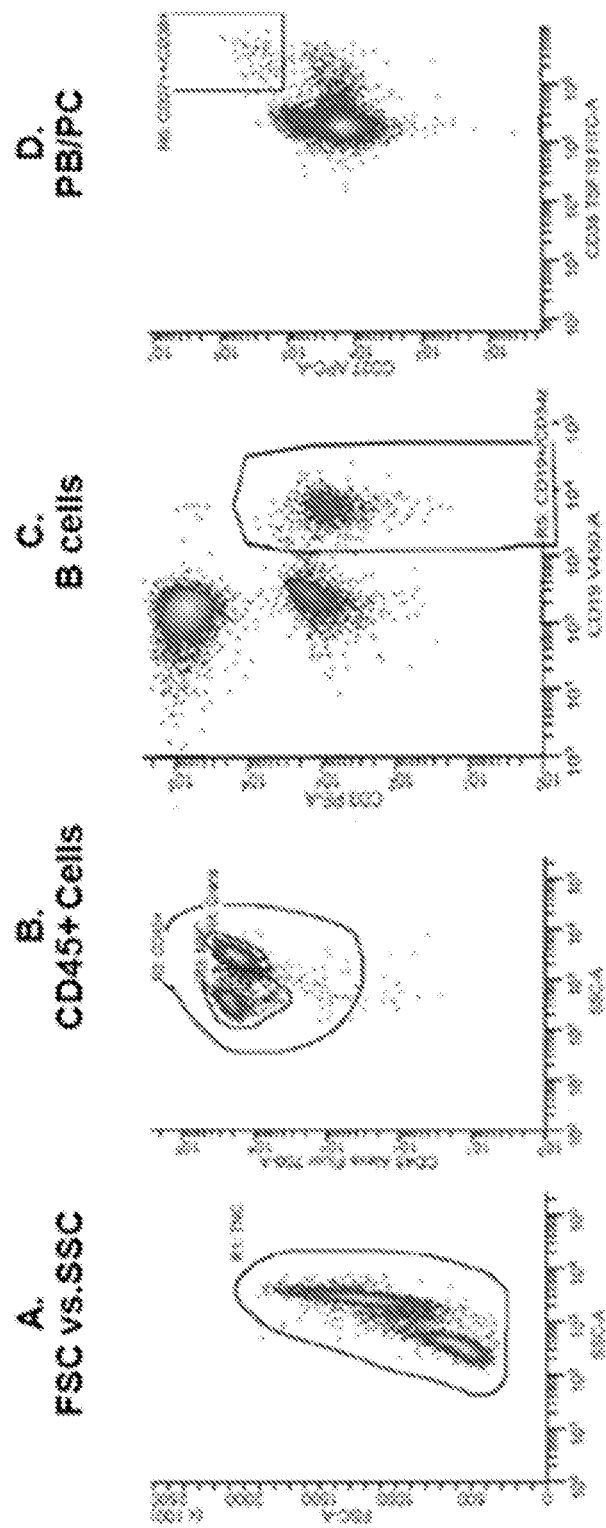
FIG. 19 shows that plasmablasts and plasma cells (CD45+, CD3−, CD19+, CD27+, CD38+) can be detected in whole blood by flow cytometric analyses using the methods described herein.

In an in vitro culture system using human peripheral blood mononuclear cells (PBMC) or bone marrow mononuclear cells (BMMC), the addition of Ab79 depletes PB/PC populations, which are characterized by the cell surface expression of CD27, CD38, and CD138 and the intracellular plasma cell markers IRF4 (FIG. 14). Ab79 depletes both short-lived plasma cells (CD19+ plasma cells), and long-lived plasma cells (CD19− plasma cells) from bone marrow (FIG. 15). Plasma cells and plasmablasts are the primary antibody secreting cells (ASCs) in the body. See Hibi T and Dosch H M. Eur J Immunol (1986) 16(2):139-145. ASCs measured directly by ELISpot (FIG. 16) are reduced in healthy subject and SLE patient samples (FIG. 17). In samples from healthy subjects in the top panel, Ab79 treatment results in a 70% reduction in the number of IgG producing cells from blood and bone marrow. Similar depletion is seen in SLE patient samples. Additionally the number of cells producing the autoantigen-specific antibodies VH4-34 9G4+ and anti-Ro are reduced (FIG. 18). These results highlight the potential of Ab79 monoclonal antibody as a therapeutic for the treatment for SLE by PB/PC depletion. By targeting CD38, a molecule highly expressed on all PB/PC cells, Ab79 effectively depletes both short lived and long-lived ASCs.

Example 18: Detecting PB/PC in Whole Blood Using a Method Suitable for Use in Clinical Setting and in Subjects Treated with Ab79

Flow cytometric analyses of whole blood from a healthy volunteer shows CD38 is highly expressed on PB/PC and that staining using the fix/freeze method described below with the Ab19 mAb clearly discriminate the CD45+, CD3−, CD19+, CD38+, CD27+ subpopulation of B cells that contains both PB and PC (FIG. 19a-d).

Whole blood collected from a healthy volunteer is stained with CD3-PE); CD27-APC; CD45-AF700 CD19-V450; CD38-FITC. For flow cytometric analysis cells are gated to identify single cells, then forward (FSC) vs. side scatter (SSC) are used to compare blood relative size and granularity (A) and on this basis CD45+staining of mononuclear cells lymphocytes are identified (B). B cells, within this population, are identified as CD3− CD19+ cells (C). Both plasmablasts and plasma cells are identified as CD27+CD38 bright cells (panel D).

To stain the whole blood samples, tubes containing donor sample aliquots are centrifuged at 500 RCF for 5 minutes, the supernatant decanted, and the tubes rack-raked to disperse the cell pellets. The cells are washed with 2 mL of PBS with 1% BSA, centrifuged at 500 RCF for 5 minutes, the supernatant decanted, and the tubes rack-raked to disperse the cell pellets. A cell count is taken for each specimen and the cell count is adjusted between $20 \times 10^6$ cells/mL and $40 \times 10^6$ cells/mL with PBS with 1% BSA if necessary. 200 µL is pipetted into the appropriately labeled tube. The appropriate amount of human serum is added to each tube, vortexed and placed in the dark to incubate for 10 minutes. Each tube receives the appropriate amount of antibodies. All samples are vortexed well and incubated for 30 minutes at room temperature in the dark. After incubation, the cells are washed with 2 mL of PBS with 1% BSA. The tubes are centrifuged at 500 RCF for 5 minutes, supernatant decanted, and the tubes rack-raked to disperse the cell pellets. After centrifugation the cells are reconstituted in 500 µL 1% Paraformaldehyde. The samples are acquired on a BD FACSCantoII Flow Cytometer. Approximately 1,000,000 total events are acquired or until 240 seconds had been reached. The following reagents were are used for staining:

CD3 PE (Clone: SK7)—BD, Catalog number 347347;
CD27 APC (Clone: M-T271)—BD Pharmingen, Catalog number 558664;
CD45 AF700 (Clone: HI30)—Biolegend, Catalog number 304024;
CD19 V450 (Clone: HIB19)—BD Horizon, Catalog number 560353;
CD38 (Ab19);
1×FACSLyse;
PBS with 1% BSA;
1% Paraformaldehyde Solution;
Quantum MESF FITC Calibration Beads (LabCorp Analytical Systems);
Quantum MESF APC Calibration Beads (LabCorp Analytical Systems);

Example 19: Comparison of PB/PC Stability in Whole Blood with No Fixative or Treated with FACSLyse and Frozen Traditional Storage Method and Flow Cytometry Five healthy donor whole blood specimens are collected into tubes containing sodium heparin anticoagulant. Samples are tested in triplicate by two independent operators on Day 0 (<2 hours post-collection). Specimens are then held at ambient temperature and tested in singlet on Day 1 (24-30 hours), Day 2 (48-54 hours), and Day 3 (72-48) hours post-collection. Then stained as described for Example 18 Results are shown in Table 4.

TABLE 4

| Donor | Day Post-Collection | Total Events Collected | % of CD19+ B cells that are CD38++/CD27++ |
|---|---|---|---|
| Donor 1 | 0 | 1104419 | 0.85 |
|  | 1 | 226287 | 0.14 |
|  | 2 | 1066353 | 0.13 |
|  | 3 | 1094968 | 0.17 |
| Donor 2 | 0 | 885060 | 0.64 |
|  | 1 | 232424 | 0.40 |
|  | 2 | 615546 | 0.16 |
|  | 3 | 500499 | 0.20 |
| Donor 3 | 0 | 241812 | 0.58 |
|  | 1 | 830574 | 0.14 |
|  | 2 | 853470 | 0.15 |
|  | 3 | 528552 | 0.07 |
| Donor 4 | 0 | 754839 | 2.23 |
|  | 1 | 1046385 | 0.64 |
|  | 2 | 964089 | 0.29 |
|  | 3 | 577233 | 0.27 |
| Donor 5 | 0 | 1112831 | 3.80 |
|  | 1 | 1098387 | 0.99 |
|  | 2 | 1126494 | 0.61 |
|  | 3 | 625239 | 0.42 | c. Fix/Freeze Storage Method and Flow Cytometry

Five healthy donor whole blood specimens (sodium heparin anticoagulant) are collected, and the samples are split into four aliquots. The first aliquot is tested fresh according to the FACSLyse method without a freeze step to establish a baseline measurement of plasmablasts. The fresh samples are tested in triplicate by two independent operators on Day 0 (<2 hours post-collection). The other three aliquots are frozen at −80° C. after 10 minute incubation with FACSLyse. The second aliquot is thawed in the 38° C. water bath and processed on Day 1 (24-30 hours). The third aliquot is thawed on Day 2 (48-54 hours), and the fourth aliquot on Day 3 (72-78 hours) post-collection. Processing for Days 1-3 is performed in singlet.

Frozen aliquots are thawed in a 38° C. water bath until the specimen is fluid in the conical then placed on a sample rocker to complete the thawing process. The tubes are centrifuged at 500 RCF for 5 minutes, the supernatant decanted, and the tubes rack-raked to disperse the cell pellets. The cells are washed with 2 mL of PBS with 1% BSA, centrifuged at 500 RCF for 5 minutes, the supernatant decanted, and the tubes rack-raked to disperse the cell pellets. A cell count is taken for each specimen and the cell count is adjusted between $20 \times 10^6$ cells/mL and $40 \times 10^6$ cells/mL with PBS with 1% BSA if necessary. 200 µL is pipetted into the appropriately labeled tube. The appropriate amount of human serum is added to each tube, vortexed and placed in the dark to incubate for 10 minutes. Each tube receives the appropriate amount of antibodies. All samples are vortexed well and incubated for 30 minutes at room temperature in the dark. After incubation, the cells are washed with 2 mL of PBS with 1% BSA. The tubes are centrifuged at 500 RCF for 5 minutes, supernatant decanted, and the tubes rack-raked to disperse the cell pellets. After centrifugation the cells are reconstituted in 500 µL 1% Paraformaldehyde. The samples are acquired on a BD FACSCantoII Flow Cytometer. Approximately 1,000,000 total events are acquired or until 240 seconds are reached. Results are shown in Table 5.

TABLE 5

| Donor | Day Post-Collection | Total Events Collected | % of CD19+ B cells that are CD38++/CD27++ |
|---|---|---|---|
| Donor 1 | 0 | 1000000 | 0.14 |
|  | 1 | 830650 | 0.10 |
|  | 2 | 908750 | 0.09 |
|  | 3 | 737475 | 0.12 |
| Donor 2 | 0 | 230400 | 0.94 |
|  | 1 | 794125 | 1.03 |
|  | 2 | 662925 | 1.05 |
|  | 3 | 714550 | 1.08 |
| Donor 3 | 0 | 248500 | 0.17 |
|  | 1 | 934225 | 0.21 |
|  | 2 | 315400 | 0.24 |
|  | 3 | 842975 | 0.20 |
| Donor 4 | 0 | 892050 | 0.32 |
|  | 1 | 1000000 | 0.49 |
|  | 2 | 528175 | 0.32 |
|  | 3 | 600675 | 0.24 |
| Donor 5 | 0 | 257450 | 0.48 |
|  | 1 | 1000000 | 0.49 |
|  | 2 | 962875 | 0.43 |
|  | 3 | 1000000 | 0.47 |

Example 20: Ab79 does not Inhibit Staining with the CD38-Specific mAb Ab19

Five healthy donor whole blood specimens (sodium heparin anticoagulant) are collected and spiked with Ab79 (10 μg/mL and zero) for one hour at 37° C. After incubation, the samples are split into four aliquots. The first aliquot is tested fresh according to the FACSLyse method without a freeze step to establish a baseline measurement of plasmablasts. The fresh samples are tested in triplicate by two independent operators on Day 0 (<2 hours post-collection). The other three aliquots are frozen at −80° C. after 10 minute incubation with FACSLyse. The second aliquot is thawed in the 38° C. water bath and processed on Day 1 (24-30 hours). The third aliquot is thawed on Day 2 (48-54 hours), and the fourth aliquot on Day 3 (72-78 hours) post-collection. Processing for Days 1-3 is performed in singlet.

Frozen aliquots are thawed in a 38° C. water bath until the specimen is fluid in the conical then placed on a sample rocker to complete the thawing process. The tubes are centrifuged at 500 RCF for 5 minutes, the supernatant decanted, and the tubes rack-raked to disperse the cell pellets. The cells are washed with 2 mL of PBS with 1% BSA, centrifuged at 500 RCF for 5 minutes, the supernatant decanted, and the tubes rack-raked to disperse the cell pellets. A cell count is taken for each specimen and the cell count is adjusted between $20 \times 10^6$ cells/mL and $40 \times 10^6$ cells/mL with PBS with 1% BSA if necessary. 200 μL is pipetted into the appropriately labeled tube. The appropriate amount of human serum is added to each tube, vortexed and placed in the dark to incubate for 10 minutes. Each tube receives the appropriate amount of antibodies. All samples are vortexed well and incubated for 30 minutes at room temperature in the dark. After incubation, the cells are washed with 2 mL of PBS with 1% BSA. The tubes are centrifuged at 500 RCF for 5 minutes, supernatant decanted, and the tubes rack-raked to disperse the cell pellets. After centrifugation the cells are reconstituted in 500 μL 1% Paraformaldehyde. The samples are acquired on a BD FACSCantoII Flow Cytometer. Approximately 1,000,000 total events are acquired or until 240 seconds is reached. Results are shown in Table 6.

TABLE 6

| Healthy Blood donors | Total Events Collected | % of CD19+ B cells that are CD38++/CD27++ In the presence of 10 microgram/ml Ab79 | Total Events Collected | % of B cells (CD19+) that are CD38++/CD27++ No Ab79 added |
|---|---|---|---|---|
| Donor 1 | 1000000 | 0.14 | 1000000 | 0.14 |
| Donor 2 | 818625 | 0.86 | 230400 | 0.94 |
| Donor 3 | 247425 | 0.18 | 248500 | 0.17 |
| Donor 4 | 255675 | 0.28 | 892050 | 0.32 |
| Donor 5 | 255400 | 0.48 | 257450 | 0.48 |

Example 21: Healthy Subjects Treated with Ab79 Exhibit a Dose-Dependent Reduction in PB/PC as Measured Using the Fix/Freeze Method and Flow Cytometric Analyses PB/PC levels are evaluated in highest dose cohorts of Ab79 randomized, double-blind, placebo-controlled, single-dose study in healthy subjects. Ab79 or placebo is administered either as a 2-hour IV infusion or as a SC administration at multiple dose levels. Whole blood is collected at a clinical site. Samples collected prior to treatment (2 screening times, Day −1 and pre-dose Day 1) are used to establish a baseline. Post treatment samples are collected at 14 time points over a time period of 1 hour up to 78 days depending upon route of administration. The majority of PB/PC data is collected in subjects treated SC. All samples are preserved using the Fix/Freeze method described above and are analyzed using multicolor flow cytometric analyses.

Figure 20:
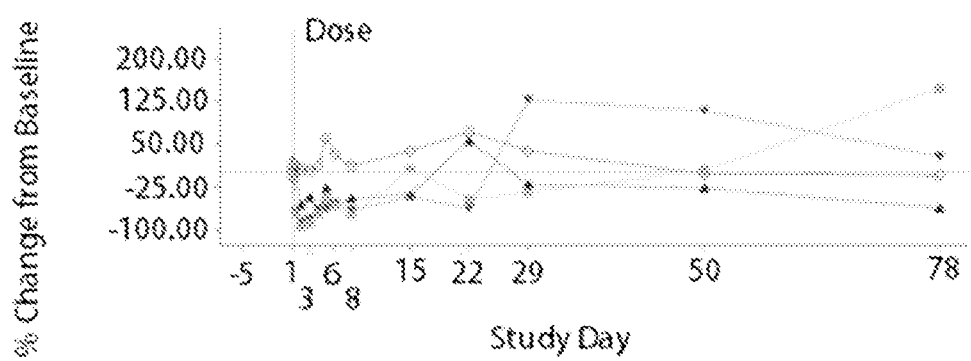
FIG. 20 shows flow cytometric analysis of blood cells preserved by the Fix/Freeze method described herein following treatment of healthy volunteers with Ab79, and shows that Ab79 depletes plasmablasts and plasma cells. (o) Placebo; (9) Ab79 (0.03 mg/kg); (A) Ab79 (0.1 mg/kg); (V) Ab79 (0.3 mg/kg); (n) Ab79 (0.6 mg/kg).

Comparison of the median blood PB/PC cell counts in SC treated subjects showed that after placebo treatment there are variations in PB/PC levels over time but treatment with Ab79 results in a consistent decrease of PB/PC in Ab79 treatment group that lasts for up to 20 days. Results are shown in FIG. 20.

```
SEQUENCE LISTING
(CD38 Homo sapiens; NP_001766.2)
                                        SEQ ID NO: 1
MANCEFSPVSGDKPCCRLSRRAQLCLGVSILVLILVVVLA

VVVPRWRQQWSGPGTTKRFPETVLARCVKYTEIHPEMRHV

DCQSVWDAFKGAFISKHPCNITEEDYQPLMKLGTQTVPCN

KILLWSRIKDLAHQFTQVQRDMFTLEDTLLGYLADDLTWC

GEFNTSKINYQSCPDWRKDCSNNPVSVFWKTVSRRFAEAA

CDVVHVMLNGSRSKIFDKNSTFGSVEVHNLQPEKVQTLEA

WVIHGGREDSRDLCQDPTIKELESIISKRNIQFSCKNIYR

PDKFLQCVKNPEDSSCTSEI (CD38 Macaca fascicularis; AAT36330.1)
                                        SEQ ID NO: 2
MANCEFSPVSGDKPCCRLSRRAQVCLGVCLLVLLILVVVV

AVVLPRWRQQWSGSGTTSRFPETVLARCVKYTEVHPEMRH

VDCQSVWDAFKGAFISKYPCNITEEDYQPLVKLGTQTVPC

NKTLLWSRIKDLAHQFTQVQRDMFTLEDMLLGYLADDLTW

CGEFNTFEINYQSCPDWRKDCSNNPVSVFWKTVSRRFAET

ACGVVHVMLNGSRSKIFDKNSTFGSVEVHNLQPEKVQALE
```

-continued

AWVIHGGREDSRDLCQDPTIKELESIISKRNIRFFCKNIY
RPDKFLQCVKNPEDSSCLSGI (HCDR1 Ab79)
SEQ ID NO: 3
GFTFDDYG (HCDR2 Ab79)
SEQ ID NO: 4
ISWNGGKT (HCDR3 Ab79)
SEQ ID NO: 5
ARGSLFHDSSGFYFGH (LCDR1 Ab79)
SEQ ID NO: 6
SSNIGDNY (LCDR2 Ab79)
SEQ ID NO: 7
RDS (LCDR3 Ab79)
SEQ ID NO: 8
QSYDSSLSGS (Heavy Chain Ab79)
SEQ ID NO: 9
EVQLLESGGGLVQPGGSLRLSCAASGFTFDDYGMSWVRQA
PGKGLEWVSDISWNGGKTHYVDSVKGQFTISRDNSKNTLY
LQMNSLRAEDTAVYYCARGSLFHDSSGFYFGHWGQGTLVT
VSSASTKGPSVFPLA (Light Chain Ab79)
SEQ ID NO: 10
QSVLTQPPSASGTPGQRVTISCSGSSSNIGDNYVSWYQQL
PGTAPKLLIYRDSQRPSGVPDRFSGSKSGTSASLAISGLR
SEDEADYYCQSYDSSLSGSVFGGGTKLTVLGQPKANPTVT
LFPPSSEEL (Heavy Chain Ab19)
SEQ ID NO: 11
EVQLLESGGGLVQPGGSLRLSCAASGFTFNNYDMTWVRQA
PGKGLEWVAVISYDGSDKDYADSVKGRFTISRDNSKNTLY
LQMNSLRAEDTAVYYCARVYYYGFSGPSMDVWGQGTLVTV
SSASTKGPSVFPLA (Light Chain Ab19)
SEQ ID NO: 12
QSVLTQPPSASGTPGQRVTISCSGSNSNIGSNTVNWYQQL
PGTAPKLLIYSDSNRPSGVPDRFSGSKSGTSASLAISGLR
SEDEADYYCQSYDSSLSGSRVFGGGTKLTVLGQPKANPTV
TLFPPSSEEL (HCDR1 Ab19)
SEQ ID NO: 13
GFTFNNYD (HCDR2 Ab19)
SEQ ID NO: 14
ISYDGSDK HCDR3 Ab19)
SEQ ID NO: 15
ARVYYYGFSGPSMDV (LCDR1 Ab19)
SEQ ID NO: 16
NSNIGSNT (LCDR2 Ab19)
SEQ ID NO: 17
SDS (LCDR3 Ab19)
SEQ ID NO: 18
QSYDSSLSGSR (Heavy Chain Ab19) w/constant
SEQ ID NO: 19
EVQLLESGGGLVQPGGSLRLSCAASGFTFNNYDMTWVRQA
PGKGLEWVAVISYDGSDKDYADSVKGRFTISRDNSKNTLY
LQMNSLRAEDTAVYYCARVYYYGFSGPSMDVWGQGTLVTV
SSASTKGPSVFPLAPSSKSTSGGTAALGCLVKDYFPEPVT
VSWNSGALTSGVHTFPAVLQSSGLYSLSSVVTVPSSSLGT
QTYICNVNHKPSNTKVDKRVEPKSCDKTHTCPPCPAPELL
GGPSVFLFPPKPKDTLMISRTPEVTCVVVDVSHEDPEVKF
NWYVDGVEVHNAKTKPREEQYNSTYRVVSVLTVLHQDWLN
GKEYKCKVSNKALPAPIEKTISKAKGQPREPQVYTLPPSR
EEMTKNQVSLTCLVKGFYPSDIAVEWESNGQPENNYKTTP
PVLDSDGSFFLYSKLTVDKSRWQQGNVFSCSVMHEALHNH
YTQKSLSLSPGK (Light Chain Ab19) w/constant
SEQ ID NO: 20
QSVLTQPPSASGTPGQRVTISCSGSNSNIGSNTVNWYQQL
PGTAPKLLIYSDSNRPSGVPDRFSGSKSGTSASLAISGLR
SEDEADYYCQSYDSSLSGSRVFGGGTKLTVLGQPKANPTV
TLFPPSSEELQANKATLVCLISDFYPGAVTVAWKADGSPV
KAGVETTKPSKQSNNKYAASSYLSLTPEQWKSHRSYSCQV
THEGSTVEKTVAPTECS (Heavy Chain Ab79)
SEQ ID NO: 21
EVQLLESGGGLVQPGGSLRLSCAASGFTFDDYGMSWVRQA
PGKGLEWVSDISWNGGKTHYVDSVKGQFTISRDNSKNTLY
LQMNSLRAEDTAVYYCARGSLFHDSSGFYFGHWGQGTLVT
VSSASTKGPSVFPLAPSSKSTSGGTAALGCLVKDYFPEPV
TVSWNSGALTSGVHTFPAVLQSSGLYSLSSVVTVPSSSLG
TQTYICNVNHKPSNTKVDKRVEPKSCDKTHTCPPCPAPEL
LGGPSVFLFPPKPKDTLMISRTPEVTCVVVDVSHEDPEVK
FNWYVDGVEVHNAKTKPREEQYNSTYRVVSVLTVLHQDWL
NGKEYKCKVSNKALPAPIEKTISKAKGQPREPQVYTLPPS
REEMTKNQVSLTCLVKGFYPSDIAVEWESNGQPENNYKTT
PPVLDSDGSFFLYSKLTVDKSRWQQGNVFSCSVMHEALHN
HYTQKSLSLSPGK (Light Chain Ab79)
SEQ ID NO: 22
QSVLTQPPSASGTPGQRVTISCSGSSSNIGDNYVSWYQQL -continued

PGTAPKLLIYRDSQRPSGVPDRFSGSKSGTSASLAISGLR

SEDEADYYCQSYDSSLSGSVFGGGTKLTVLGQPKANPTVT

LFPPSSEELQANKATLVCLISDFYPGAVTVAWKADGSPVK

AGVETTKPSKQSNNKYAASSYLSLTPEQWKSHRSYSCQVT

HEGSTVEKTVAPTECS (CD157 Homo sapiens; NP_004325)
SEQ ID NO: 23
MAAQGCAASRLLQLLLQLLLLLLLAAGGARARWRGEGTS

AHLRDIFLGRCAEYRALLSPEQRNKNCTAIWEAFKVALDK

DPCSVLPSDYDLFINLSRHSIPRDKSLFWENSHLLVNSFA

DNTRRFMPLSDVLYGRVADFLSWCRQKNDSGLDYQSCPTS

EDCENNPVDSFWKRASIQYSKDSSGVIHVMLNGSEPTGAY

PIKGFFADYEIPNLQKEKITRIEIWVMHEIGGPNVESCGE

GSMKVLEKRLKDMGFQYSCINDYRPVKLLQCVDHSTHPDC

ALKSAAAATQRKAPSLYTEQRAGLIIPLFLVLASRTQL (Benchmark 1; Heavy Chain Variable Region)
SEQ ID NO: 24
EVQLLESGGGLVQPGGSLRLSCAVSGFTFNSFAMSWVRQA

PGKGLEWVSAISGSGGGTYYADSVKGRFTISRDNSKNTLY

LQMNSLRAEDTAVYFCAKDKILWFGEPVFDYWGQGTLVTV

SS (Benchmark 1; Light Chain Variable Region)
SEQ ID NO: 25
EIVLTQSPATLSLSPGERATLSCRASQSVSSYLAWYQQKP

GQAPRLLIYDASNRATGIPARFSGSGSGTDFTLTISSLEP

EDFAVYYCQQRSNWPPTFGQGTKVEIKR (Benchmark 2; Heavy Chain Variable Region)
SEQ ID NO: 26
QVQLVQSGAEVAKPGTSVKLSCKASGYTFTDYWMQWVKQR

PGQGLEWIGTIYPGDGDTGYAQKFQGKATLTADKSSKTVY

MHLSSLASEDSAVYYCARGDYYGSNSLDYWGQGTSVTVSS (Benchmark 2; Light Chain Variable Region)
SEQ ID NO: 27
DIVMTQSHLSMSTSLGDPVSITCKASQDVSTVVAWYQQKP

GQSPRRLIYSASYRYIGVPDRFTGSGAGTDFTFTISSVQA

EDLAVYYCQQHYSPPYTFGGGTKLEIKR (Heavy Chain Ab43)
SEQ ID NO: 28
EVQLLESGGGLVQPGGSLRLSCAASGFTFSSYGMHWVRQA

PGKGLEWVSRINSDGSSTSYADSMKGQFTISRDNSKNTLY

LQMNSLRAEDTAVYYCARGGYYYYAMDVWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPELLGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK (Light Chain Ab43)
SEQ ID NO: 29
QSVLTQPPSASGTPGQRVTISCSGGSSNIGYKTVNWYQQL

PGTAPKLLIYDNNKRPSGVPDRFSGSKSGTSASLAISGLR

SEDEADYYCAAWDDSLNGLVFGGGTKLTVLGQPKANPTVT

LFPPSSEELQANKATLVCLISDFYPGAVTVAWKADGSPVK

AGVETTKPSKQSNNKYAASSYLSLTPEQWKSHRSYSCQVT

HEGSTVEKTVAPTECS (Heavy Chain Ab72)
SEQ ID NO: 30
EVQLLESGGGLVQPGGSLRLSCAASGFTFSSYGMNWVRQA

PGKGLEWVSGISGSGGSTYYADSVKGRFTISRDNSKNTLY

LQMNSLRAEDTAVYYCAKDSNYDFWSGYYYGMDVWGQGTL

VTVSSASTKGPSVFPLAPSSKSTSGGTAALGCLVKDYFPE

PVTVSWNSGALTSGVHTFPAVLQSSGLYSLSSVVTVPSSS

LGTQTYICNVNHKPSNTKVDKRVEPKSCDKTHTCPPCPAP

ELLGGPSVFLFPPKPKDTLMISRTPEVTCVVVDVSHEDPE

VKFNWYVDGVEVHNAKTKPREEQYNSTYRVVSVLTVLHQD

WLNGKEYKCKVSNKALPAPIEKTISKAKGQPREPQVYTLP

PSREEMTKNQVSLTCLVKGFYPSDIAVEWESNGQPENNYK

TTPPVLDSDGSFFLYSKLTVDKSRWQQGNVFSCSVMHEAL

HNHYTQKSLSLSPGK (Light Chain Ab72)
SEQ ID NO: 31
QSVLTQPPSASGTPGQRVTISCSGSSSNIGSKTVSWYQQL

PGTAPKLLIYDNNKRPSGVPDRFSGSKSGTSASLAISGLR

SEDEADYYCSSYAARSTNIIFGGGTKLTVLGQPKANPTVT

LFPPSSEELQANKATLVCLISDFYPGAVTVAWKADGSPVK

AGVETTKPSKQSNNKYAASSYLSLTPEQWKSHRSYSCQVT

HEGSTVEKTVAPTECS (Heavy Chain Ab110)
SEQ ID NO: 32
EVQLLESGGGLVQPGGSLRLSCAASGFTFSSYGMHWVRQA

PGKGLEWVSIIYSGGSTYYADSVKGRFTISRDNSKNTLYL

QMNSLRAEDTAVYYCARRATWGGATHDYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPELLGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

-continued

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK (Light Chain Ab110)
SEQ ID NO: 33
QSVLTQPPSASGTPGQRVTISCSGSSSNIGSNTVNWYQQL

PGTAPKLLIYRNNQRPSGVPDRFSGSKSGTSASLAISGLR

SEDEADYYCATWDDSLNGVLFGGGTKLTVLGQPKANPTVT

LFPPSSEELQANKATLVCLISDFYPGAVTVAWKADGSPVK

AGVETTKPSKQSNNKYAASSYLSLTPEQWKSHRSYSCQVT

HEGSTVEKTVAPTECS (Heavy Chain Ab19) w/constant
SEQ ID NO: 34
EVQLLESGGGLVQPGGSLRLSCAASGFTFNNYDMTWVRQA

PGKGLEWVAVISYDGSDKDYADSVKGRFTISRDNSKNTLY

LQMNSLRAEDTAVYYCARVYYYGFSGPSMDVWGQGTLVTV

SSASTKGPSVFPLAPSSKSTSGGTAALGCLVKDYFPEPVT

VSWNSGALTSGVHTFPAVLQSSGLYSLSSVVTVPSSSLGT

QTYICNVNHKPSNTKVDKRVEPKSCDKTHTCPPCPAPELL

GGPSVFLFPPKPKDTLMISRTPEVTCVVVDVSHEDPEVKF

NWYVDGVEVHNAKTKPREEQYNSTYRVVSVLTVLHQDWLN

GKEYKCKVSNKALPAPIEKTISKAKGQPREPQVYTLPPSR

EEMTKNQVSLTCLVKGFYPSDIAVEWESNGQPENNYKTTP

PVLDSDGSFFLYSKLTVDKSRWQQGNVFSCSVMHEALHNH

YTQKSLSLSPGK (Light Chain Ab19) w/constant
SEQ ID NO: 35
QSVLTQPPSASGTPGQRVTISCSGSNSIGSNTVNWYQQL

PGTAPKLLIYSDSNRPSGVPDRFSGSKSGTSASLAISGLR

SEDEADYYCQSYDSSLSGSRVFGGGTKLTVLGQPKANPTV

TLFPPSSEELQANKATLVCLISDFYPGAVTVAWKADGSPV

KAGVETTKPSKQSNNKYAASSYLSLTPEQWKSHRSYSCQV

THEGSTVEKTVAPTECS

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention

---

The invention claimed is:

1. A method for assaying CD38-expressing cells in whole blood, the method comprising:

a) obtaining a sample of whole blood from a subject with an autoimmune disease, wherein the sample includes red blood cells, white blood cells and an anticoagulant;

b) lysing the red blood cells to form a treated sample;

c) freezing the treated sample to form a frozen sample, wherein freezing occurs within about 24 hours of obtaining the sample of whole blood from the subject;

d) measuring the level of CD38-expressing cells in the sample relative to a control subject without the autoimmune disease by flow cytometry within about 72 hours of obtaining the sample, wherein the frozen sample is warmed to room temperature before measuring the level of CD38-expressing cells, wherein the CD38-expressing cells are stained with an anti-CD38 antibody conjugated to a fluorochrome, and wherein the anti-CD38 antibody comprises:

1) a heavy chain variable region comprising:

i) a first CDR comprising SEQ ID NO: 3;

ii) a second CDR comprising SEQ ID NO: 4; and
iii) a third CDR comprising SEQ ID NO: 5; and
2) a light chain variable region comprising:
i) a first CDR comprising SEQ ID NO: 6;
ii) a second CDR comprising SEQ ID NO: 7; and
iii) a third CDR comprising SEQ ID NO: 8; or
1) a heavy chain variable region comprising:
i) a first CDR comprising SEQ ID NO: 13;
ii) a second CDR comprising SEQ ID NO: 14; and
iii) a third CDR comprising SEQ ID NO: 15; and
2) a light chain variable region comprising:
i) a first CDR comprising SEQ ID NO: 16;
ii) a second CDR comprising SEQ ID NO: 17; and
iii) a third CDR comprising SEQ ID NO: 18;
e) measuring the level of CD38-expressing cells relative to the control subject by assaying for free Ig light chains; and
f) measuring the expression of a biomarker for an elevated expression level of at least one CD38-expressing cell-enriched gene relative to the control subject, wherein the biomarker comprises mRNA and the at least one CD38-expressing cell-enriched gene comprises CD38.

2. The method of claim 1, wherein the frozen sample is maintained at a temperature of about −20° C. or less prior to measuring the level of CD38-expressing cells.

3. The method of claim 1, wherein the CD38-expressing cells are plasma cells and plasmablasts.

4. The method of claim 1, wherein the CD38-expressing cells are plasma cells.

5. The method of claim 1, wherein the CD38-expressing cells are plasmablasts.

6. The method of claim 2, wherein the frozen sample is maintained at a temperature of about −80° C. prior to measuring the level of CD38-expressing cells.

7. The method of claim 1, wherein the anti-CD38 antibody is an anti-CD38 antibody conjugated to fluorescein isothionate.

8. The method of claim 1, wherein the at least one gene further comprises IgJ.

9. The method of claim 1, wherein measuring mRNA comprises a PCR method, RNA sequencing, or a microarray chip.

10. The method of claim 1, wherein the autoimmune disease is selected from the group consisting of myasthenia gravis, autoimmune thrombocytopenia, immune mediated thrombocytopenia, idiopathic thrombocytopenia purpura, thrombotic thrombocytopenia purpura, rheumatoid arthritis, systemic lupus erythematosus, inflammatory bowel disease, ulcerative colitis, graft-versus host disease, Sjogren's syndrome, multiple sclerosis, and autoimmune thyroiditis.

11. The method of claim 10, wherein the autoimmune disease is systemic lupus erythematosus.

12. The method of claim 1, wherein the subject has been treated with an anti-CD20 antibody.

13. The method of claim 1, wherein the subject is unresponsive to CD20 based therapies.

14. The method of claim 1, wherein the heavy chain variable region comprises SEQ ID NO: 9 and the light chain variable region comprises SEQ ID NO: 10, or wherein the heavy chain variable region comprises SEQ ID NO: 19 and the light chain variable region comprises SEQ ID NO: 20.

15. The method of claim 1, wherein the frozen sample is maintained at a temperature of from about −20° C. to about −70° C. prior to measuring the level of CD38-expressing cells.

16. The method of claim 1, wherein the subject is shown to have, prior to treatment with an anti-CD38 antibody, an elevated level of CD38-expressing cells relative to the control subject.

17. The method of claim 1, wherein the subject is shown to have, following treatment with an anti-CD20 antibody, an elevated level of CD38-expressing cells relative to the control subject.

18. The method of claim 1, wherein the sample is obtained from the subject prior to treatment with an anti-CD38 antibody, and is shown to have an elevated level of CD38-expressing cells and/or an elevated level of at least one CD38-expressing cell-enriched gene relative to the control subject.

19. The method of claim 1, wherein the sample is obtained from the subject following treatment with an anti-CD20 antibody, and is shown to have an elevated level of CD38-expressing cells and/or an elevated level of at least one CD38-expressing cell-enriched gene relative to the control subject.

* * * * *